(12) United States Patent
Asano et al.

(10) Patent No.: US 10,488,355 B2
(45) Date of Patent: Nov. 26, 2019

(54) GAS CONCENTRATION-THICKNESS PRODUCT MEASUREMENT DEVICE, GAS CONCENTRATION-THICKNESS PRODUCT MEASUREMENT METHOD, AND COMPUTER-READABLE RECORDING MEDIUM HAVING GAS CONCENTRATION-THICKNESS PRODUCT MEASUREMENT PROGRAM RECORDED THEREON

(71) Applicant: KONICA MINOLTA, INC., Chiyoda-ku (JP)

(72) Inventors: Motohiro Asano, Osaka (JP); Takashi Morimoto, Suita (JP)

(73) Assignee: Konica Minolta, Inc., Tokyo (JP)

( * ) Notice: Subject to any disclaimer, the term of this patent is extended or adjusted under 35 U.S.C. 154(b) by 0 days.

(21) Appl. No.: 15/780,529

(22) PCT Filed: Dec. 12, 2016

(86) PCT No.: PCT/JP2016/086891
§ 371 (c)(1),
(2) Date: May 31, 2018

(87) PCT Pub. No.: WO2017/104607
PCT Pub. Date: Jun. 22, 2017

(65) Prior Publication Data
US 2018/0364185 A1 Dec. 20, 2018

(30) Foreign Application Priority Data
Dec. 15, 2015 (JP) ................................ 2015-244192

(51) Int. Cl.
*G01N 25/72* (2006.01)
*G01M 3/02* (2006.01)
(Continued)

(52) U.S. Cl.
CPC .............. *G01N 25/72* (2013.01); *G01M 3/02* (2013.01); *G01N 21/3504* (2013.01); *G01N 2021/1714* (2013.01); *G01N 2021/3531* (2013.01)

(58) Field of Classification Search
CPC ...... G01N 25/72; G01N 21/3504; G01M 3/02
See application file for complete search history.

(56) References Cited

U.S. PATENT DOCUMENTS

| 5,306,913 A | 4/1994 | Noack et al. |
| 5,430,293 A | 7/1995 | Sato et al. |

(Continued)

FOREIGN PATENT DOCUMENTS

| JP | 6-331480 | 12/1994 |
| JP | 2009-174990 | 8/2009 |

(Continued)

OTHER PUBLICATIONS

Preliminary Report on Patentability dated Jun. 19, 2018 which issued in the corresponding International Patent Application No. PCT/JP2016/086891.

(Continued)

*Primary Examiner* — Hugh Maupin
(74) *Attorney, Agent, or Firm* — Cozen O'Connor

(57) ABSTRACT

Provided is a gas concentration length measurement device into which image data (moving image data) representing a plurality of infrared images is input, the image data being obtained by taking infrared images of a gas leakage monitoring target at a plurality of times. The gas concentration length measurement device generates chronological pixel data in which pieces of pixel data for pixels that are at the same positions in the plurality of infrared images are arranged chronologically, then uses the chronological pixel data for a predetermined pixel among the plurality of pixels (Continued)

constituting the infrared images as a basis to determine a with-gas background temperature indicating the background temperature when a gas is present in a predetermined region corresponding to the predetermined pixel and a without-gas background temperature indicating the background temperature when gas is not present in the predetermined region.

21 Claims, 45 Drawing Sheets

(51) Int. Cl.
    *G01N 21/3504*     (2014.01)
    *G01N 21/17*     (2006.01)

(56) References Cited

U.S. PATENT DOCUMENTS

| | | | |
|---|---|---|---|
| 5,656,813 A * | 8/1997 | Moore | G01N 21/3504 250/330 |
| 7,075,653 B1 | 7/2006 | Rutherford | |
| 8,502,152 B1 | 8/2013 | Hashmonay et al. | |
| 2017/0363541 A1 * | 12/2017 | Sandsten | G01N 21/3504 |

FOREIGN PATENT DOCUMENTS

| | | |
|---|---|---|
| JP | 2011-185926 | 9/2011 |
| JP | 2011-237213 | 11/2011 |
| JP | 2012-58093 | 3/2012 |
| JP | 2012-220313 | 11/2012 |
| WO | WO 96/31766 | 10/1996 |

OTHER PUBLICATIONS

Japanese Office Action issued in the corresponding Japanese application No. 2017-556039.
Search Report dated Aug. 2, 2018 which issued in the corresponding European Patent Application No. 16875584.1.

* cited by examiner

GAS TEMPERATURE > WITH-GAS BACKGROUND TEMPERATURE > WITHOUT-GAS BACKGROUND TEMPERATURE

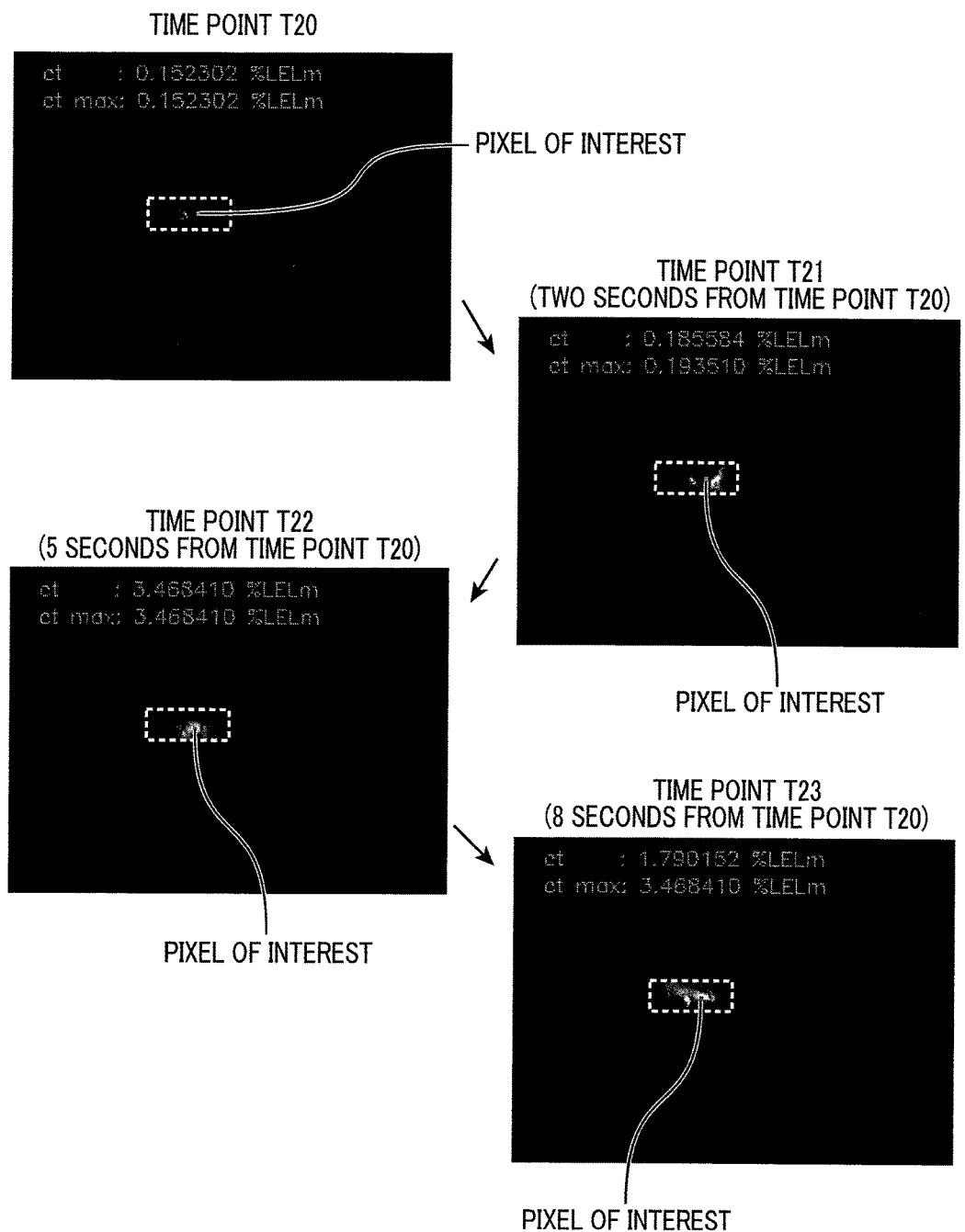

FIG. 16
WITH CORRECTION | WITHOUT CORRECTION
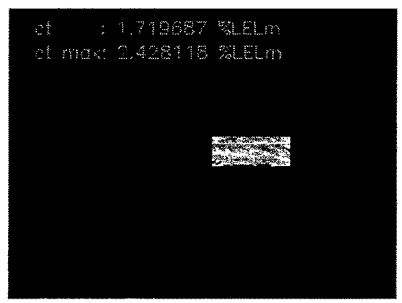
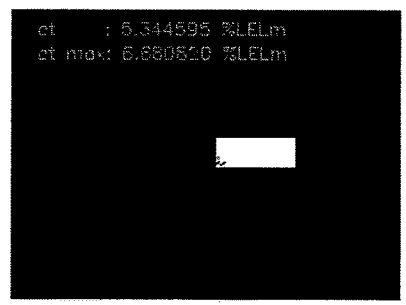
45th FRAME
(1.5 SECONDS LATER)
BEFORE START OF
GAS EMISSION
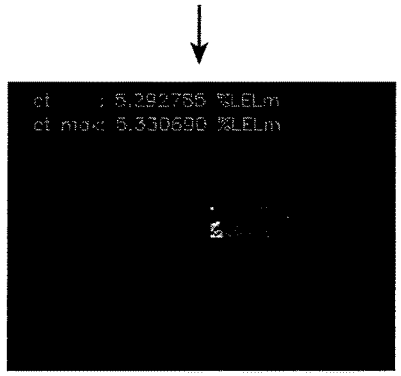
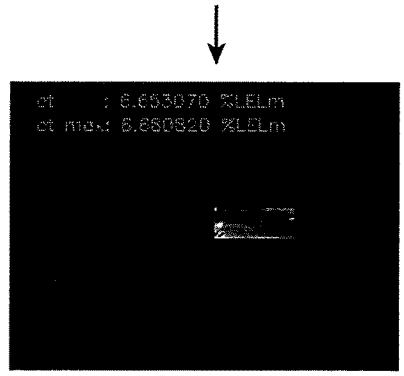
120th FRAME
(4 SECONDS LATER)
AFTER START OF
GAS EMISSION
500th FRAME
(16.7 SECONDS LATER)
AFTER START OF
GAS EMISSION

FIG. 37

CALCULATION FORMULA FOR CONCENTRATION LENGTH:

$$I_{gas} = \int_{\lambda_1}^{\lambda_2} P_{back}\tau_{air}(\lambda)\tau_{gas}(\lambda) + B(T_{gas},\lambda)\tau_{air}(\lambda)(1-\tau_{gas}(\lambda)) + B(T_{air},\lambda)(1-\tau_{air}(\lambda))d\lambda \quad \text{WITH-GAS BACKGROUND SIGNAL}$$

$$I_{no\_gas} = \int_{\lambda_1}^{\lambda_2} P_{back}\tau_{air}(\lambda) + B(T_{air},\lambda)(1-\tau_{air}(\lambda))d\lambda \quad \text{WITHOUT-GAS BACKGROUND SIGNAL}$$

$B(T,\lambda)$   BLACK BODY LUMINANCE AT ABSOLUTE TEMPERATURE T, WAVELENGTH $\lambda$ $P_{back}$   BACKGROUND OBJECT INFRARED INTENSITY $\tau_{air}(\lambda)$   ATMOSPHERIC AIR SPECTRAL TRANSMITTANCE $\tau_{gas}(\lambda) = \exp(-\alpha(\lambda)ct)$   GAS SPECTRAL TRANSMITTANCE $\alpha(\lambda)$   GAS SPECTRAL ABSORPTION $ct$   CONCENTRATION LENGTH $\lambda$   WAVELENGTH

FLOW OF CALCULATION PROCESSING:

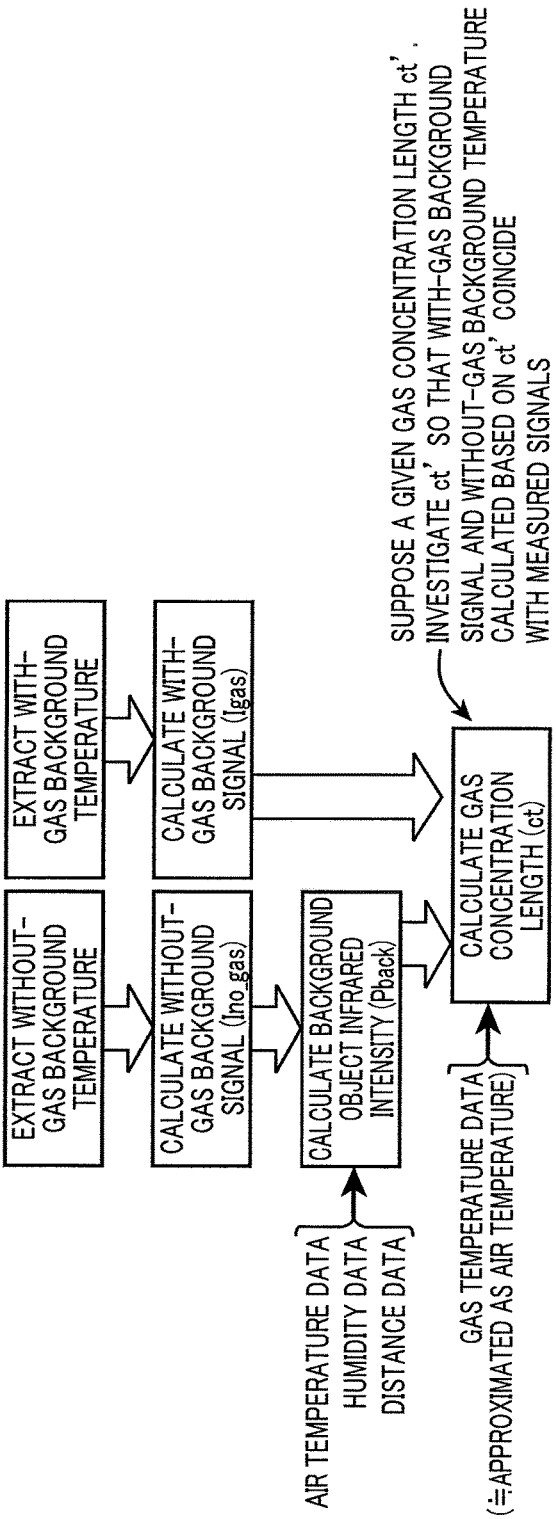

FIG. 38

EXAMPLE IN WHICH AMPLITUDES AT TWO POSITIONS ARE USED $$I_{gas\_1} = \int_{\lambda_1}^{\lambda_2} P_{back\_1}\tau_{air}(\lambda)\tau_{gas}(\lambda) + B(T_{gas},\lambda)\tau_{air}(\lambda)(1-\tau_{gas}(\lambda)) + B(T_{air},\lambda)(1-\tau_{air}(\lambda))d\lambda$$

$$I_{gas\_2} = \int_{\lambda_1}^{\lambda_2} P_{back\_2}\tau_{air}(\lambda)\tau_{gas}(\lambda) + B(T_{gas},\lambda)\tau_{air}(\lambda)(1-\tau_{gas}(\lambda)) + B(T_{air},\lambda)(1-\tau_{air}(\lambda))d\lambda$$

$$I_{gas\_2} - I_{gas\_1} = \int_{\lambda_1}^{\lambda_2} (P_{back\_2} - P_{back\_1})\tau_{air}(\lambda)\tau_{gas}(\lambda)d\lambda$$

FLOW OF CALCULATION PROCESSING:

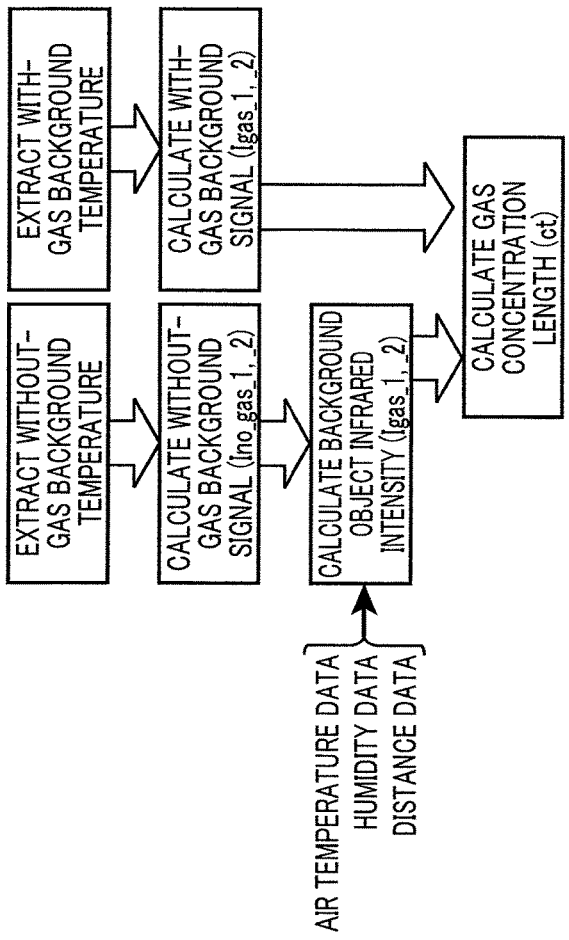

GAS CONCENTRATION-THICKNESS PRODUCT MEASUREMENT DEVICE, GAS CONCENTRATION-THICKNESS PRODUCT MEASUREMENT METHOD, AND COMPUTER-READABLE RECORDING MEDIUM HAVING GAS CONCENTRATION-THICKNESS PRODUCT MEASUREMENT PROGRAM RECORDED THEREON

RELATED APPLICATIONS

This is a U.S. National Phase Application under 35 USC 371 of International Application PCT/JP2016/086891 filed on Dec. 12, 2016.

This application claims the priority of Japanese application no. 2015-244192 filed Dec. 15, 2015, the entire content of which is hereby incorporated by reference.

FIELD OF THE INVENTION

Technical Field

The present invention relates to a technique for detecting gas by using an infrared camera.

Background Art

When gas leakage occurs, a slight temperature change occurs in the space in which the gas having leaked is hanging. As a technique for performing gas detection by using this principle, gas detection by using infrared cameras is known.

For example, Patent Literature 1 discloses a gas detection device including: a first infrared camera that measures an intensity of infrared light of a first wavelength region, the infrared light of the first wavelength region being absorbed by a detection target gas; a second infrared camera that measures an intensity of infrared light of a second wavelength region, the second wavelength region being composed of the first wavelength region and a wavelength region differing from the first wavelength region; and a determination unit that determines whether the detection target gas is present or not on the basis of a result measured by the first infrared camera and a result measured by the second infrared camera.

In Patent Literature 1, gas is detected by using two infrared cameras. Meanwhile, as gas detection by using one infrared camera, Patent Literature 2, for example, discloses the following gas detection method. In this method, one infrared camera, a first filter that has a transmission band including an absorption line indicating a characteristic of a gas being searched for, and a second filter that has a transmission band similar to the transmission band of the first filter and does not allow the absorption line to pass therethrough are used. This method includes: a step of detecting, by using the infrared camera, radiant fluxes coming from two points with different temperatures through the first filter; a step of switching from the first filter to the second filter and detecting, by using the infrared camera, the radiant fluxes coming from the two points through the second filter; and a step of deducing whether the gas is present or not on the basis of these detection results.

When gas leakage is detected, it is necessary to determine the degree of danger of the gas (for example, the possibility of explosion). The degree of danger of gas can be determined from gas concentration in the space in which the gas is hanging. However, gas concentration in a space in which gas is hanging cannot be directly measured through remote gas detection using infrared cameras, and measurement of gas concentration lengths is performed. A gas concentration length indicates a value yielded through integration of gas concentration along a depth direction of a space in which the gas is hanging.

An infrared image is constituted by a plurality of pixels being arrayed two-dimensionally. A background is virtually divided into a plurality of regions respectively corresponding to the plurality of pixels. Pixel data for each pixel indicates a background temperature of the corresponding region. In order to calculate a concentration length of gas located in a given region, a background temperature of the region when gas is present in the region (a with-gas background temperature) and a background temperature of the region when gas is not present in the region (a without-gas background temperature) are required.

In order to realize this by using one infrared camera, the measurement of background temperatures is performed by switching between filters, in the technique disclosed in Patent Literature 2. Specifically, in the technique disclosed in Patent Literature 2, the with-gas background temperature and the without-gas background temperature are measured by preparing a filter transmitting a wavelength region that is absorbed by a detection target gas and a filter not transmitting the wavelength region, and measuring background temperatures by using an infrared camera while switching between these two types of filters.

The technique disclosed in Patent Literature 2, however, requires two types of filters and a mechanism for switching between the filters.

CITATION LIST

Patent Literature

Patent Literature 1: JP 2011-237213 A
Patent Literature 2: U.S. Pat. No. 5,306,913

SUMMARY OF INVENTION

The present invention aims to provide a gas concentration length measurement device, a gas concentration length measurement method, and a computer-readable recording medium having a gas concentration length measurement program recorded thereon which enable measurement of the with-gas background temperature and the without-gas background temperature with one infrared camera, without requiring two types of filters and a mechanism for switching between the filters.

A gas concentration length measurement device relating to a first aspect of the present invention achieving the above-described aim is a gas concentration length measurement device for measuring a gas concentration length by using an infrared image constituted of a plurality of pixels, the gas concentration length measurement device including an image data input unit and a first determination unit. The image data input unit receives input of image data representing a plurality of the infrared images yielded by the infrared image of a gas leakage monitoring target being taken at a plurality of time points. The first determination unit generates chronological pixel data in which pieces of pixel data for the pixels located at a same position in the plurality of infrared images input from the image data input unit are lined-up in chronological order, and on the basis of the chronological pixel data for a predetermined pixel among the plurality of pixels, determines: a with-gas background temperature indicating a background temperature when gas is present in a predetermined region corresponding to the predetermined pixel; and a without-gas background temperature indicating a background temperature when gas is not present in the predetermined region.

These and other objects, features, and advantages of the present invention will become more apparent from the following detailed description of the present invention when taken in conjunction with the accompanying drawings.

BRIEF DESCRIPTION OF DRAWINGS

FIG. 10 is an image diagram showing a transition of infrared images displayed on a display unit during execution of the first mode of the present embodiment.

FIG. 16 is an image diagram showing a transition of infrared images displayed on the display unit during execution of each of the first and second modes of the present embodiment.

FIG. 37 is an explanatory diagram describing a first method for calculating a gas concentration length.

FIG. 38 is an explanatory diagram describing a second method for calculating the gas concentration length.

DESCRIPTION OF EMBODIMENT

Figure 1:
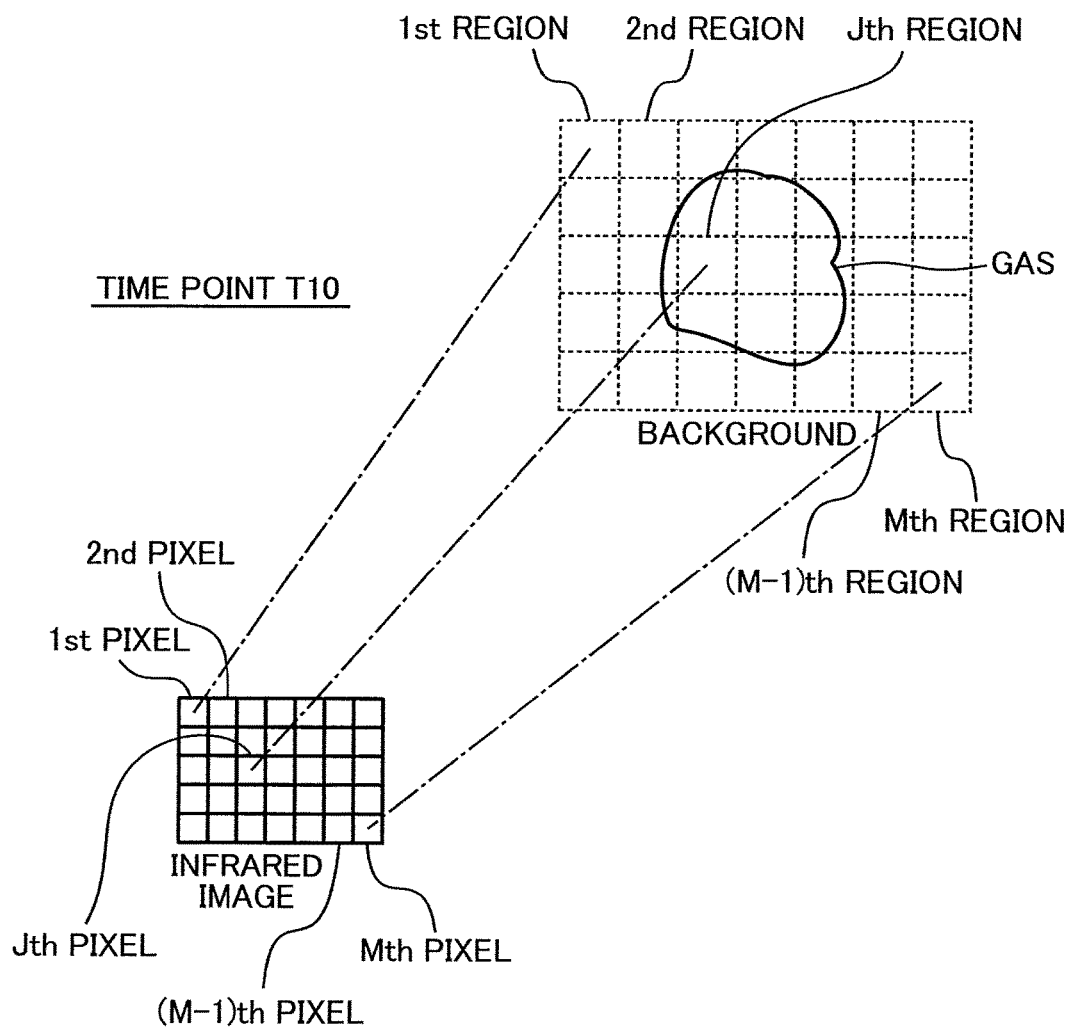
FIG. 1 is an explanatory diagram describing a relation between an infrared image taken at time point T10 and a background including gas.

In the following, an embodiment of the present invention is described in detail on the basis of the drawings. In the drawings, structures provided with the same symbol indicate the same structure, and regarding such a structure, description of matters already described is omitted.

FIG. 1 is an explanatory diagram describing a relation between an infrared image taken at time point T10 and a background including gas. Gas is leaking from a gas leakage monitoring target (for example, a connection point of gas transport pipes) and is hanging in the space. The infrared image is constituted by an M number of pixels from a 1st pixel to an Mth pixel being arrayed two-dimensionally. M denotes two or more. The background is virtually divided into an M number of regions from a 1st region to an Mth region, respectively corresponding to the M number of pixels. For example, the 1st pixel corresponds to the 1st region, and pixel data for the 1st pixel indicates a background temperature of the 1st region. A Jth pixel corresponds to a Jth region, and pixel data for the Jth pixel indicates a background temperature of the Jth region.

In order to calculate a concentration length of gas located in a given region, a background temperature of the region when gas is present in the region (a with-gas background temperature) and a background temperature of the region when gas is not present in the region (a without-gas background temperature) are required. For example, in order to calculate the concentration length of gas located in the Jth region, the with-gas background temperature of the Jth region and the without-gas background temperature of the Jth region are required.

Figure 2:
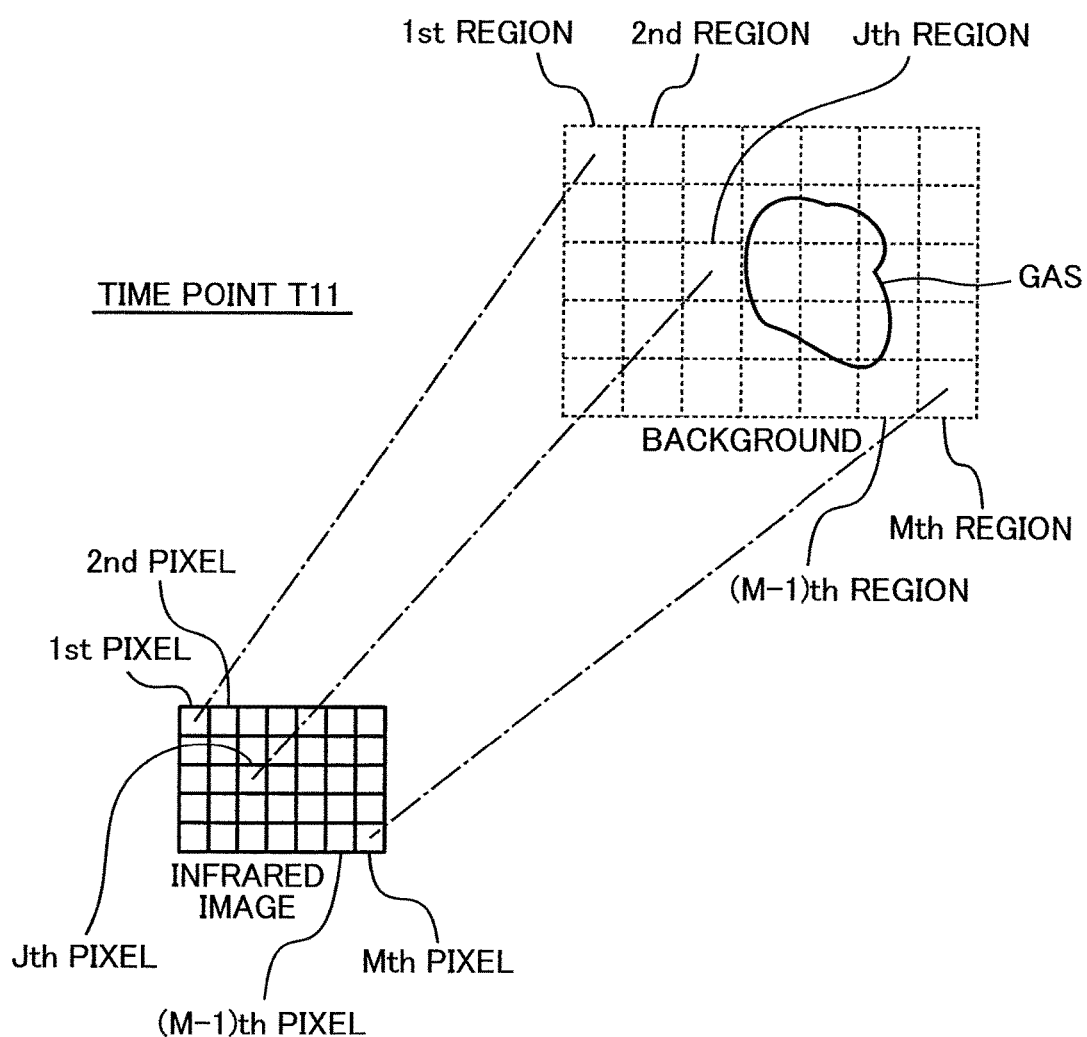
FIG. 2 is an explanatory diagram describing a relation between an infrared image taken at time point T11 and a background including gas.

In the state shown in FIG. 1, gas is located in the Jth region. Hence, the with-gas background temperature of the Jth region can be detected, but the without-gas background temperature of the Jth region cannot be detected. FIG. 2 is an explanatory diagram describing a relation between an infrared image taken at time point T11 differing from time point T10 and a background including gas. At time point T11, gas is not present in the Jth region. This is because the gas having leaked is swaying. Swaying of gas is caused by the wind, etc. The inventors of the present invention have found that, due to the swaying of gas having leaked, the possibility is high that, in the Jth region, a state in which gas is present and a state in which gas is not present occur when seen chronologically. It has been found that this possibility becomes higher as the distance from an infrared camera to the gas having leaked increases (for example, 10 m or more).

Figure 3:
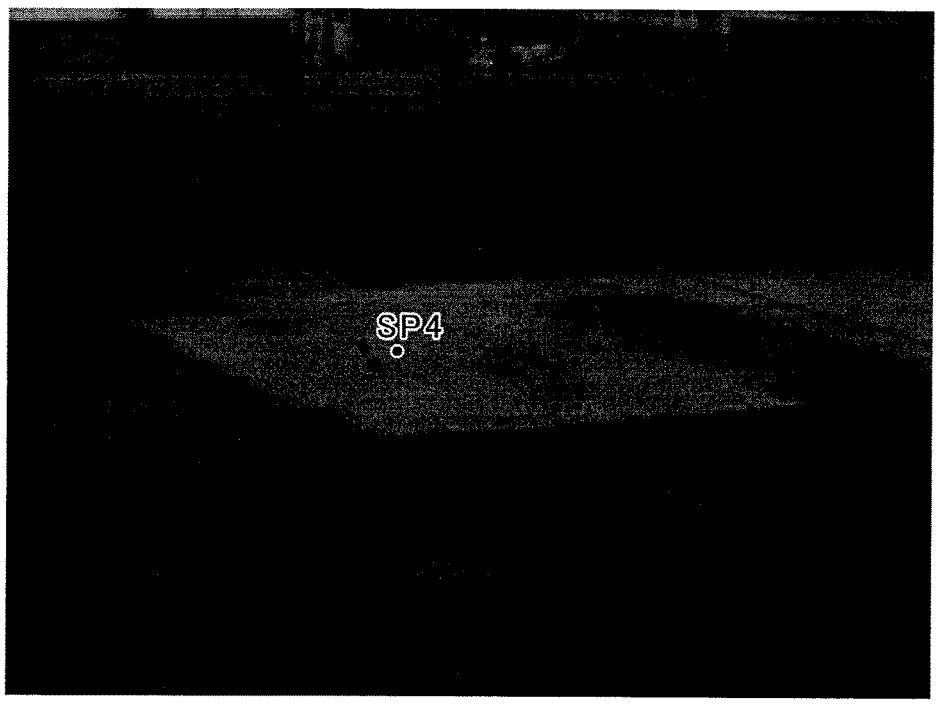
FIG. 3 is an image diagram showing an infrared image taken of an outdoor testing site.

Description is provided of the principle of the present embodiment. FIG. 3 is an image diagram showing an infrared image taken at an outdoor testing site. This infrared image has been yielded by taking a moving image by using an infrared camera. At the testing site, there is a spot SP4 capable of causing gas emission.

Figure 4:
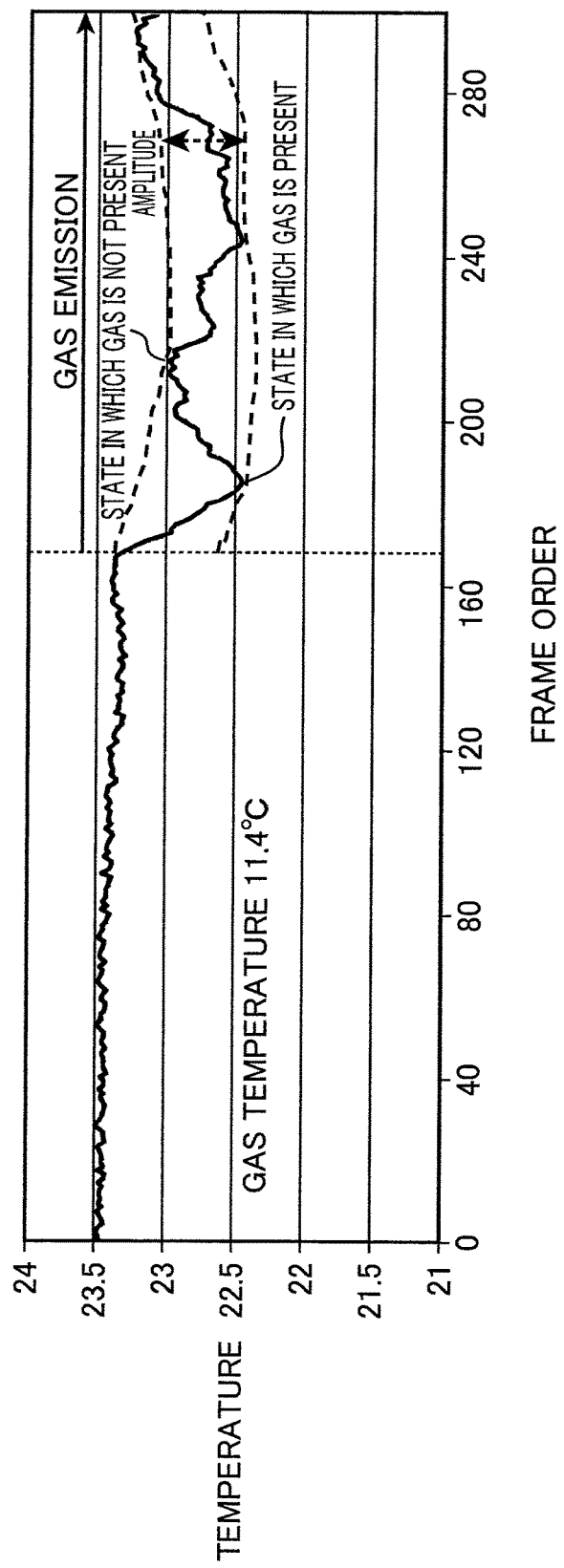
FIG. 4 is a graph showing a temperature change at spot SP4 (FIG. 3) of the testing site.

FIG. 4 is a graph showing a temperature change at spot SP4 of the testing site. The vertical axis of the graph indicates background temperature. The horizontal axis of the graph indicates frame order. For example, "160" indicates the 160th frame. The frame rate is 30 fps.

The gas temperature was 11.4° C., and was lower than the air temperature at the testing site (that is, the site at which the infrared image was taken). The background temperature at spot SP4 is decreasing starting from around the 170th frame. This is because the time point corresponding to this frame is the time point at which gas emission was started at spot SP4. The emission of gas at spot SP4 continues. From around the 170th frame and on, the background temperature at spot SP4 continues to change rather than remaining fixed. This is due to the swaying of the emitted gas, and because at spot SP4, a state in which gas is present and a state in which gas is not present occur. In the present embodiment, the with-gas background temperature and the without-gas background temperature are calculated by using data of a change in the background temperature after gas emission (amplitudes of a graph indicating the fluctuation of the background temperature).

Figure 5A:
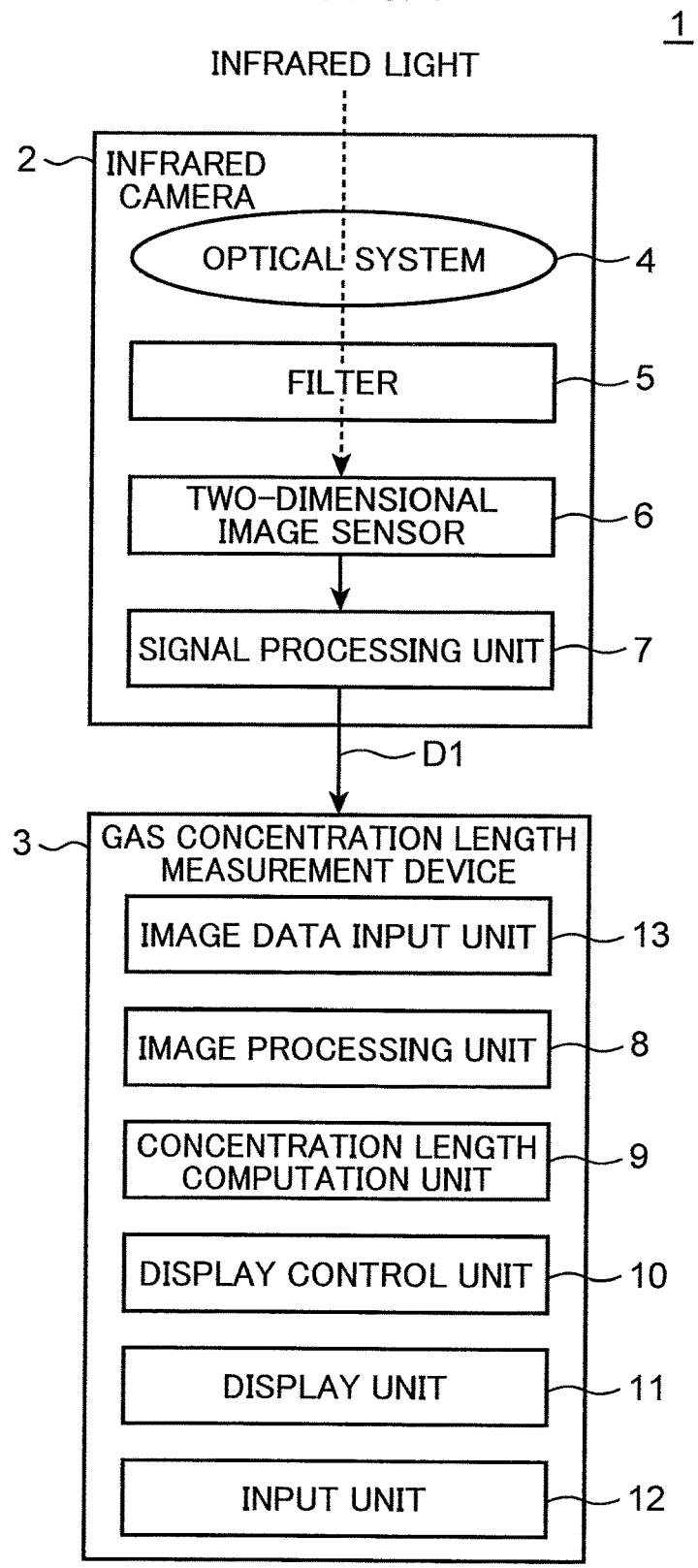
FIG. 5A is a block diagram showing a configuration of a gas concentration length measurement device relating to the present embodiment.

FIG. 5A is a block diagram showing a configuration of a gas concentration length measurement system 1 relating to the present embodiment. The gas concentration length measurement system 1 includes: an infrared camera 2; and a gas concentration length measurement device 3.

The infrared camera 2 takes a moving image of infrared images of a gas leakage monitoring target and a background, and generates moving image data D1 representing the moving image. The moving image data D1 is one example of image data of infrared images. The image data is not limited to a moving image, and an infrared image of the gas leakage monitoring target and the background may be taken at a plurality of time points by using the infrared camera 2. The infrared camera 2 includes: an optical system 4; a filter 5; a two-dimensional image sensor 6; and a signal processing unit 7.

The optical system 4 forms infrared images of the imaging subject (the monitoring subject and the background) on the two-dimensional image sensor 6. The filter 5 is arranged between the optical system 4 and the two-dimensional image sensor 6, and allows only infrared light of a specific wavelength, in the light having passed through the optical system 4, to pass therethrough. The wavelength range within the infrared wavelength range to be allowed to pass through the filter 5 depends upon the type of gas to be detected. For example, in the case of methane gas, a filter 5 allowing a wavelength range of 3.2 to 3.4 μm to pass therethrough is used. The two-dimensional image sensor 6 is, for example, a cooled-type indium antimonide (InSb) image sensor, and receives infrared light having passed through the filter 5. The signal processing unit 7 converts analog signals output from the two-dimensional image sensor 6 into digital signals, and performs known image processing. These digital signals become the moving image data D1.

The gas concentration length measurement device 3 is a personal computer, a smartphone, a tablet terminal, or the like, and includes as functional blocks: an image processing unit 8; a concentration length computation unit 9; a display control unit 10; a display unit 11; an input unit 12; and an image data input unit 13.

The image data input unit 13 is a communication interface that communicates with a communication unit (not shown in the drawings) of the infrared camera 2. The image data input unit 13 receives input of the moving image data D1 (image data) transmitted thereto from the communication unit of the infrared camera 2. The moving image data D1 is one example of image data. Image data is data representing a plurality of infrared images yielded by an infrared image of the gas leakage monitoring target being taken at a plurality of time points. The image data input unit 13 transmits the moving image data D1 to the image processing unit 8.

The image processing unit 8 is realized by using a central processing unit (CPU), a random access memory (RAM), a read-only memory (ROM), a hard disk drive (HDD), etc., and performs predetermined processing on the moving image data D1.

Figure 6:
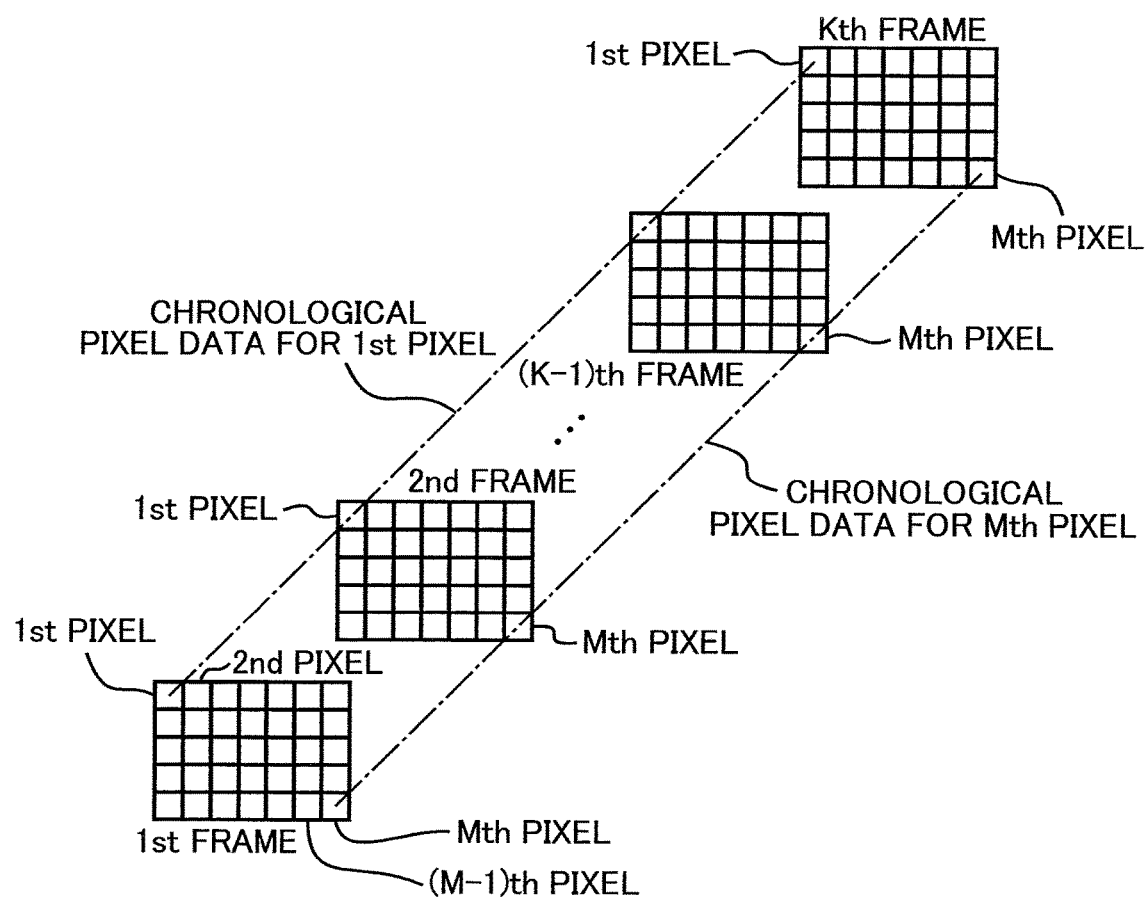
FIG. 6 is an explanatory diagram describing chronological pixel data.

The moving image represented by the moving image data D1 has a structure in which a plurality of frames are lined up in chronological order. Data in which pieces of pixel data for pixels located at the same position in the plurality of frames (a plurality of infrared images) are lined up in chronological order is referred to as chronological pixel data. The chronological pixel data is described specifically. FIG. 6 is an explanatory diagram describing the chronological pixel data. Suppose that the number of frames of the moving image of infrared images is K. Each frame is constituted of an M number of pixels, namely a 1st pixel, a 2nd pixel, ..., an (M−1)th pixel, and an Mth pixel. Pixel data represents a temperature of a background corresponding to the pixel.

Pixels located at the same position in the plurality of (K number of) frames refer to pixels of the same ordinal position. For example, when providing description based on the 1st pixel, the chronological pixel data for the 1st pixel is data in which the pixel data for the 1st pixel included in the 1st frame, the pixel data for the 1st pixel included in the 2nd frame, ..., the pixel data for the 1st pixel included in the (K−1)th frame, and the pixel data for the 1st pixel included in the Kth frame are lined up in chronological order. Further, when providing description based on the Mth pixel, the chronological pixel data for the Mth pixel is data in which the pixel data for the Mth pixel included in the 1st frame, the pixel data for the Mth pixel included in the 2nd frame, ..., the pixel data for the Mth pixel included in the (K−1)th frame, and the pixel data for the Mth pixel included in the Kth frame are lined up in chronological order. The number of pieces of chronological pixel data is equal to the number of pixels constituting a single frame.

Description regarding FIG. 5A starts once again. The concentration length computation unit 9 is realized by using a CPU, a RAM, a ROM, a HDD, etc. The concentration length computation unit 9 determines the with-gas background temperature and the without-gas background temperature on the basis of the chronological pixel data, and calculates an estimate value of the gas concentration length. Detailed description regarding this point is provided later.

The display control unit 10 is realized by using a CPU, a RAM, a ROM, a HDD, etc., and causes the display unit 11 to display the moving image represented by the moving image data D1, and the estimate value of the gas concentration length calculated by the concentration length computation unit 9. The display unit 11 is, for example, realized by using a liquid crystal display.

The input unit 12 is realized by using a keyboard or a touch panel, and receives various types of input related to gas detection.

Figure 5B:
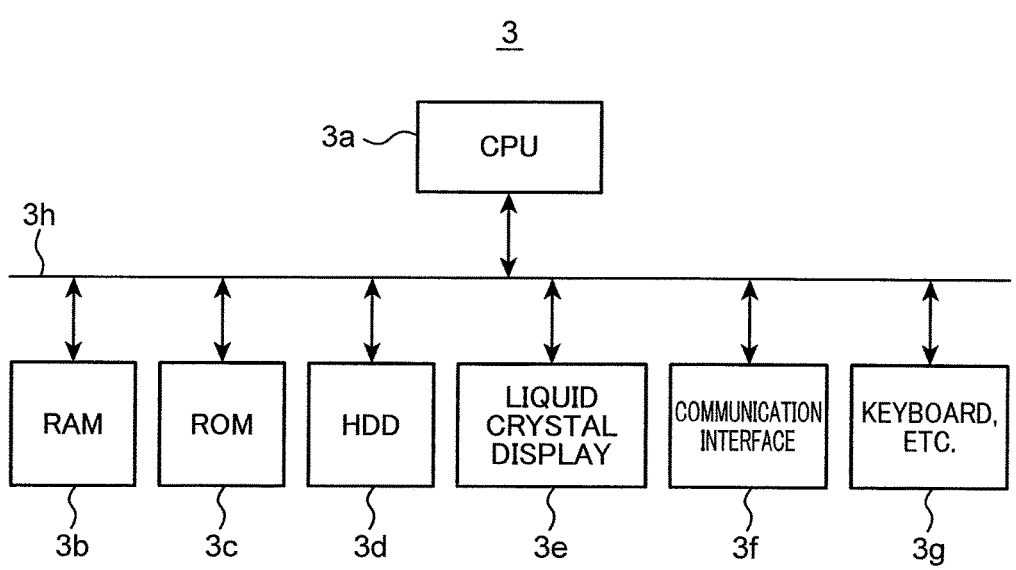
FIG. 5B is a block diagram showing a hardware configuration of the gas concentration length measurement device shown in FIG. 5A.

FIG. 5B is a block diagram showing a hardware configuration of the gas concentration length measurement device 3 shown in FIG. 5A. The gas concentration length measurement device 3 includes: a CPU 3a; a RAM 3b; a ROM 3c; a HDD 3d; a liquid crystal display 3e; a communication interface 3f; a keyboard, etc. 3g; and a bus 3h connecting such components. The liquid crystal display 3e is the hardware realizing the display unit 11. An organic light emitting diode display (an organic EL display), a plasma display, or the like may be used in place of the liquid crystal display 3e. The communication interface 3f is the hardware realizing the image data input unit 13. The keyboard, etc. 3g is the hardware realizing the input unit 12.

The HDD 3d stores therein programs for realizing functional blocks, namely the image processing unit 8, the concentration length computation unit 9, and the display control unit 10, which are shown in FIG. 5A. The program realizing the image processing unit 8 is a processing program that acquires the moving image data D1 (the image data) and performs the above-described predetermined processing on the moving image data D1. The program realizing the concentration length computation unit 9 is a computation program for performing computation of the gas concentration length. The gas concentration length is described later. The program realizing the display control unit 10 is a display control program that causes the display unit 11 to display images (for example, the moving image represented by the moving image data D1 on which the above-described predetermined processing has been performed). These programs may be stored in the ROM 3c instead of the HDD 3d.

The CPU 3a reads, from the HDD 3d, the processing program, the computation program, and the display control program, causes the RAM 3b to decompress the programs, and executes the decompressed programs, whereby the functional blocks are realized. The processing program, the computation program, and the display control program are stored in the HDD 3d in advance. The programs, however, need not be stored in the HDD 3d in advance. For example, a recording medium (for example, an external recording medium such as a magnetic disk or an optical disk) having these programs recorded thereon may be prepared, and the programs stored on the recording medium may be stored to the HDD 3d. Alternatively, these programs may be stored in a server that is connected to the gas concentration length measurement device 3 via a network, and may be transmitted to the HDD 3d via the network and stored to the HDD 3d.

Note that the gas concentration length measurement device 3 has the first through seventh modes as described next. These modes are each constituted of a plurality of elements. Hence, the HDD 3d has stored therein programs for realizing these elements. For example, the first mode of the gas concentration length measurement device 3 includes, as elements: a first determination unit; a calculation unit; a second determination unit; and an estimation unit. The HDD 3d has stored therein programs for realizing the first determination unit, the calculation unit, the second determination unit, and the estimation unit. These programs are referred to as a first determination program, a calculation program, a second determination program, and an estimation program.

These programs are referred to by using the definitions of the elements. Description is provided taking the first determination unit and the first determination program as an example. The first determination unit generates chronological pixel data (FIG. 6) in which pieces of pixel data for pixels at the same position in the moving image data D1 (the plurality of infrared images) input from the image data input unit 13 are lined up in chronological order, and on the basis of the chronological pixel data for a predetermined pixel among the plurality of pixels, determines the with-gas background temperature indicating a background temperature when gas is present in a predetermined region corresponding to the predetermined pixel and the without-gas background temperature indicating a background temperature when gas is not present in the predetermined region. The first determination program is a program that generates chronological pixel data (FIG. 6) in which pieces of pixel data for pixels at the same position in the moving image data D1 (the plurality of infrared images) input from the image data input unit 13 are lined up in chronological order, and on the basis of the chronological pixel data for a predetermined pixel among the plurality of pixels, determines the with-gas background temperature indicating a background temperature when gas is present in a predetermined region corresponding to the predetermined pixel and the without-gas background temperature indicating a background temperature when gas is not present in the predetermined region.

Figure 7:
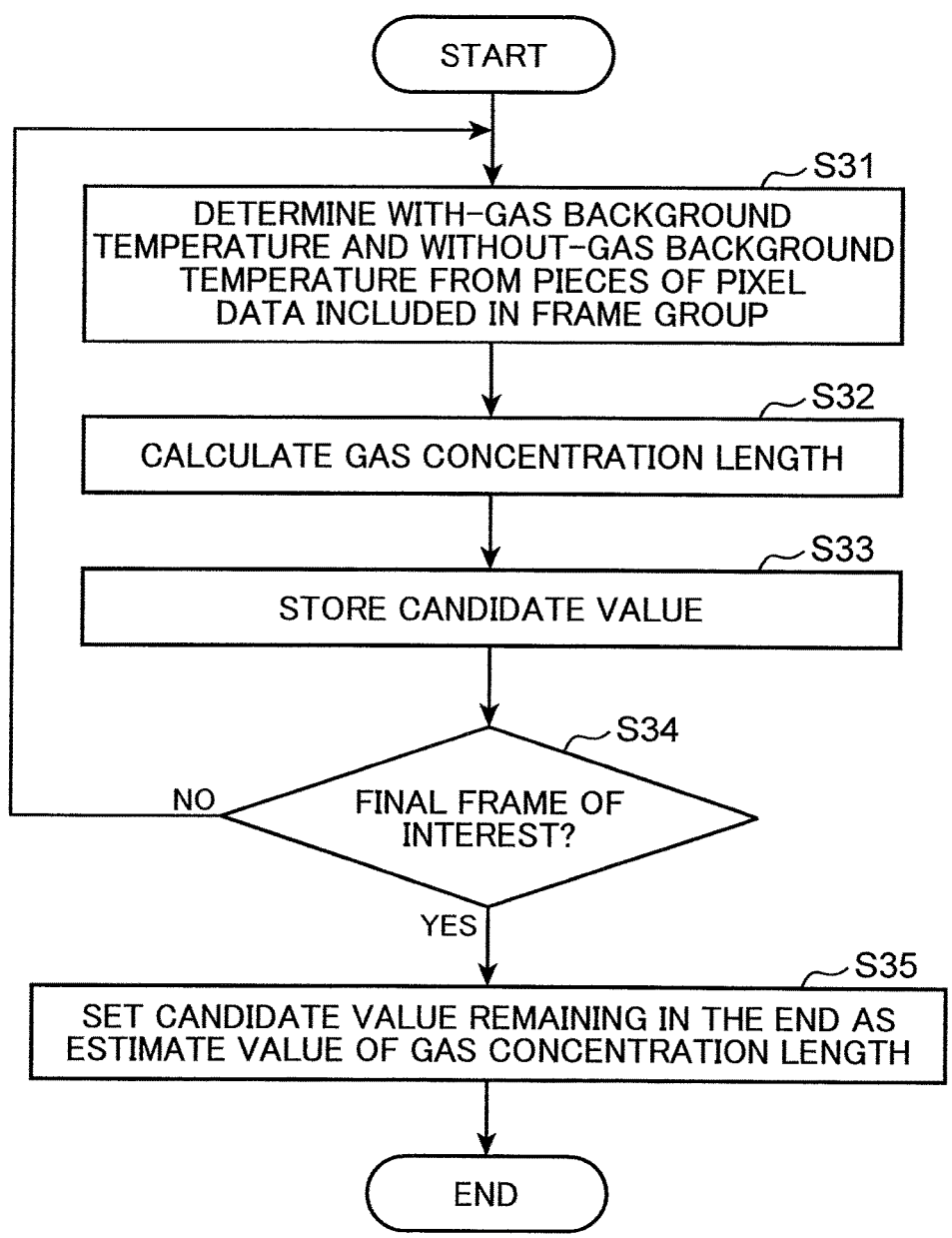
FIG. 7 is a flowchart of processing executed in a first mode of the present embodiment.

FIG. 7 described later is a flowchart of these programs executed by the CPU 3a (the first determination program, the calculation program, the second determination program, and the estimation program).

As described above, the present embodiment has the first to seventh modes. These modes can be combined with one another as long as no inconsistency occurs. Description is provided starting from the first mode of the present embodiment. FIG. 7 is a flowchart of processing executed in the first mode of the present embodiment. With reference to FIGS. 5A and 7, the display control unit 10 causes the display unit 11 to display an infrared image of a background including the gas leakage monitoring target. An operator determines, as a pixel of interest, a pixel of the infrared image displayed on the display unit 11 that the operator is interested in, and operates the input unit 12 to input the position of the pixel of interest (that is, specifies the pixel of interest). The pixel of interest is one example of the predetermined pixel, and is a pixel corresponding to a region in which gas having leaked is hanging. For example, the pixel corresponding to the Jth region shown in FIGS. 1 and 2, namely, the Jth pixel can be set as the pixel of interest. Description is provided in the following of an example in which the Jth pixel is the pixel of interest.

The concentration length computation unit 9 functions as the first determination unit. With reference to FIGS. 5A and 6, the first determination unit generates chronological pixel data for the Jth pixel from the moving image data D1. With reference to FIGS. 1 and 2, the first determination unit determines the with-gas background temperature and the without-gas background temperature for the Jth pixel (the pixel of interest, the predetermined pixel) among the M number of pixels, on the basis of the chronological pixel data for the Jth pixel. The without-gas background temperature and the with-gas background temperature, which is between the gas temperature and the without-gas background temperature, are background temperatures that are indicated by the pixel data for the Jth pixel.

To provide detailed description, the first determination unit determines, as a frame group, a group of a predetermined number of frames that are consecutive in chronological order, the predetermined number of frames being less than the K number of (the plurality of) frames shown in FIG. 6, and determines the with-gas background temperature and the without-gas background temperature from among background temperatures indicated by pieces of pixel data, in the chronological pixel data for the Jth pixel, that are included in the frame group (step S31). In other words, the first determination unit determines the with-gas background temperature and the without-gas background temperature from among background temperatures indicated by pieces of pixel data, in the chronological pixel data for the Jth pixel, that are included in a frame group including a predetermined number of consecutive frames.

Figure 8:
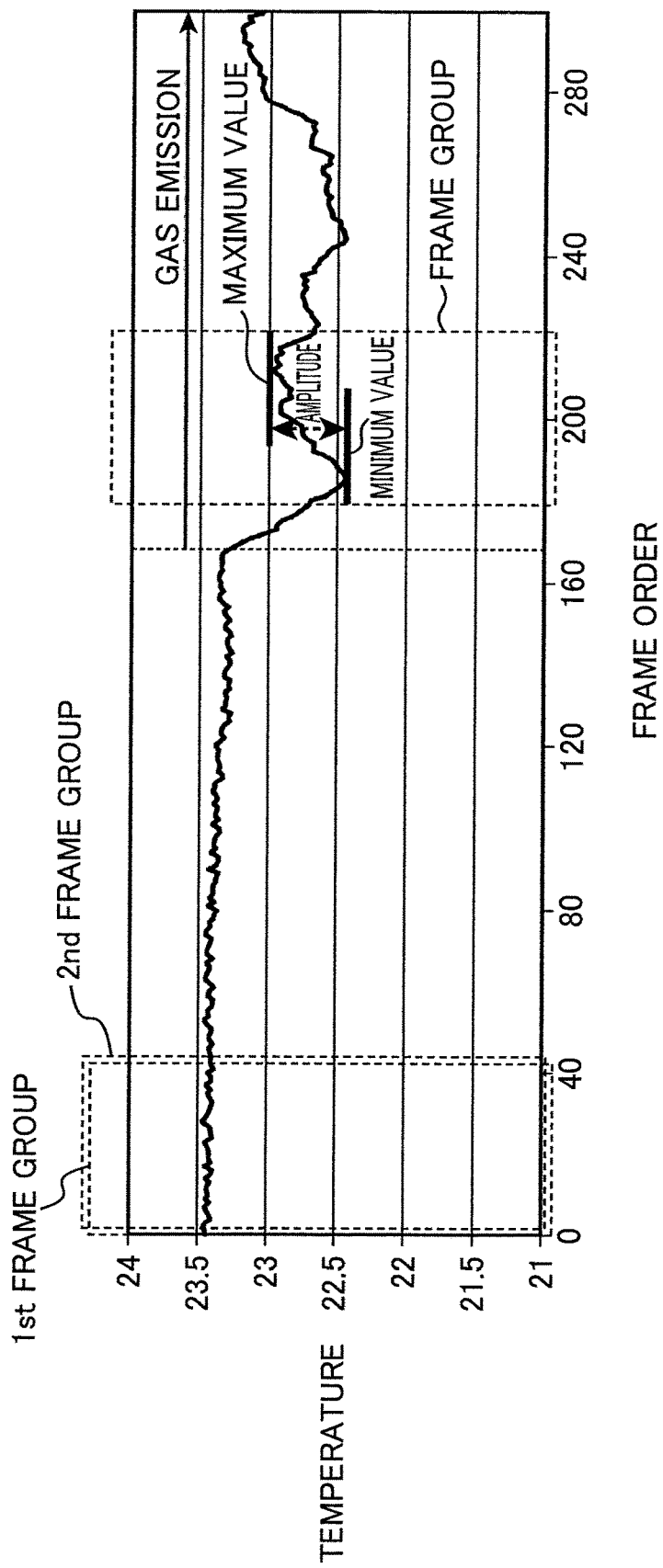
FIG. 8 is a graph showing a relation between frame groups and the temperature change at spot SP4 (FIG. 3) of the testing site.

A frame group is constituted of a predetermined number of frames that are consecutive in chronological order. Here, it is supposed that the predetermined number is 41, for example. A frame group is constituted of a frame of interest, 20 consecutive frames immediately before this frame, and 20 consecutive frames immediately after this frame. This is described on the basis of FIG. 8. FIG. 8 is a graph indicating a relation between frame groups and the temperature change at spot SP4 of the testing site. The vertical and horizontal axes and the line indicating the temperature change in the graph are the same as those shown in FIG. 4. The line indicating the temperature change is the chronological pixel data for a pixel corresponding to spot SP4. For example, when the frame of interest is the 200th frame, the 180th to 220th frames constitute one frame group. First, the 1st frame group is formed. The frame of interest in the 1st frame group is the 21st frame, and the 1st frame group is constituted of the 1st to 41st frames. When the number of frames is 300 for example, the final frame group is a frame group constituted of the 260th to 300th frames. The 1st through final frame groups are a plurality of frame groups having different combinations of frames.

The first determination unit determines maximum and minimum background temperature values from among background temperatures indicated by pieces of pixel data, in the chronological pixel data for the Jth pixel, that are included in the frame group. Here, the frame group is the 1st frame group.

Figure 9A:
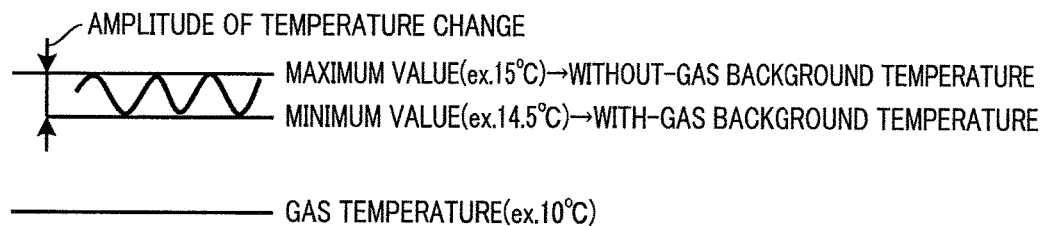
FIG. 9A is an explanatory diagram describing a relation between a gas temperature, a with-gas background temperature, and a without-gas background temperature when the gas temperature is lower than background temperatures.
Figure 9B:
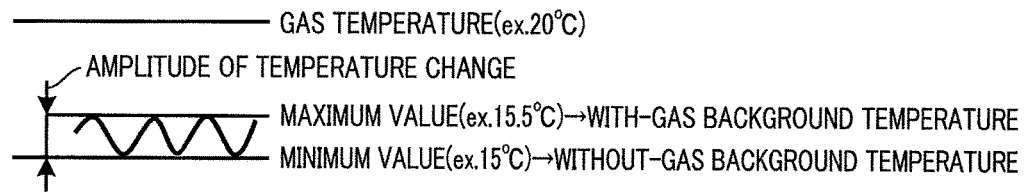
FIG. 9B is an explanatory diagram describing a relation between the gas temperature, the with-gas background temperature, and the without-gas background temperature when the gas temperature is higher than the background temperatures.

The maximum background temperature value becomes one of the with-gas background temperature and the without-gas background temperature, and the minimum background temperature value becomes the other one of the with-gas background temperature and the without-gas background temperature. This is dependent upon the relation between gas temperature, the with-gas background temperature, and the without-gas background temperature. This is described on the basis of FIGS. 9A and 9B. FIGS. 9A and 9B are explanatory diagrams describing the relation. The with-gas background temperature and the without-gas background temperature are background temperatures that are indicated by the pixel data for the Jth pixel (the predetermined pixel), among the plurality of pixels constituting the infrared image. When gas is included in the imaging subject, the with-gas background temperature is between the gas temperature and the without-gas background temperature. When the gas temperature is lower than the background temperatures indicated by the pixel data for the Jth pixel (the predetermined pixel), the following relationship holds true (FIG. 9A): without-gas background temperature>with-gas background temperature>gas temperature. When the gas temperature is higher than the background temperatures indicated by the pixel data for the Jth pixel, the following relationship holds true (FIG. 9B): gas temperature>with-gas background temperature>without-gas background temperature.

When the gas temperature is lower than the background temperatures indicated by the pixel data for the Jth pixel, the maximum background temperature value becomes the without-gas background temperature and the minimum background temperature value becomes the with-gas background temperature. Meanwhile, when the gas temperature is higher than the background temperatures indicated by the pixel data for the Jth pixel, the maximum background temperature value becomes the with-gas background temperature and the minimum background temperature value becomes the without-gas background temperature. Note that when the detection target gas has room temperature, the air temperature may be used as the gas temperature.

The with-gas background temperature and the without-gas background temperature in step S31 are determined in the above-described manner. Hence, according to the first mode of the present embodiment, the with-gas background temperature and the without-gas background temperature can be measured with one infrared camera 2, without two types of filters and a mechanism for switching between the filters being required. This effect also applies to the rest of the modes (the second through seventh modes of the present embodiment).

The concentration length computation unit 9 functions as the calculation unit (a product calculation unit). The calculation unit calculates the concentration length of gas present in the Jth region, by using the with-gas background temperature and the without-gas background temperature having been determined in step S31 (step S32). Here, the gas concentration length is calculated by using the with-gas background temperature and the without-gas background temperature of the 1st frame group. Description regarding the methods for calculating the gas concentration length is provided later.

The concentration length computation unit 9 functions as the second determination unit. The second determination unit regards the gas concentration lengths for the respective ones of the plurality of frame groups, the gas concentration lengths for the plurality of frame groups having been calculated by the calculation unit, as candidate values, and determines a gas concentration length from among the candidate values. In other words, the second determination unit determines a gas concentration length from among the gas concentration lengths for the respective ones of the plurality of frame groups, the gas concentration lengths for the plurality of frame groups having been calculated by the calculation unit. The estimation unit is provided as a subordinate concept of the second determination unit. The estimation unit regards the gas concentration lengths for the respective ones of the plurality of frame groups, the gas concentration lengths for the plurality of frame groups having been calculated by the calculation unit, as candidate values, and determines the maximum candidate value among the candidate values as an estimate value of the gas concentration length. In the present embodiment, description is provided taking the estimation unit as an example.

The concentration length computation unit 9 functions as the estimation unit. The estimation unit compares the gas concentration length having been calculated in step S32 and a candidate value, and stores therein the greater one of the values as a candidate value (step S33). As described later, the estimation unit determines the candidate value stored therein in the end (i.e., the maximum candidate value) as the estimate value of the concentration length of the gas having leaked. The gas concentration length calculated by using a frame group for which the difference between the with-gas background temperature and the without-gas background temperature is greatest due to a large swaying of gas becomes the maximum candidate value, and the estimation unit determines this value as the estimate value. The initial candidate value is zero. Hence, the estimation unit stores therein, as a candidate value, the gas concentration length having been calculated in step S32, or in other words, the gas concentration length having been calculated by using the with-gas background temperature and the without-gas background temperature of the 1st frame group.

The estimation unit determines whether the frame of interest is the final frame of interest (step S34). When the number of frames is 300, for example, the 280th frame is the final frame of interest. This is because, when the 280th frame is the frame of interest, the frame group (the final frame group) is constituted of the 260th to 300th frames.

When the estimation unit determines that the frame of interest is not the final frame of interest (No in step S34), processing returns to step S31. The first determination unit creates the next frame group by shifting the frame of interest by one frame in chronological order. Here, the frame group when the frame of interest is the 22nd frame is created. This frame group is the 2nd frame group, and is constituted of the 2nd to 42nd frames.

The concentration length computation unit 9 functions as the first determination unit. The first determination unit determines the with-gas background temperature and the without-gas background temperature from among background temperatures indicated by pieces of pixel data, in the chronological pixel data for the Jth pixel, that are included in the 2nd frame group (step S31).

The concentration length computation unit 9 functions as the calculation unit. The calculation unit calculates the concentration length of gas present in the Jth background, by using the maximum and minimum background temperature values having been determined in step S31 (step S32). Here, the gas concentration length is calculated by using the with-gas background temperature and the without-gas background temperature of the 2nd frame group.

The concentration length computation unit 9 functions as the estimation unit. The estimation unit compares the gas concentration length having been calculated in step S32 and a candidate value, and stores the greater one of the values as a candidate value. Here, comparison is performed between the gas concentration length having been calculated by using the with-gas background temperature and the without-gas background temperature of the 2nd frame group, and a candidate value (the gas concentration length having been calculated by using the with-gas background temperature and the without-gas background temperature of the 1st frame group). Hence, the maximum gas concentration length among the gas concentration lengths having been computed to this point becomes the gas concentration length stored as a candidate value.

The concentration length computation unit 9 repeats the processing from step S31 to step S33 until it is determined that the frame of interest is the final frame of interest (Yes in step S34). This means that the first determination unit prepares a plurality of frame groups having different combinations of frames, and determines the with-gas background temperature and the without-gas background temperature for each of the plurality of frame groups. For each of the plurality of frame groups, the calculation unit calculates the gas concentration length by using the with-gas background temperature and the without-gas background temperature having been determined by the first determination unit.

When determining that the frame of interest is the final frame of interest (Yes in step S34), the estimation unit assumes that the candidate value stored thereto in step S33 is the concentration length of the hanging gas (step S35). Hence, the estimation unit is a subordinate concept of the second determination unit, and sets the maximum gas concentration length among the gas concentration lengths for the respective ones of the plurality of frame groups, the gas concentration lengths for the plurality of frame groups having been calculated by the calculation unit, as the estimate value of the concentration length of the hanging gas.

A mode in which the concentration length computation unit 9 does not have the function of the estimation unit may also be made. In other words, a mode may be made in which the concentration length computation unit 9, rather than calculating the estimate value of the gas concentration length, calculates the instantaneous value of the gas concentration length. In this mode, step S33 and step S35 are unnecessary, and the gas concentration lengths of the respective ones of the plurality of frame groups become instantaneous values, the gas concentration lengths for the plurality of frame groups having been calculated in step S32.

FIG. 10 is an image diagram showing a transition of infrared images displayed on the display unit 11 during execution of the first mode of the present embodiment. These infrared images have been yielded by taking a moving image of the testing site described in FIG. 3 by using the infrared camera 2.

The portions inside the frames indicated by dotted lines are infrared images. The infrared images are constituted of the pixel of interest (the Jth pixel) and pixels located in the periphery thereof. The pixels each correspond to a value yielded by multiplying the gas concentration length having been calculated in step S32 by one hundred. The processing from step S31 to step S35 has been performed with respect to these pixels.

Gas concentration is indicated by using the lower explosive limit (LEL). The lower explosive limit is the minimum concentration at which flammable gas mixed with air explodes when ignited. 100% LEL indicates that the lower explosive limit has been reached. In the case of methane gas, 100% LEL corresponds to when the concentration thereof reaches 5%. Gas concentration lengths are indicated by using the unit LELm. Here, m indicates the distance in the depth-direction.

The gas concentration length calculated in step S32 is indicated by "ct", and the candidate value in step S33 (the maximum gas concentration length calculated so far) is indicated by "ct max". As described above, the processing from step S31 to step S35 has been performed with respect to all pixels in the portions of the frames indicated by dotted lines. However, "ct" and "ct max" are values for the pixel of interest.

The infrared image indicated by time point T20 is an infrared image taken immediately after the start of gas emission. Here, ct indicates the gas concentration length having been calculated by using the with-gas background temperature and the without-gas background temperature of the frame group in which the frame of interest is the frame at time point T20.

The infrared image indicated by time point T21 is the infrared image after two seconds have elapsed from time point T20. Here, ct indicates the gas concentration length having been calculated by using the with-gas background temperature and the without-gas background temperature of the frame group in which the frame of interest is the frame at time point T21. At this time point, the concentration length of gas hanging in the region corresponding to the pixel of interest (for example, the Jth region when the pixel of interest is the Jth pixel shown in FIGS. 1 and 2) is relatively low. This means that a relatively small amount of gas is hanging in this region.

The infrared image indicated by time point T22 is the infrared image after five seconds have elapsed from time point T20. Here, ct indicates the gas concentration length having been calculated by using the with-gas background temperature and the without-gas background temperature of the frame group in which the frame of interest is the frame at time point T22. At this time point, the concentration length of gas hanging in the region corresponding to the pixel of interest is relatively high. This means that a relatively large amount of gas is hanging in this region.

The infrared image indicated by time point T23 is the infrared image after eight seconds have elapsed from time point T20. Here, ct indicates the gas concentration length having been calculated by using the with-gas background temperature and the without-gas background temperature of the frame group in which the frame of interest is the frame at time point T23. At this time point, the concentration length of gas hanging in the region corresponding to the pixel of interest is relatively low. This means that a relatively small amount of gas is hanging in this region.

The gas concentration length at time point T22 (3.5% LELm) is determined as the estimate value of the gas concentration length in the region corresponding to the pixel of interest. The exact gas concentration length in this region was 3% LELm. As described above, the with-gas background temperature and the without-gas background temperature can be determined by using the phenomenon of the swaying of leaking gas. The swaying of gas is caused by wind, etc. Hence, the temperature difference between the with-gas background temperature and the without-gas background temperature fluctuates along the time axis, and as a result, the concentration length also fluctuates along the time axis. Due to this, errors in the values of the with-gas background temperature and without-gas background temperature are produced unavoidably, and as a result, errors in the gas concentration length are also produced. In the present embodiment, the maximum concentration length along the time axis is determined as the estimate value of the concentration length, and this estimate value is regarded as the concentration length. According to experimentation, it has been observed that the estimate value falls within the range of 0.5 times to twice the exact gas concentration length.

Here, description is provided of the reason why the predetermined number of frames has been set to 41 frames. In the present embodiment, the gas concentration length in the Jth region shown in FIGS. 1 and 2 (the region corresponding to the pixel of interest), for example, in each frame group is calculated, and the maximum gas concentration length among the gas concentration lengths is determined as the estimate value of the gas concentration length. When a state in which gas is present in the Jth region or a state in which gas is not present in the Jth region continues over the entire period of a given frame group, the gas concentration length for the frame group cannot be calculated. In order to calculate the gas concentration length, it is required that in the Jth region, the state in which gas is present and the state in which gas is not present occur during the period of one frame group.

It can be ensured that in the Jth region, the state in which gas is present and the state in which gas is not present certainly occur by extending the period of one frame group. However, the background temperature changes when a cloud moves and blocks sunlight or when a cloud blocking sunlight moves. The possibility of being affected by this increases when the period of one frame group is set excessively long. Meanwhile, if the period of one frame group is set excessively short, it is unlikely that in the Jth region, both the state in which gas is present and the state in which gas is not present occur.

Hence, the period of one frame group is set from such viewpoints, and the inventors of the present invention have set the period of one frame group to 1.4 seconds. Because the frame rate of moving images taken by the infrared camera 2 is 30 fps, the predetermined number of frames has been set to 41 frames. This is because, while the exact number of frames is 42 frames, the number of frames before the frame of interest (20, in this case) and the number of frames after the frame of interest (20, in this case) cannot be equalized unless an odd number is set. The predetermined number of frames changes when the frame rate changes.

The period of one frame group has been set to 1.4 seconds. This, however, can be set as appropriate in accordance with the wind velocity at the site where the gas leakage monitoring target is located, etc. When the wind velocity is low, for example, the period of one frame group is set to be longer than 1.4 seconds (for example, 3 seconds).

Description is provided of the second mode of the present embodiment. In this mode, the gas concentration length is calculated taking into consideration the case in which there is a rapid and significant change in the background temperature. When a cloud moves and blocks sunlight or when a cloud blocking sunlight moves, the background temperature changes more rapidly and significantly (for example, changes by 4° C.) compared to the temperature change brought about by gas having leaked.

Figure 11:
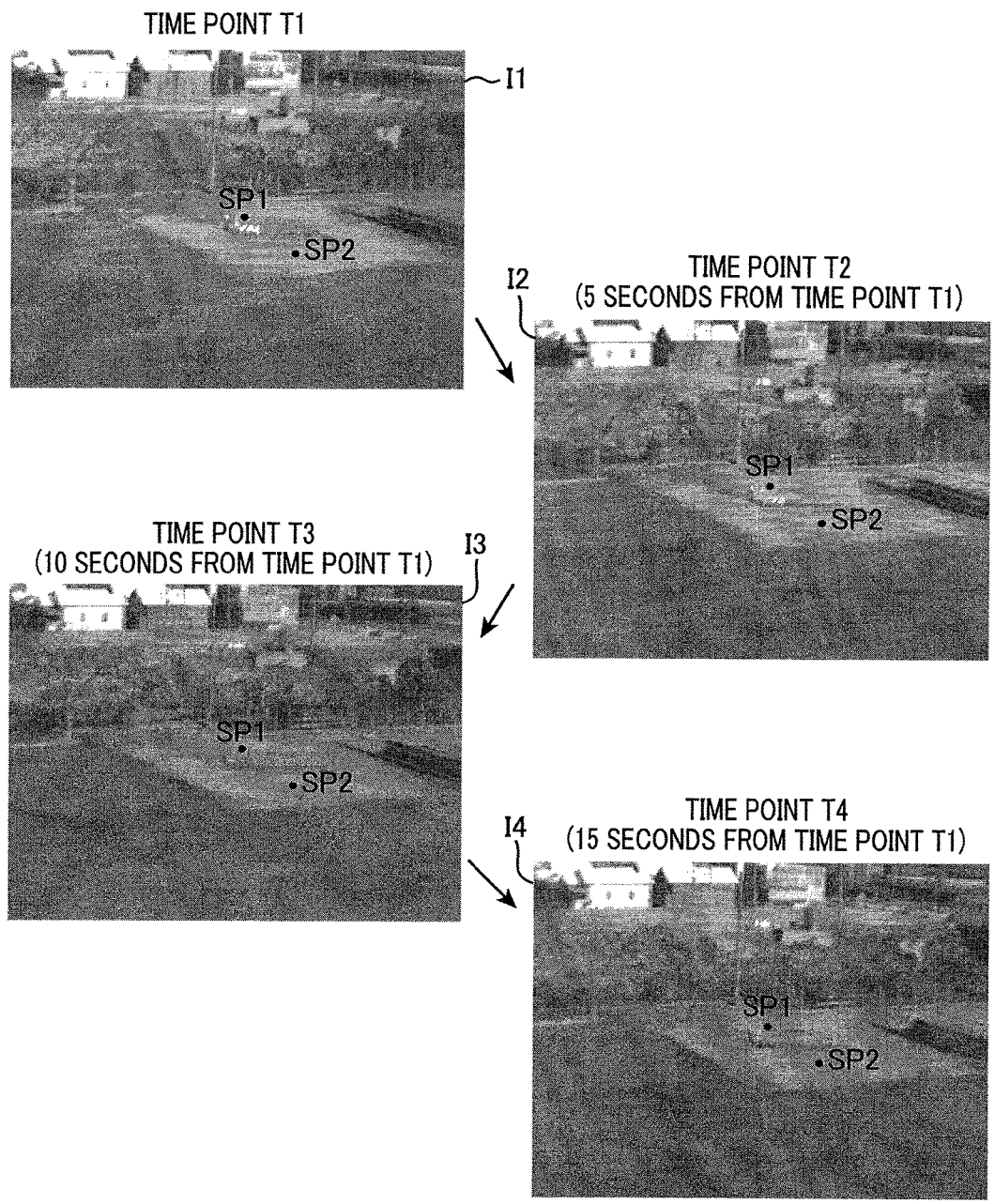
FIG. 11 is an image diagram showing, in chronological order, infrared images of an outdoor testing site taken under a condition in which gas leakage and a temperature change of the background are occurring concurrently.

FIG. 11 is an image diagram showing, in chronological order, infrared images of an outdoor testing site taken under a condition in which gas leakage and a temperature change of the background are occurring concurrently. These infrared images have been yielded by taking a moving image by using the infrared camera 2. At the testing site, there is a spot SP1 capable of causing gas emission. Spot SP2 from which gas is not emitted is shown for comparison with spot SP1.

Image I1 is an infrared image of the testing site taken at time point T1, which is immediately before sunlight is blocked by a cloud. Image I2 is an infrared image of the testing site taken at time point T2, which is five seconds after time point T1. The background temperature is lower at time point T2 compared to at time point T1 because sunlight is being blocked by a cloud.

Image I3 is an infrared image of the testing site taken at time point T3, which is ten seconds after time point T1. The state in which sunlight is blocked by a cloud is continuing from time point T2 to time point T3. Hence, the background temperature is lower at time point T3 compared to at time point T2.

Image I4 is an infrared image of the testing site taken at time point T4, which is fifteen seconds after time point T1. The state in which sunlight is blocked by a cloud is continuing from time point T3 to time point T4. Hence, the background temperature is lower at time point T4 compared to at time point T3.

Background temperature has decreased by approximately 4° C. during the 15 seconds from time point T1 to time point T4. Due to this, image I4 is darker than image I1 on the whole, and it can be observed that the background temperature has decreased.

Gas emission is started at spot SP1 at a time point after time point T1 and before time point T2. The temperature change brought about by the emitted gas is very small (approximately 0.5° C.). Due to this, at time point T2, time point T3, and time point T4, while gas emission is occurring at spot SP1, the temperature change of the background is far greater than the temperature change brought about by the emitted gas, and thus, the state of gas being emitted from spot SP1 cannot be observed in images I2, I3, and I4.

Figure 12A:
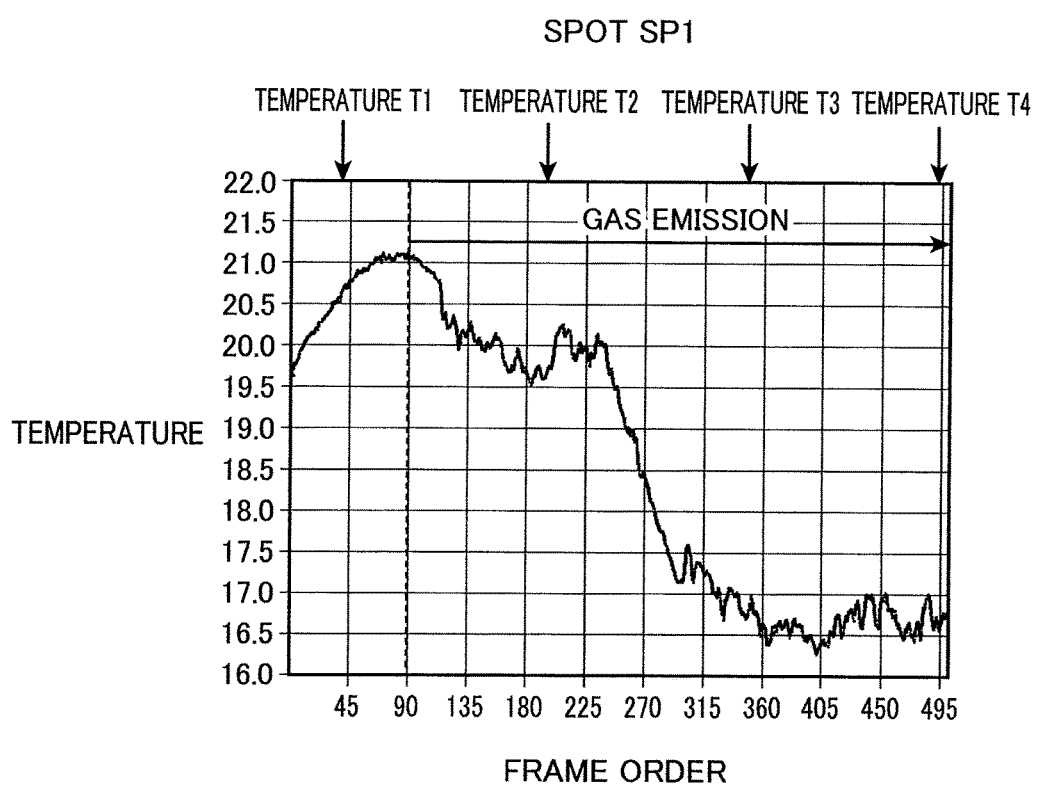
FIG. 12A is a graph showing a temperature change at spot SP1 of the testing site.
Figure 12B:
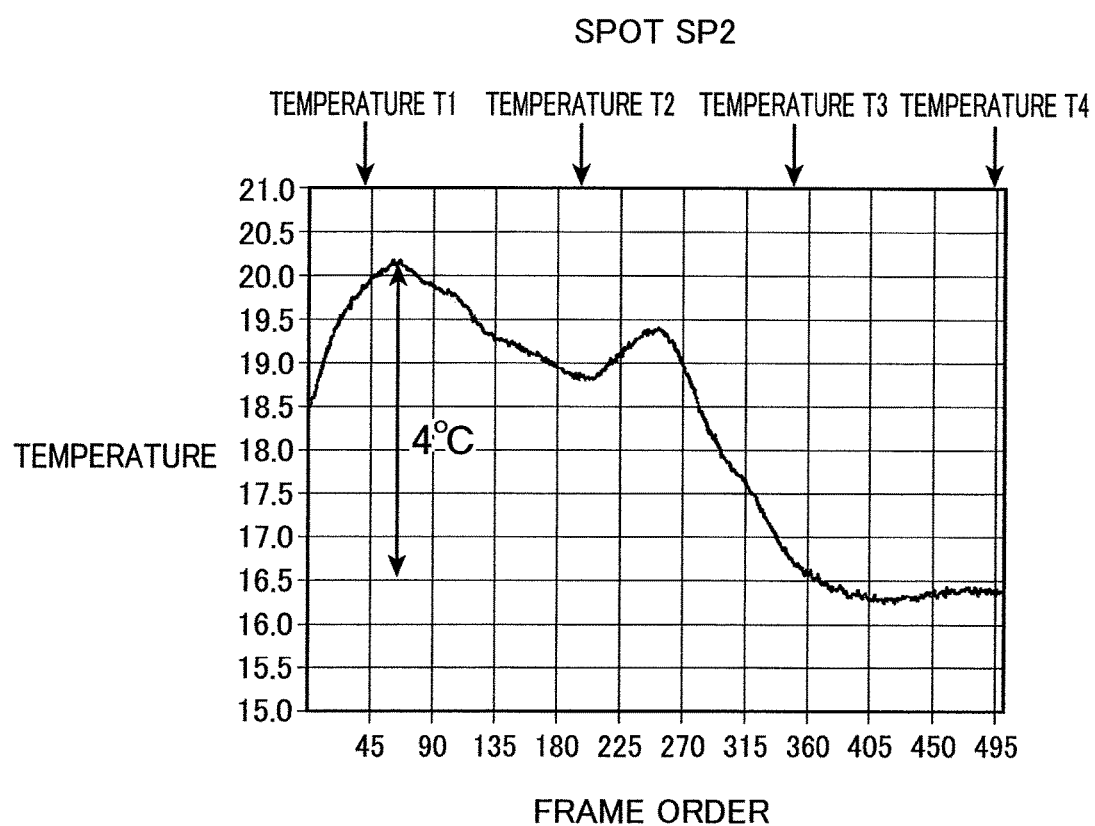
FIG. 12B is a graph showing a temperature change at spot SP2 of the testing site.

FIG. 12A is a graph showing a temperature change at spot SP1 of the testing site, and FIG. 12B is a graph showing a temperature change at spot SP2 of the testing site. The vertical axes of these graphs indicate background temperature. The horizontal axes of these graphs indicate frame order. For example, "45" indicates the 45th frame. The frame rate is 30 fps. Hence, the time from the 1st frame to the 450th frame is 15 seconds.

The graph showing the temperature change at spot SP1 and the graph showing the temperature change at spot SP2 differ. The temperature change at spot SP2 indicates the change in the background temperature because gas emission is not occurring at spot SP2. Meanwhile, gas is hanging at spot SP1 because gas emission is occurring at spot SP1. Due to this, the temperature change at spot SP1 indicates a temperature change yielded by adding the change in the background temperature and the temperature change brought about by gas having leaked.

Figure 13:
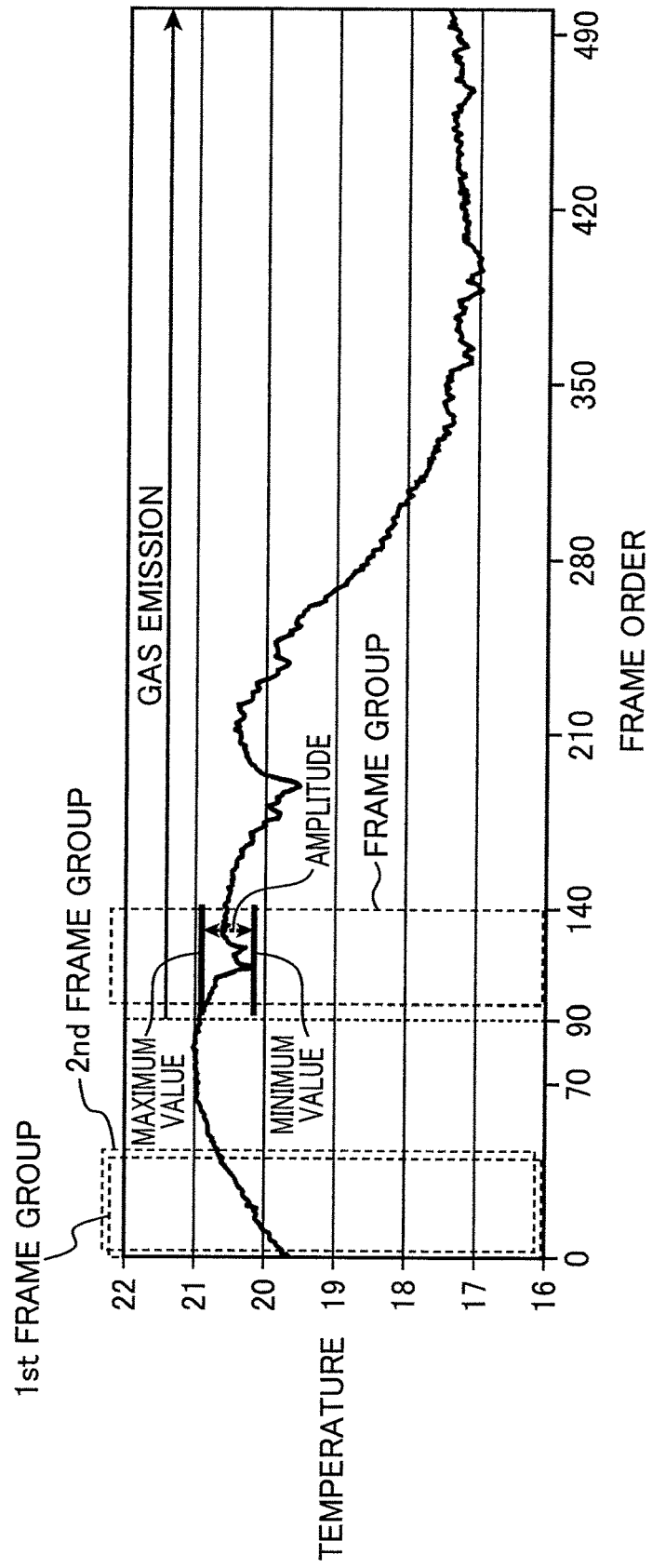
FIG. 13 is a graph showing a relation between frame groups and the temperature change at spot SP1 (FIG. 11) of the testing site.

FIG. 13 is a graph showing a relation between frame groups and the temperature change at spot SP1 of the testing site. The vertical and horizontal axes of the graph are the same as the vertical and horizontal axes of the graph shown in FIG. 4. The line indicating the temperature change is the chronological pixel data for a pixel corresponding to spot SP1. Gas emission is started from around the 90th frame. The graph shows that the temperature change brought about by gas emission and the change in the background temperature are occurring concurrently.

Figure 14:
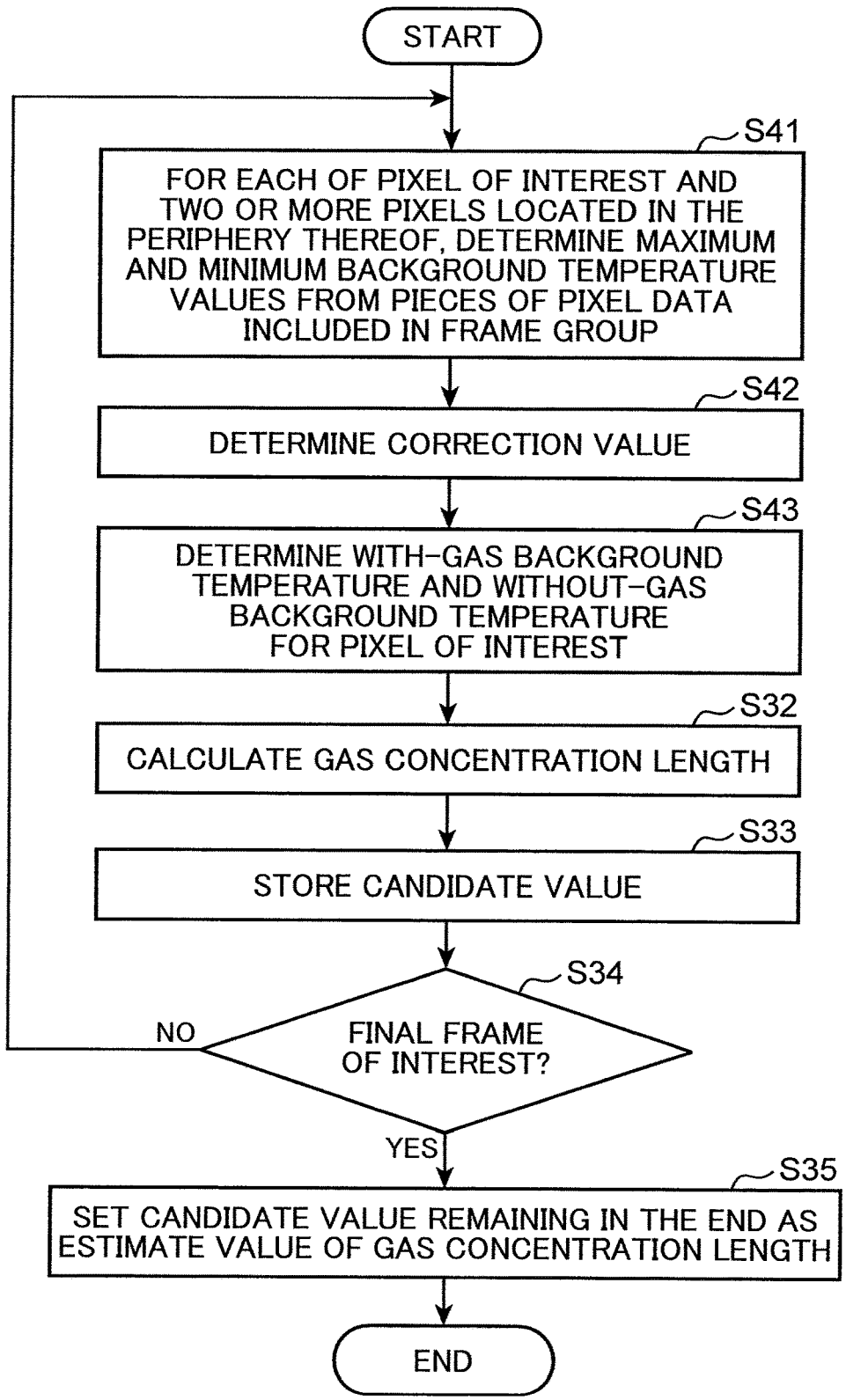
FIG. 14 is a flowchart of processing executed in a second mode of the present embodiment.
Figure 15:
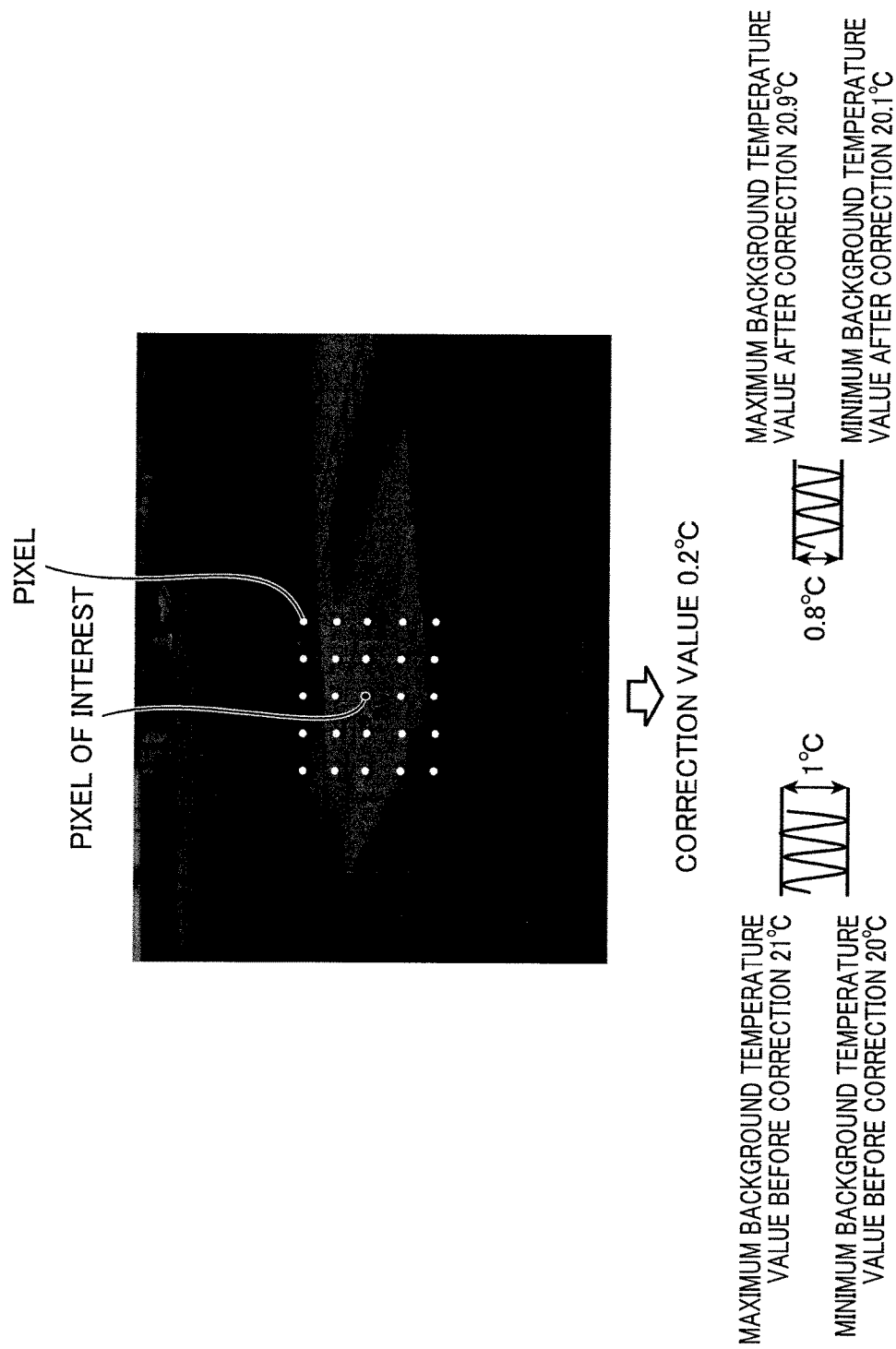
FIG. 15 is an image diagram showing an infrared image displayed on the display unit in the second mode of the present embodiment.

The second mode of the present embodiment calculates the gas concentration length taking into consideration a case in which the temperature change brought about by gas leakage and the change in the background temperature occur concurrently and there is a rapid and significant change in the background temperature. FIG. 14 is a flowchart of processing executed in the second mode of the present embodiment. With reference to FIGS. 5A and 14, the display control unit 10 causes the display unit 11 to display an infrared image of a background including the gas leakage monitoring target. FIG. 15 is an image diagram showing an infrared image displayed on the display unit 11 in the second mode of the present embodiment. An operator operates the input unit 12 and inputs the position of the pixel of interest (one example of the predetermined pixel) in the infrared image displayed on the display unit 11. The pixel of interest is a pixel corresponding to a region in which gas having leaked is hanging. The black dot indicates the pixel of interest. The white dots indicate two or more (24) pixels located in the periphery of the pixel of interest. The pixel of interest and the two or more pixels may be continuous pixels, or other pixels may be present therebetween. The black and white dots are included in the infrared image for convenience in describing these pixels, and are not actually included in the infrared image.

The concentration length computation unit 9 functions as the first determination unit. The first determination unit determines a group of a predetermined number of frames that are consecutive in chronological order as a frame group, the predetermined number of frames being less than the K number of (the plurality of) frames shown in FIG. 6, and in a similar manner as the first mode of the present embodiment, determines the maximum and minimum background temperature values for each of the pixel of interest and the two or more pixels set in advance, which are located in the periphery of the pixel of interest and indicated by the white dots, from among the background temperatures indicated by pieces of the pixel data, in the chronological pixel data for each of the pixel of interest and the two or more pixels, that are included in the frame group (step S41).

Detailed description is provided regarding this point. Chronological pixel data as shown in FIG. 6 is provided for each of the pixel of interest and the two or more pixels. The frame groups are the same as the frame groups of the first mode of the present embodiment. First, the 1st frame group is processed. The first determination unit, in a similar manner as the first mode of the present embodiment, determines the maximum and minimum background temperature values for each of the pixel of interest and the two or more pixels, from among the background temperatures indicated by pieces of the pixel data, in the chronological pixel data for each of the pixel of interest and the two or more pixels, that are included in the frame group.

In the manner described above, the maximum and minimum background temperature values in step S41 are determined for the 1st frame group.

The concentration length computation unit 9 functions as a correction unit. The correction unit corrects the maximum and minimum background temperature values for the pixel of interest (one example of the predetermined pixel) on the basis of the maximum and minimum background temperature values for each of the two or more pixels. Description is provided regarding this correction. First, the correction unit calculates a temperature difference that is the difference between the maximum and minimum background temperature values having been determined in step S41 for each of the two or more pixels, and determines a correction value (step S42). To provide detailed description, the two or more pixels are the 24 pixels indicated by white dots in FIG. 15, and the temperature difference, which is the difference between the maximum and minimum background temperature values that have been determined by the first determination unit, is calculated for each of these pixels. The correction value is a value that is regarded as the amount of change in the background temperature, and may be either a minimum temperature difference that is the smallest among the calculated temperature differences or an average of the calculated temperature differences. The minimum temperature difference is such that, when the temperature difference for the top left pixel, for example, among the 24 pixels indicated by white dots in FIG. 15 is smallest, this temperature difference becomes the minimum temperature difference. The average is a value yielded by averaging the temperature differences for the 24 pixels. When the background temperature changes, a difference between the maximum and minimum background temperature values occurs even at pixels corresponding to regions (FIGS. 1 and 2) in which gas is not present. This difference becomes a factor that increases the errors of the gas concentration lengths, and thus, the correction value is calculated in step S42.

With reference to FIG. 15, the correction unit then corrects each of the maximum and minimum background temperature values for the pixel of interest (one example of the predetermined pixel), the maximum and minimum background temperature values having been determined in step S41, so that a value yielded by subtracting the correction value (for example, 0.2° C.) from the temperature difference (1° C.) between the maximum background temperature value (for example, 21° C.) and the minimum background temperature value (for example, 20° C.) for the pixel of interest, the maximum and minimum background temperature values having been determined in step S41, becomes the temperature difference (0.8° C.) between the maximum and minimum background temperature values for the pixel of interest. The concentration length computation unit 9 determines the maximum background temperature value after correction as the without-gas background temperature and the minimum background temperature value after correction as the with-gas background temperature when the gas temperature is lower than the background temperatures, and determines the maximum background temperature value after correction as the with-gas background temperature and the minimum background temperature value after correction as the without-gas background temperature when the gas temperature is higher than the background temperatures (step S43). The correction is performed so that the average of the maximum and minimum background temperature values before correction is equal to the average of the maximum and minimum background temperature values after correction.

When an average is used as the correction value, the correction value is a value that takes into consideration the changes in the background temperatures corresponding to the respective ones of the two or more pixels located in the periphery of the pixel of interest. Hence, the maximum and minimum background temperature values for the pixel of interest can be corrected more accurately when an average is used as the correction value, compared to when the minimum temperature difference is used as the correction value.

The concentration length computation unit 9 functions as the calculation unit. The calculation unit calculates the gas concentration length, by using the with-gas background temperature and the without-gas background temperature for the pixel of interest, the with-gas background temperature and the without-gas background temperature having been determined in step S43 (step S32). This step is similar to step S32 shown in FIG. 7.

Processing following this, specifically steps S33, S34, and S35 are the same as the corresponding steps shown in FIG. 7, and description thereof is omitted.

The concentration length computation unit 9 repeats the processing in steps S41, S42, S43, S32, and S33 until it is determined that the frame of interest is the final frame of interest (Yes in step S34). This means that the first determination unit prepares a plurality of frame groups having different combinations of frames, and for each of the plurality of frame groups, determines the maximum and minimum background temperature values for each of the pixel of interest and the two or more pixels (step S41). The correction unit determines the correction value for each of the plurality of frame groups (step S42), and for each of the plurality of frame groups, determines the with-gas background temperature and the without-gas background temperature for the pixel of interest (step S43). The calculation unit calculates the gas concentration length for each of the plurality of frame groups (step S32).

FIG. 16 is an image diagram showing a transition of infrared images displayed on the display unit 11 during execution of each of the first and second modes of the present embodiment. The "with correction" infrared images are infrared images having been processed in the second mode of the present embodiment. The "without correction" infrared images are infrared images having been processed in the first mode of the present embodiment. These image diagrams are similar to the image diagrams shown in FIG. 10. That is, the portions inside the frames are infrared images, and these portions are constituted of the pixel of interest and pixels located in the periphery of the pixel of interest. The pixels each correspond to a value yielded by multiplying the gas concentration length having been calculated in step S32 by one hundred. The pixels indicated by white dots in FIG. 15 are included among the pixels located in the periphery of the pixel of interest. The values "ct" and "ct max" are values for the pixel of interest.

The concentration length of gas included in the 500th frame is determined as the estimate value of the gas concentration length in the region corresponding to the pixel of interest. The estimate value calculated in the second mode (with correction) of the present embodiment was 13.8% LELm, and the estimate value calculated in the first mode (without correction) of the present embodiment was 21.6% LELm. The exact gas concentration length in this region was 8% LELm. Hence, the influence of the change in background temperature can be suppressed in the second mode of the present embodiment than in the first mode of the present embodiment.

As described above, in the second mode of the present embodiment, the gas concentration length is calculated by calculating a correction value by using two or more pixels located in the periphery of the pixel of interest (one example of the predetermined pixel), regarding the correction value as the amount of change in the background temperature, and determining the with-gas background temperature and the without-gas background temperature for the pixel of interest taking the correction value into consideration. Hence, according to the second mode of the present embodiment, even if a rapid and significant change in the background temperature occurs during gas leakage, the influence of the change in the background temperature can be suppressed.

Description is provided of the third mode of the present embodiment. In the first and second modes of the present embodiment, the gas concentration length is calculated for each frame group, considering that the background temperature changes. There is hardly any change in the background temperature when gas detection is performed indoors or during the nighttime. In the third mode of the present embodiment, the gas concentration length is calculated without dividing the entirety of frames (the K number of frames shown in FIG. 6) into frame groups.

Figure 17:
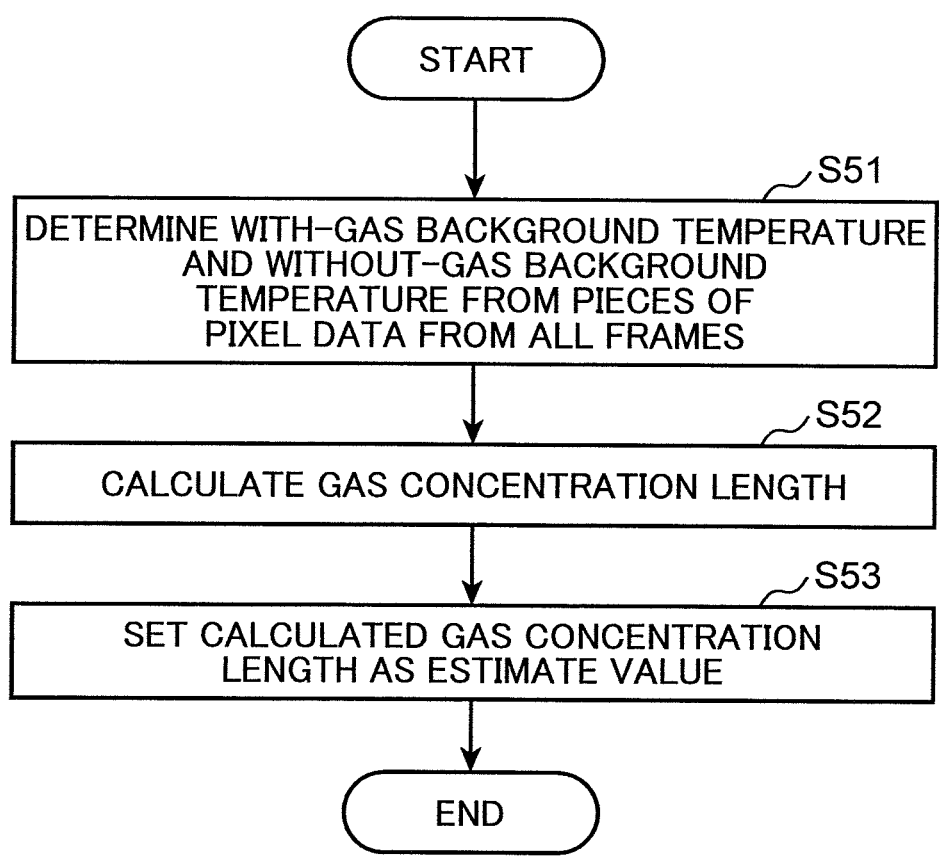
FIG. 17 is a flowchart of processing executed in a third mode of the present embodiment.

FIG. 17 is a flowchart of processing executed in the third mode of the present embodiment. With reference to FIGS. 5A and 17, the display control unit 10 causes the display unit 11 to display an infrared image of a background including the gas leakage monitoring target. An operator operates the input unit 12 and inputs the position of the pixel of interest (one example of the predetermined pixel) in the infrared image displayed on the display unit 11. Up to this point, the third mode is the same as the first mode of the present embodiment.

The concentration length computation unit 9 has the functions of the first determination unit. The first determination unit uses the K number of frames as the entirety of frames, forms the chronological pixel data by using pieces of the pixel data for the pixel of interest from all frames, determines the maximum and minimum background temperature values from among background temperatures indicated by the pixel data included in this chronological pixel data, and determines the maximum and minimum background temperature values as the without-gas background temperature and the with-gas background temperature, respectively, when the gas temperature is lower than the background temperatures indicated by the pixel data for the predetermined pixel (for example, the Jth pixel) and determines the maximum and minimum background temperature values as the with-gas background temperature and the without-gas background temperature, respectively, when the gas temperature is higher than the background temperatures indicated by the pixel data for the predetermined pixel (for example, the Jth pixel) (step S51, FIGS. 9A and 9B).

Figure 18:
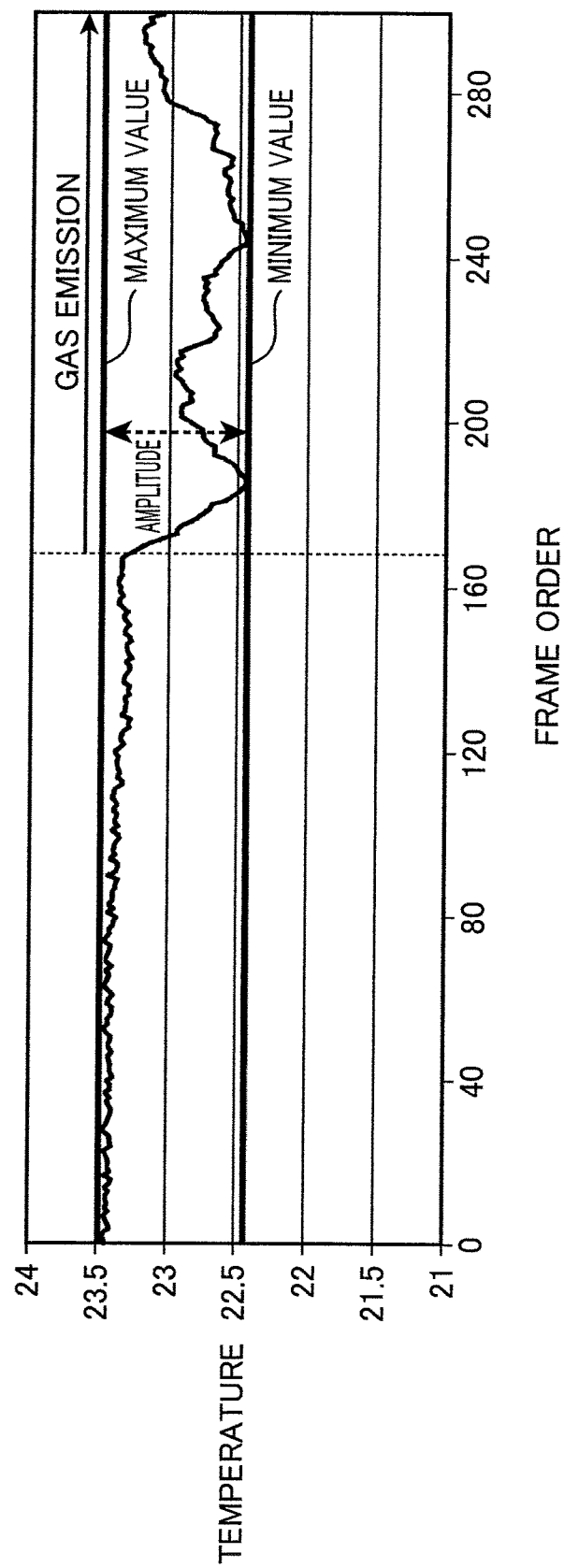
FIG. 18 is a graph showing the temperature change at spot SP4 (FIG. 3) of the testing site.

Description is provided regarding the determination of the maximum and minimum background temperature values. FIG. 18 is a graph indicating the temperature change at spot SP4 of the testing site. The vertical and horizontal axes in the graph are the same as those shown in FIG. 8. In the third mode of the present embodiment, the unit for which the maximum and minimum background temperature values are determined is not each frame group, but rather, is the entirety of frames.

The method for determining the with-gas background temperature and the without-gas background temperature from the maximum and minimum background temperature values is as described on the basis of FIGS. 9A and 9B.

The concentration length computation unit 9 functions as the calculation unit. The calculation unit calculates the gas concentration length by using the with-gas background temperature and the without-gas background temperature having been determined in step S51 (step S52). Description regarding the methods for calculating the gas concentration length is provided later.

The concentration length computation unit 9 functions as the estimation unit. The estimation unit sets the gas concentration length having been calculated in step S52 as the estimate value of the gas concentration length in the region in which gas is hanging (step S53).

With reference to FIGS. 1 and 2, according to the first and second modes of the present embodiment, the with-gas background temperature and the without-gas background temperature cannot be determined when the cycle in which the switch from the state in which gas is present to the state in which gas is not present and the switch from the state in which gas is not present to the state in which gas is present occur in the region (the Jth region) corresponding to the pixel of interest (for example, the Jth pixel) is longer than the period of a frame group. Meanwhile, according to the third mode of the present embodiment, the unit for which the with-gas background temperature and the without-gas background temperature are determined is not each frame group, but rather is the entirety of frames. Due to this, the with-gas background temperature and the without-gas background temperature can be determined even if the above-described cycle is long.

Description is provided of the fourth mode of the present embodiment. It is not necessarily the case that the swaying of leaking gas occurs so that, in the region corresponding to the pixel of interest, the state in which gas is present and the state in which gas is not present occur. Hence, it is not necessarily the case that the estimate value of the gas concentration length in the region corresponding to the pixel of interest indicates the correct gas concentration length. The fourth mode of the present embodiment also takes into consideration the estimate value of the gas concentration lengths in regions corresponding to pixels located in the periphery of the pixel of interest.

Figure 19:
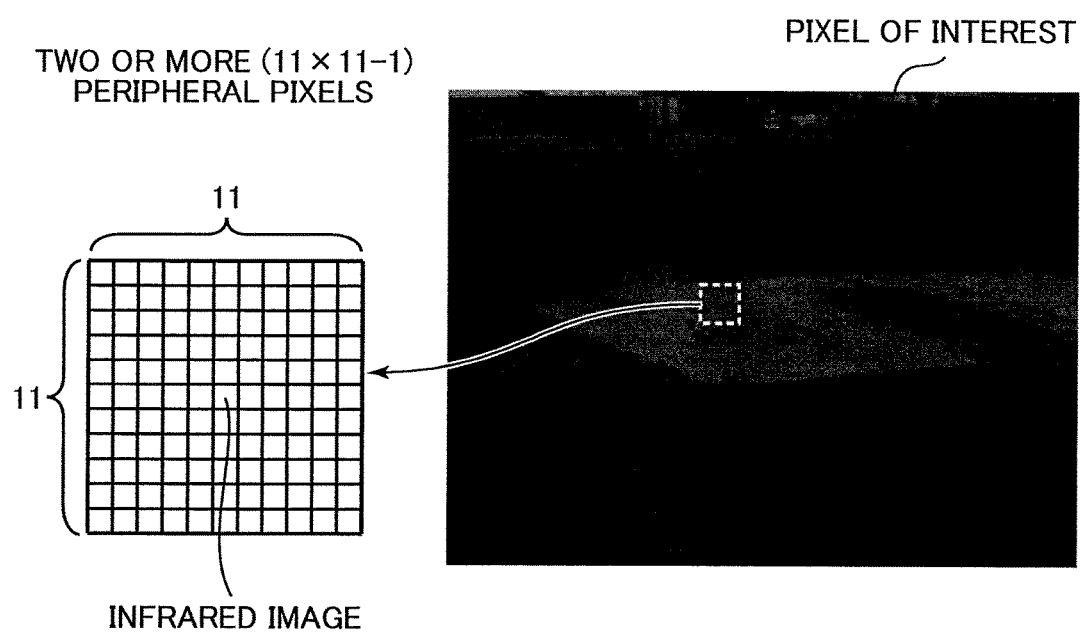
FIG. 19 is an explanatory diagram describing a pixel of interest and peripheral pixels, the pixel of interest and the peripheral pixels relating to a fourth mode of the present embodiment.

FIG. 19 is an explanatory diagram describing the pixel of interest and peripheral pixels relating to the fourth mode of the present embodiment. A pixel set in advance that is located in the periphery of the pixel of interest is regarded as a peripheral pixel, and two or more peripheral pixels are set in advance. In FIG. 19, among 11×11 pixels centered around the pixel of interest in an infrared image, the pixels other than the pixel of interest are regarded as the peripheral pixels.

The concentration length computation unit 9 functions as the first determination unit. The first determination unit, similarly to the first determination unit described in the first mode of the present embodiment, determines each of the pixel of interest and the two or more peripheral pixels as the predetermined pixel, and determines the with-gas background temperature and the without-gas background temperature for each of the pixel of interest and the two or more peripheral pixels.

The concentration length computation unit 9 functions as the calculation unit. The calculation unit, similarly to the calculation unit described in the first mode of the present embodiment, calculates gas concentration lengths for each of the pixel of interest and the two or more peripheral pixels.

The concentration length computation unit 9 functions as the second determination unit. The second determination unit regards the gas concentration lengths for each of the pixel of interest and the two or more peripheral pixels as candidate values, the gas concentration lengths for each of the pixel of interest and the two or more peripheral pixels having been calculated by the calculation unit, and determines a gas concentration length from among the candidate values. The estimation unit is provided as a subordinate concept of the second determination unit. The estimation unit calculates the estimate value of the gas concentration length for each of the pixel of interest and the two or more peripheral pixels, regards the estimate values as candidate values, and determines the maximum candidate value among the candidate values as an estimate value of the gas concentration length. In the present embodiment, description is provided taking the estimation unit as an example.

For each of the pixel of interest and the two or more peripheral pixels, the estimation unit calculates the estimate value of the gas concentration length by using the processing shown in either the flowchart in FIG. 7 relating to the first mode of the present embodiment, the flowchart in FIG. 14 relating to the second mode of the present embodiment, or the flowchart in FIG. 17 relating to the third mode of the present embodiment. The estimation unit sets the greatest estimate value among the estimate values so calculated (the 11×11 estimate values) as the estimate value of the gas concentration length. An assumption is made that the state in which gas is present and the state in which gas is not present have occurred in the region corresponding to the pixel for which estimate value is greatest.

Note that there is a possibility that one of the estimate values among the calculated estimate values (the 11×11 estimate values) becomes extremely great due to noise (dot noise) in a sensor pixel of the two-dimensional image sensor 6 (FIG. 5A), etc. In view of this, the estimation unit may process the calculated estimate values (the 11×11 estimate values) by using a median filter (for example, 3×3 pixels), and set the greatest estimate value among the processed estimate values (the 11×11 estimate values) as the estimate value of the gas concentration length.

Description is provided of the fifth mode of the present embodiment. In the first through fourth modes of the present embodiment, the predetermined pixel (the pixel of interest) is determined by an operator. Meanwhile, in the fifth mode, the gas concentration length measurement device 3 determines the predetermined pixel. Specifically, a pixel corresponding to a region in which gas is hanging, the region detected by the gas concentration length measurement device 3, is set as the predetermined pixel.

In the fifth mode of the present embodiment, the image processing unit 8 shown in FIG. 5A functions as a detection unit. The detection unit detects gas by using the chronological pixel data (the infrared images). Detailed description is provided regarding this point. With reference to FIGS. 11 and 12A, when the temperature change in the background is far greater than the temperature change brought about by emitted gas (gas having leaked), the state of gas coming out from spot SP1 cannot be observed in images I2, I3, and I4 shown in FIG. 11 (it can be observed that gas is being emitting from spot SP1 from the graph shown in FIG. 12A), as already described in the second mode of the present embodiment.

The reason for this is because the moving image data D1 (FIG. 3) includes, in addition to first frequency component data indicating the temperature change brought about by gas having leaked, second frequency component data that has lower frequency than that of the first frequency component data and indicates the change in the background temperature. The image represented by the first frequency component data becomes impossible to see because of the image (the change in light and shade of the background) represented by the second frequency component data. With reference to FIG. 12A, the small changes included in the graph showing the temperature change at spot SP1 correspond to the first frequency component data. The graph showing the temperature change at spot SP2 corresponds to the second frequency component data.

In view of this, the image processing unit 8 (FIG. 5A) performs processing for removing the second frequency component data, with respect to each of a plurality of pieces of chronological pixel data associated with different pixel positions (that is, the plurality of pieces of chronological pixel data constituting the moving image data D1). With reference to FIG. 6, the plurality of pieces of chronological pixel data associated with different pixel positions refer to the chronological pixel data for the 1st pixel, the chronological pixel data for the 2nd pixel, . . . , the chronological pixel data for the (M−1)th pixel, and the chronological pixel data for the Mth pixel.

Frequency component data that has higher frequency than that of the first frequency component data and indicates high frequency noise is referred to as third frequency component data. In addition to processing for removing the second frequency component data, the image processing unit 8 performs processing for removing the third frequency component data, with respect to each of the plurality of pieces of chronological pixel data constituting the moving image data D1.

Hence, the unit in which the image processing unit 8 performs processing for removing the second frequency component data and the third frequency component data is not each frame, and rather, is each piece of chronological pixel data.

Figure 20:
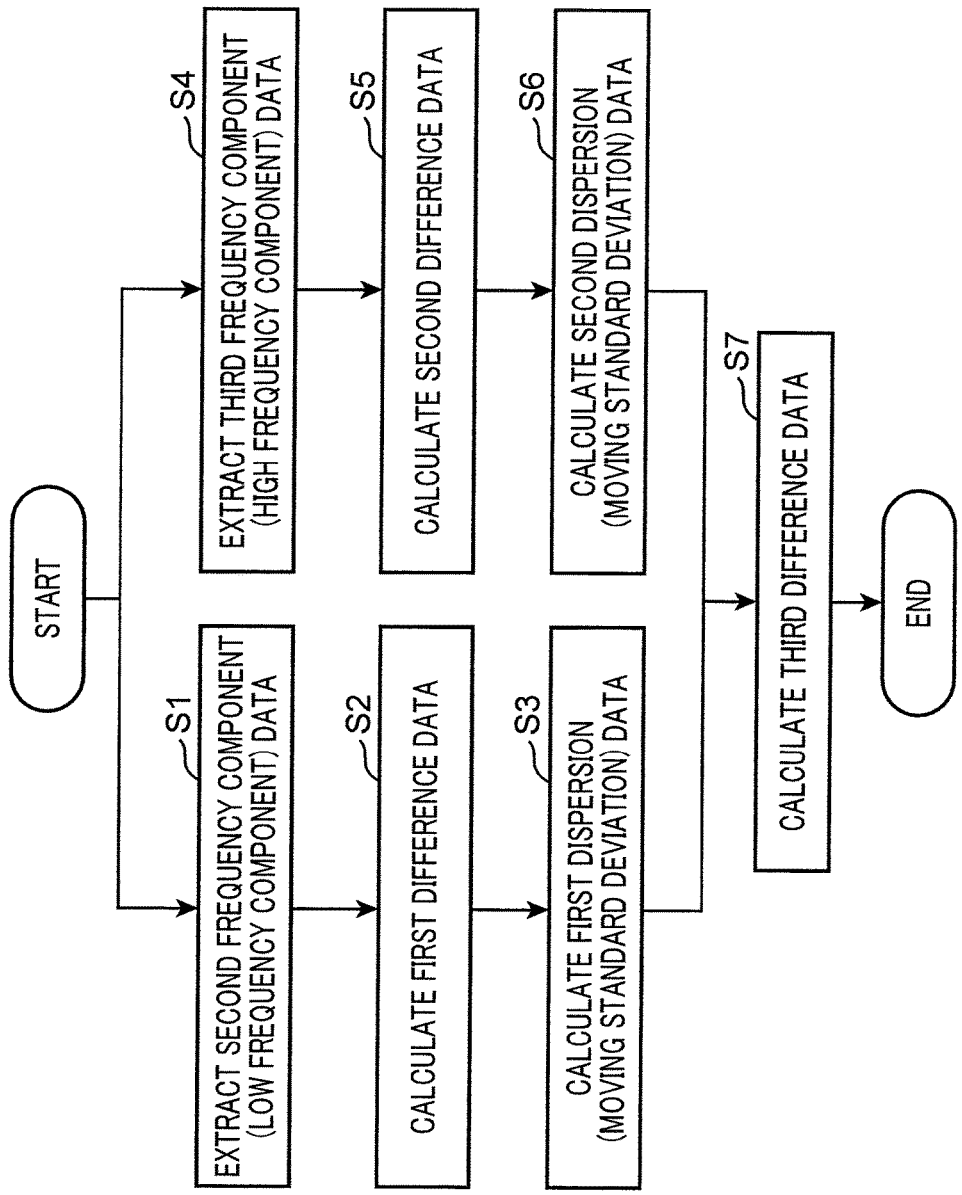
FIG. 20 is a flowchart of processing executed by an image processing unit included in a fifth mode of the present embodiment.

FIG. 20 is a flowchart of processing executed by the image processing unit 8 included in the fifth mode of the present embodiment. The image processing unit 8 functions as a first extraction unit. The first extraction unit extracts, as second frequency component data, data extracted from first chronological pixel data by calculating a simple moving average (first predetermined processing) in units of a first predetermined number of frames that is less than the K number of frames shown in FIG. 6 with respect to the first chronological pixel data, and extracts M pieces of second frequency component data respectively corresponding to the M pieces of chronological pixel data shown in FIG. 6 (step S1).

The first predetermined number of frames, for example, is 21 frames. The 21 frames can be classified into a target frame, ten consecutive frames before the target frame, and ten consecutive frames after the target frame. The first predetermined number of frames may be any number of frames with which second frequency component data can be extracted from chronological pixel data, and is not limited to 21 and may be more or less than 21.

The image processing unit 8 functions as a second extraction unit. The second extraction unit extracts, as third frequency component data, data extracted from the first chronological pixel data by calculating a simple moving average (second predetermined processing) in units of a third predetermined number of (for example, 3) frames that is less than the first predetermined number (for example, 21) with respect to the first chronological pixel data, and extracts M pieces of third frequency component data respectively corresponding to the M pieces of chronological pixel data shown in FIG. 6 (step S4).

Figure 21:
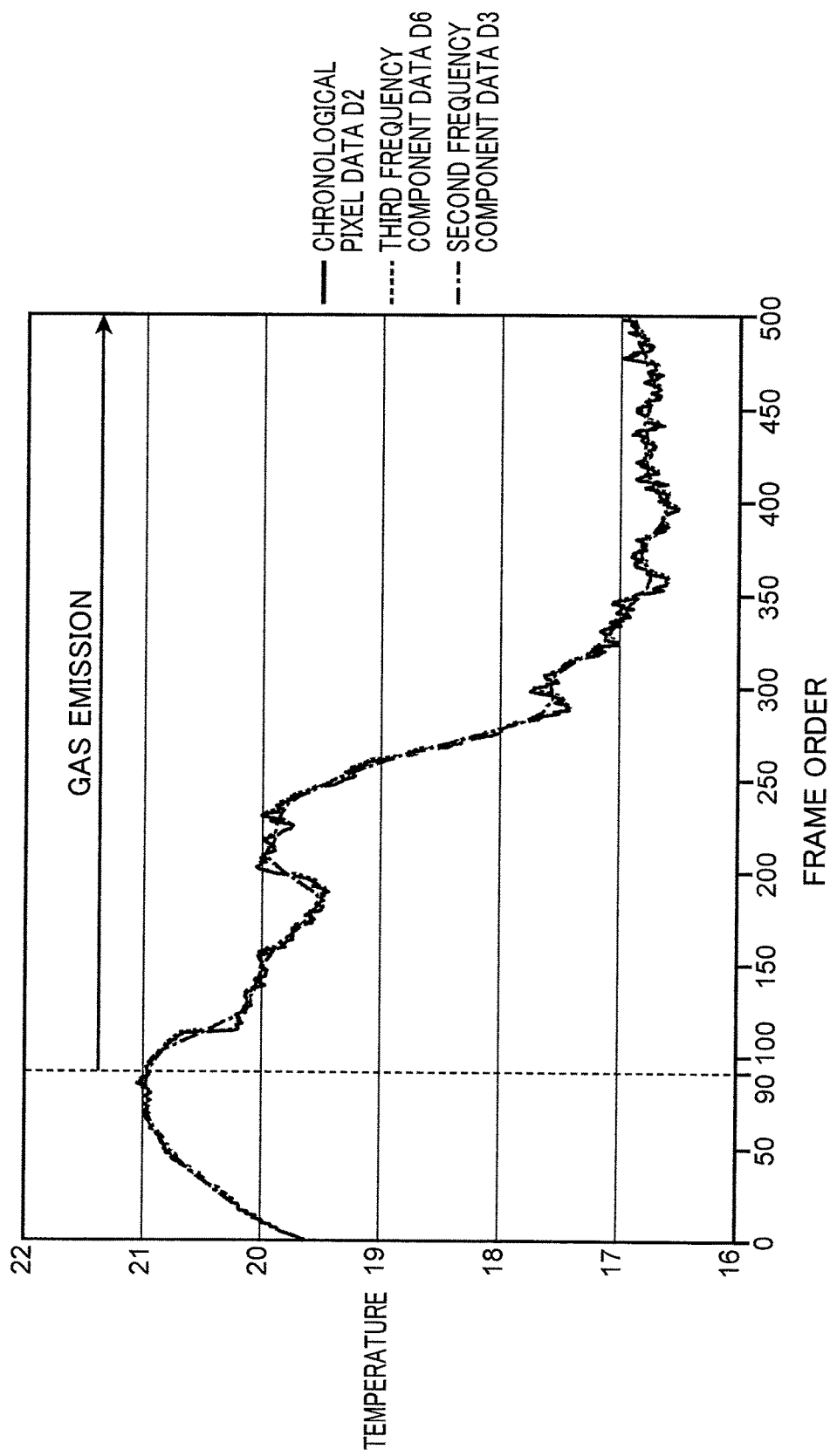
FIG. 21 is a graph showing chronological pixel data D2 for a pixel corresponding to spot SP1 (FIG. 11), second frequency component data D3 extracted from the chronological pixel data D2, and third frequency component data D6 extracted from the chronological pixel data D2.

FIG. 21 is a graph showing chronological pixel data D2 for the pixel corresponding to spot SP1 (FIG. 11), second frequency component data D3 extracted from the chronological pixel data D2, and third frequency component data D6 extracted from the chronological pixel data D2. The vertical and horizontal axes of the graph are the same as the vertical and horizontal axes of the graph shown in FIG. 4. The temperature indicated by the chronological pixel data D2 changes relatively quickly (the cycle of change is relatively short), and the temperature indicated by the second frequency component data D3 changes relatively moderately (the cycle of change is relatively long). The third frequency component data D6 and the chronological pixel data D2 appear to be almost overlapping with one another due to differing in terms of only high frequency components.

The third predetermined number of frames, for example, is 3 frames. The 3 frames can be classified into a target frame, one frame immediately before the target frame, and one frame immediately after the target frame. The third predetermined number of frames may be any number of frames with which third frequency component data can be extracted from chronological pixel data, and is not limited to 3 and may be more than 3.

The image processing unit 8 functions as a first calculation unit. The first calculation unit calculates, as first difference data, data acquired by calculating a difference between the first chronological pixel data and the second frequency component data extracted from the first chronological pixel data, and calculates M pieces of first difference data respectively corresponding to the M pieces of chronological pixel data (step S2).

The image processing unit 8 functions as a third calculation unit. The third calculation unit calculates, as second difference data, data acquired by calculating a difference between the first chronological pixel data and the third frequency component data extracted from the first chronological pixel data, and calculates M pieces of second difference data respectively corresponding to the M pieces of chronological pixel data (step S5).

Figure 22A:
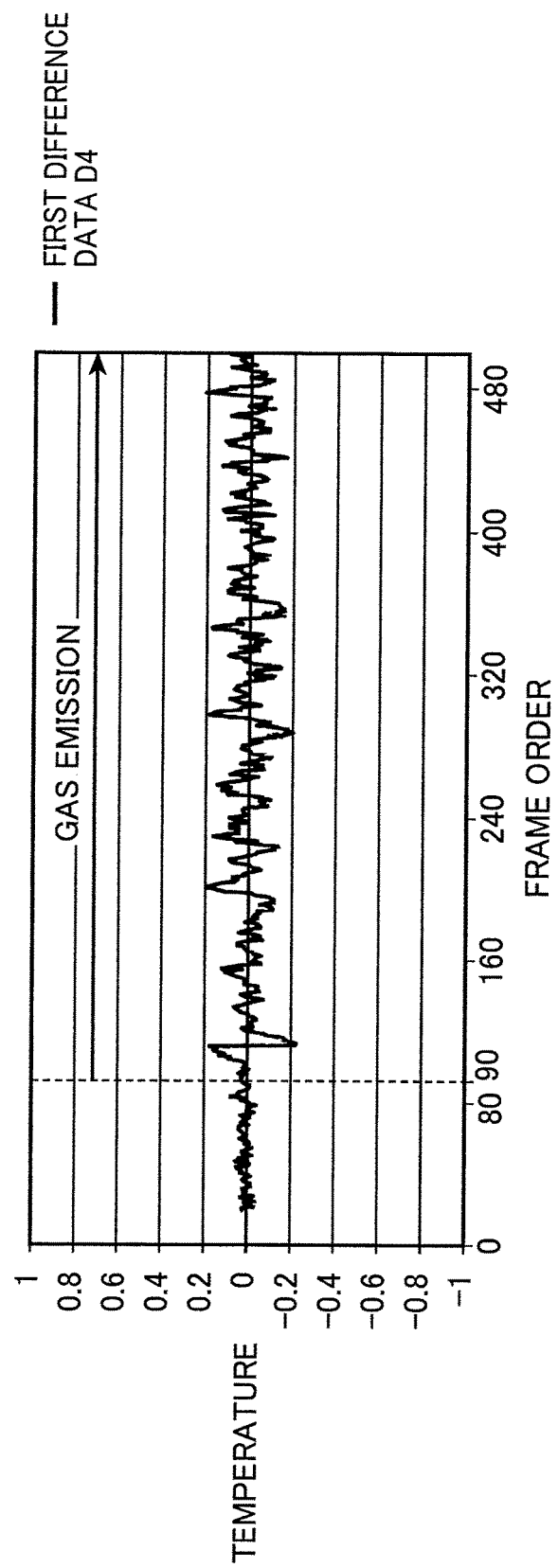
FIG. 22A is a graph showing first difference data D4.
Figure 22B:
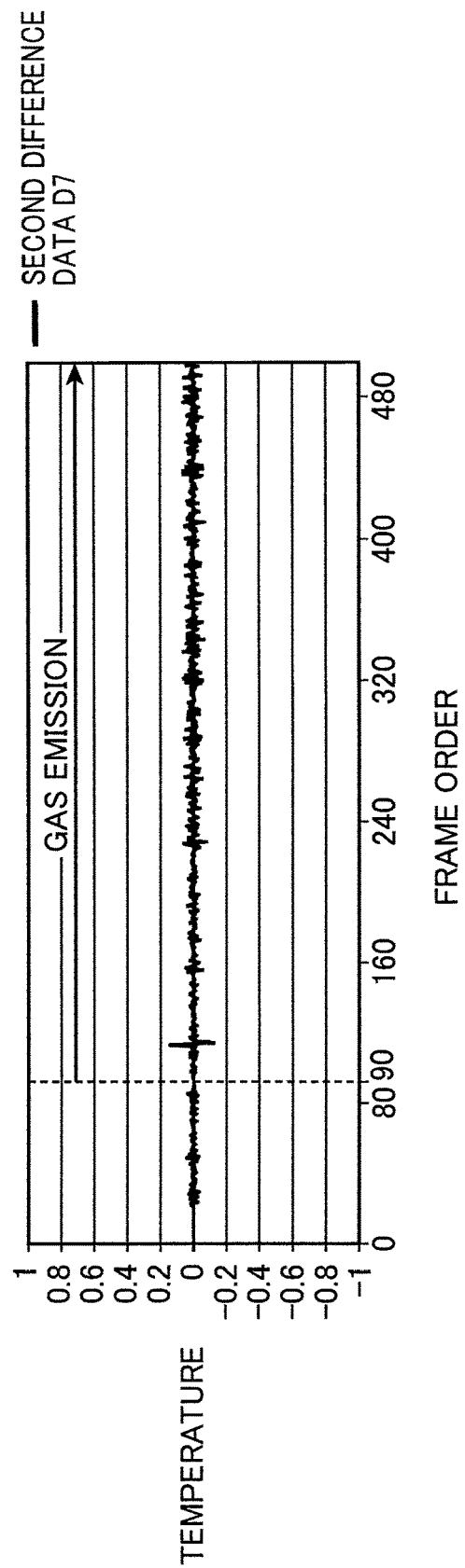
FIG. 22B is a graph showing second difference data D7.

FIG. 22A is a graph showing first difference data D4, and FIG. 22B is a graph showing second difference data D7. The vertical and horizontal axes of the graphs are the same as the vertical and horizontal axes of the graph shown in FIG. 4. The first difference data D4 is data acquired by calculating a difference between the chronological pixel data D2 and the second frequency component data D3, the chronological pixel data D2 and the second frequency component data D3 being shown in FIG. 21. The repetition of minute oscillations indicated by the first difference data D4 before the start of gas emission at spot SP1 in FIG. 11 (up to around the 90th frame) mainly indicates sensor noise of the two-dimensional image sensor 6. The irregularity in amplitude and waveform of the first difference data D4 becomes greater after the start of gas emission at spot SP1 (the 90th frame and on).

The second difference data D7 is data acquired by calculating a difference between the chronological pixel data D2 and the third frequency component data D6, the chronological pixel data D2 and the third frequency component data D6 being shown in FIG. 21.

The first difference data D4 includes the first frequency component data (the data indicating the temperature change brought about by gas having leaked) and the third frequency component data D6 (the data indicating high frequency noise). The second difference data D7 does not include the first frequency component data and includes the third frequency component data D6.

Because the first difference data D4 includes the first frequency component data, the irregularity in amplitude and waveform of the first difference data D4 becomes greater after the start of gas emission at spot SP1 (the 90th frame and on). Meanwhile, this does not apply to the second difference data D7, because the second difference data D7 does not include the first frequency component data. The second difference data D7 repeats minute oscillations. The minute oscillations correspond to high frequency noise.

There is a correlation between the first difference data D4 and the second difference data D7, but the correlation is not complete. That is, there may be cases in which, in a given frame, the value of the first difference data D4 is positive and the value of the second difference data D7 is negative, or vice versa. Hence, the third high frequency component data D6 cannot be removed by calculating a difference between the first difference data D4 and the second difference data D7. In order to remove the third high frequency component data D6, it is necessary to convert the first difference data D4 and the second difference data D7 into absolute values.

In view of this, the image processing unit 8 executes step S3, that is, functions as a second calculation unit that calculates first dispersion data. The second calculation unit calculates, as first dispersion data, data acquired by calculating a moving standard deviation in units of a second predetermined number of frames that is less than the K number of frames with respect to the first difference data, and calculates M pieces of first dispersion data respectively corresponding to the M pieces of chronological pixel data (step S3). Note that a moving variance may be calculated in place of a moving standard deviation.

Further, the image processing unit 8 functions as a fourth calculation unit. The fourth calculation unit calculates, as second dispersion data, data acquired by calculating a moving standard deviation in units of a fourth predetermined number of (for example, 21) frames that is less than the K number of frames with respect to the second difference data, and calculates M pieces of second dispersion data respectively corresponding to the M pieces of chronological pixel data (step S6). Note that a moving variance may be used in place of a moving standard deviation.

Figure 23:
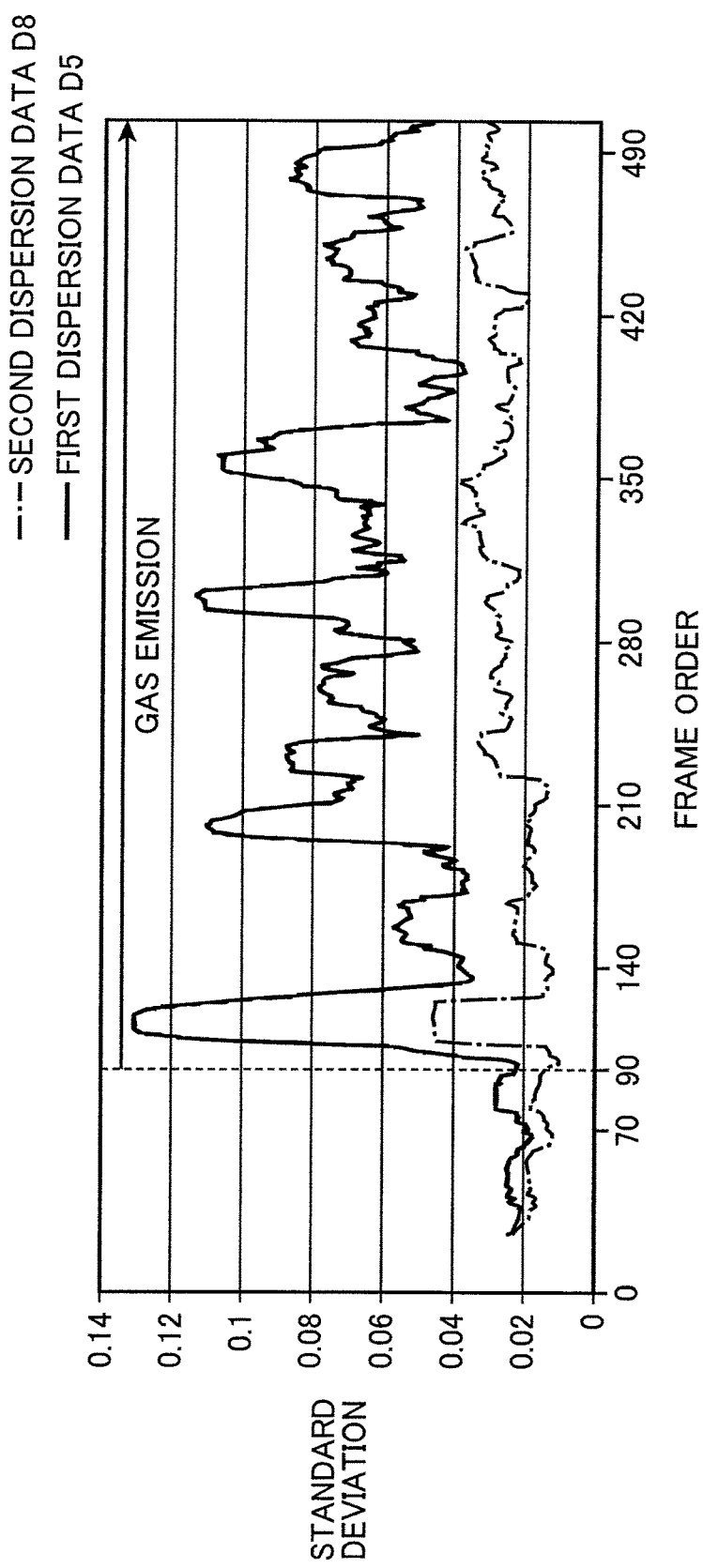
FIG. 23 is a graph showing first dispersion data D5 and second dispersion data D8.

FIG. 23 is a graph showing first dispersion data D5 and second dispersion data D8. The horizontal axis of the graph is the same as the horizontal axis of the graph shown in FIG. 4. The vertical axis of the graph indicates a standard deviation. The first dispersion data D5 is data indicating a moving standard deviation of the first difference data D4 shown in FIG. 22A. The second dispersion data D8 is data indicating a moving standard deviation of the second difference data D7 shown in FIG. 22B. The number of frames used for the calculation of a moving standard deviation is 21 for both the first dispersion data D5 and the second dispersion data D8. However, the number is not limited to 21, as long as a standard deviation that is statistically significant can be calculated by using the number.

Since each of the first dispersion data D5 and the second dispersion data D8 is a standard deviation, the first dispersion data D5 and the second dispersion data D8 do not include negative values. Hence, the first dispersion data D5 and the second dispersion data D8 can be regarded as data yielded by converting the first difference data D4 and the second difference data D7 into absolute values, respectively.

The image processing unit 8 functions as a fifth calculation unit. The fifth calculation unit calculates, as third difference data, data acquired by calculating a difference between the first dispersion data and the second dispersion data that are acquired from the same chronological pixel data, and calculates M pieces of third difference data respectively corresponding to the M pieces of chronological pixel data (step S7).

Figure 24:
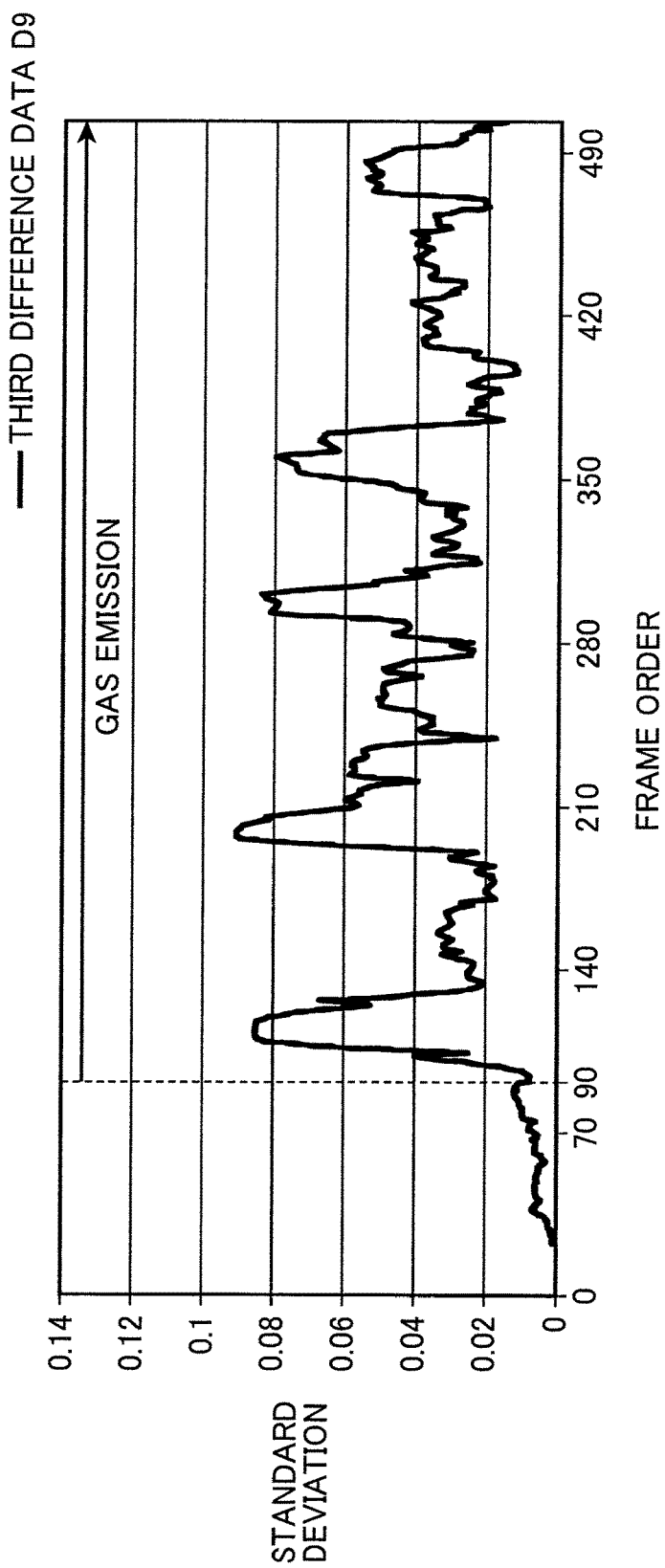
FIG. 24 is a graph showing third difference data D9.

FIG. 24 is a graph showing third difference data D9. The horizontal axis of the graph is the same as the horizontal axis of the graph shown in FIG. 4. The vertical axis of the graph indicates a standard deviation. The third difference data D9 is data indicating a difference between the first dispersion data D5 and the second dispersion data D8, the first dispersion data D5 and the second dispersion data D8 being shown in FIG. 23.

Figure 25:
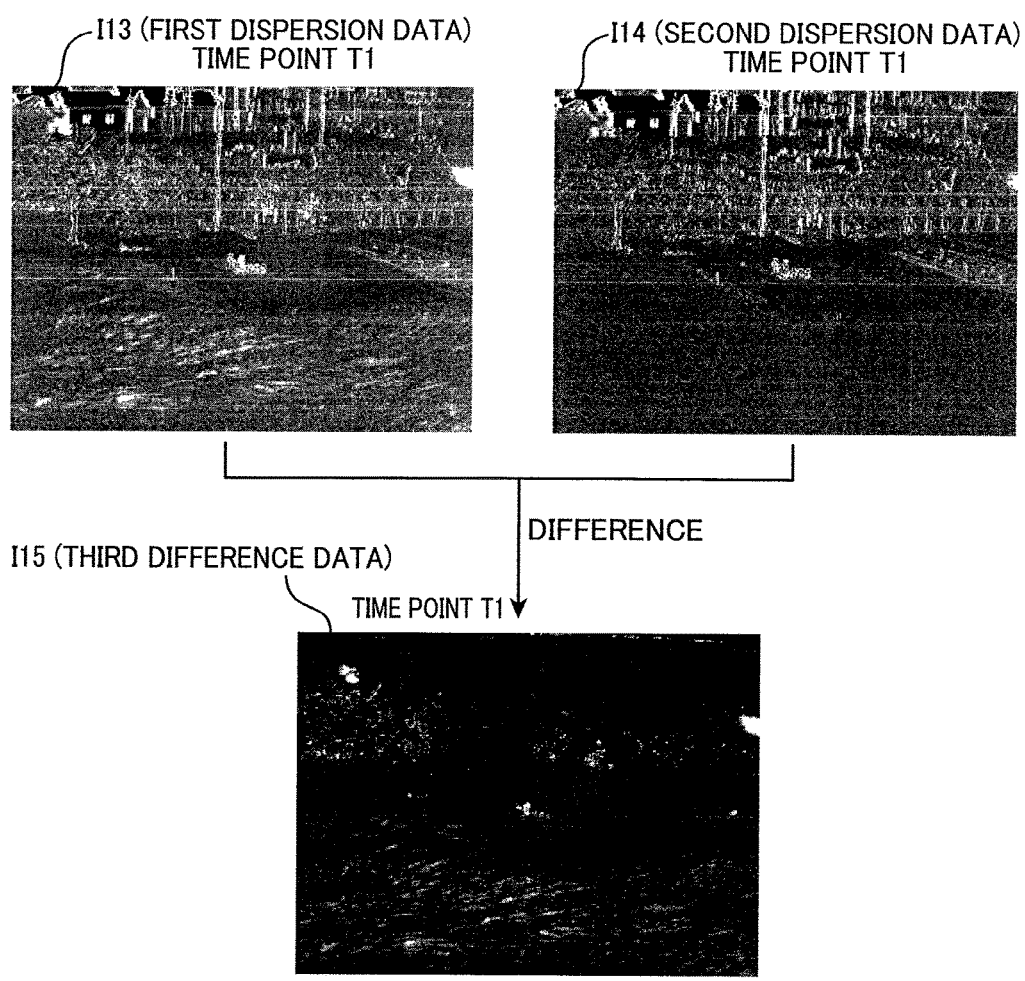
FIG. 25 is an image diagram showing an infrared image I15 of a frame at time point T1, the infrared image I15 having been subjected to image processing by the image processing unit included in the fifth mode of the present embodiment, and infrared images I13 and I14 related to the infrared image I15.
Figure 26:
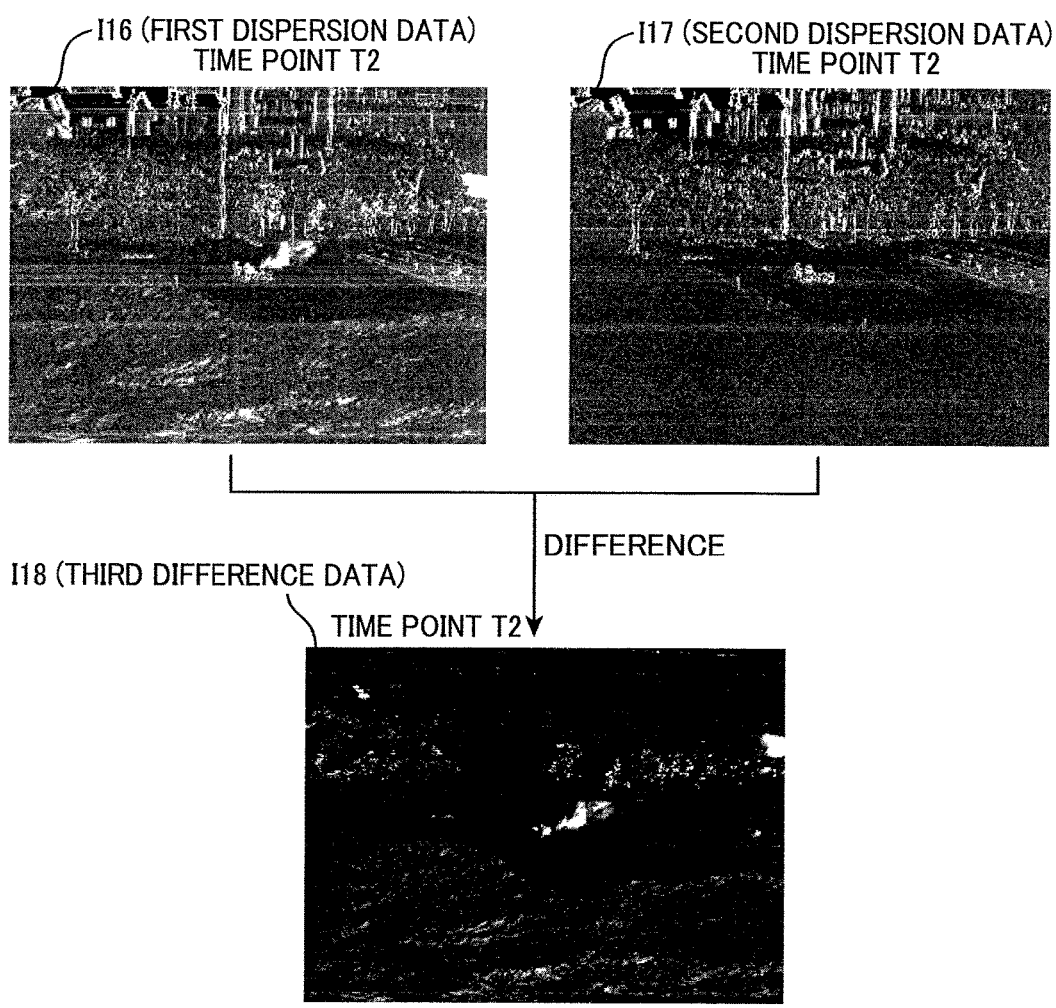
FIG. 26 is an image diagram showing an infrared image I18 of a frame at time point T2, the infrared image I18 having been subjected to the image processing by the image processing unit included in the fifth mode of the present embodiment, and infrared images I16 and I17 related to the infrared image I18.

The display control unit 10 regards the M pieces of third difference data acquired in step S7 as the moving image data D1 having been subjected to processing for removing the second frequency component data and the third frequency component data, and causes the display unit 11 to display a moving image represented by the moving image data D1. An infrared image I15 of a frame at time point T1 and infrared images I13 and I14 related thereto, in this moving image, are shown in FIG. 25, and an infrared image I18 of a frame at time point T2 and infrared images I16 and I17 related thereto, in this moving image, are shown in FIG. 26. The images are each yielded by multiplying a standard deviation by 5000.

FIG. 25 is an image diagram showing an infrared image I15 of a frame at time point T1, the infrared image I15 having been processed by the image processing unit 8, and infrared images I13 and I14 related thereto. The infrared image I13 is an infrared image of the frame at time point T1, in a moving image represented by the M pieces of first dispersion data (moving image data D1) acquired in step S3 of FIG. 20. The infrared image I14 is an infrared image of the frame at time point T1, in a moving image represented by the M pieces of second dispersion data (moving image data D1) acquired in step S6 of FIG. 20. The difference between infrared images I13 and I14 becomes the infrared image I15.

FIG. 26 is an image diagram showing an infrared image I18 of a frame at time point T2, the infrared image I18 having been processed by the image processing unit 8, and infrared images I16 and I17 related thereto. The infrared image I16 is an infrared image of the frame at time point T2, in a moving image represented by the M pieces of first dispersion data (moving image data D1) acquired in step S3. The infrared image I17 is an infrared image of the frame at time point T2, in a moving image represented by the M pieces of second dispersion data (moving image data D1) acquired in step S6. The difference between infrared images I16 and I17 becomes the infrared image I18.

In the infrared image I15 shown in FIG. 25, the state of gas not being emitted from spot SP1 shown in FIG. 11 can be observed, and in the infrared image I18 shown in FIG. 26, the state of gas being emitted from spot SP1 can be observed.

As description has been provided up to this point, according to the fifth mode of the present embodiment, the image processing unit 8 performs processing for removing the second frequency component data included in the moving image data D1, and the display control unit 10 causes the display unit 11 to display a moving image represented by the moving image data D1 having been subjected to the processing. Hence, according to the fifth mode of the present embodiment, the state of gas leaking can be detected from infrared images and can be displayed as a moving image, even when gas leakage and the temperature change of the background are occurring concurrently and the temperature change of the background is greater than the temperature change brought about by the gas having leaked.

Sensor noise becomes smaller as temperature increases, and thus, differs depending upon temperature. In the two-dimensional image sensor 6, noise in accordance with the temperature that each pixel is detecting is generated at the pixel. That is, it is not the case that all pixels have the same noise. High frequency noise can be removed from a moving image according to the fifth mode of the present embodiment. Hence, even slight gas leakage can be detected, and the display unit 11 can be caused to display such slight gas leakage.

The concentration length computation unit 9 included in the fifth mode of the present embodiment functions as a third determination unit. The third determination unit, when gas is detected by the image processing unit 8 (the detection unit), determines a pixel corresponding to a region in which gas is hanging, among the plurality of pixels constituting an infrared image, as the predetermined pixel. To provide detailed description, the third determination unit compares, with a predetermined threshold value that indicates gas leakage, the third difference data for each of the M number of (the plurality of) pixels shown in FIG. 6, and determines, among the M number of pixels, each of two or more pixels for which at least a part of the third difference data has exceeded the threshold value, as the predetermined pixel (the pixel of interest). For example, when at least a part of the third difference data has exceeded the threshold value in each of the 2nd to 10th pixels among the M number of pixels, each of the 2nd to 10th pixels is determined as the predetermined pixel.

The gas concentration length measurement device 3 calculates an estimate value for each of the two or more predetermined pixels having been determined by the third determination unit, by using the processing described on the basis of either the flowchart in FIG. 7 (the first mode of the present embodiment), the flowchart in FIG. 14 (the second mode of the present embodiment), or the flowchart in FIG. 17 (the third mode of the present embodiment). The concentration length computation unit 9 functions as the estimation unit. The estimation unit sets, as the estimate value of the gas concentration length, the maximum estimate value among the estimate values for the two or more predetermined pixels, the estimate values for the two or more predetermined pixels having been determined by the third determination unit. For example, the maximum estimate value among the estimate values for the 2nd to 10th pixels is set as the estimate value of the gas concentration length.

Figure 27:
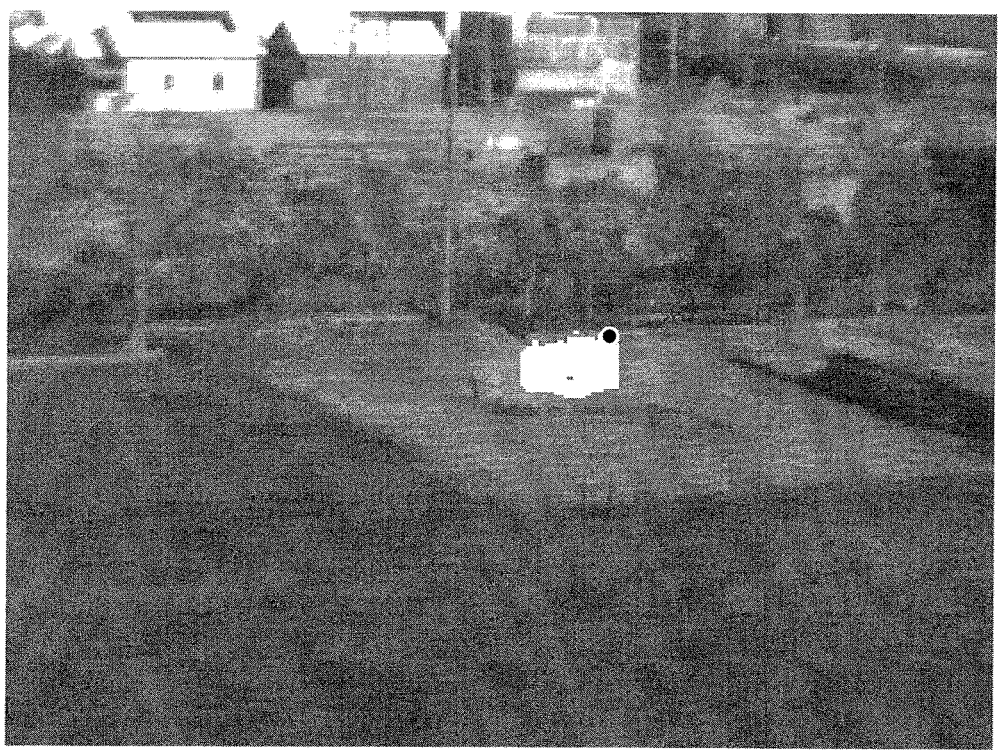
FIG. 27 is an image diagram showing an infrared image having been processed in the fifth mode of the present embodiment.

FIG. 27 is an image diagram showing an infrared image having been processed in the fifth mode of the present embodiment. Each of the pixels forming the white region is a pixel for which an estimate value has been calculated. The pixel indicated by the black dot is the pixel having the greatest estimate value. For the sake of information, the estimate value was 14.0% LELm. The exact gas concentration length was 8% LELm.

According to the fifth mode of the present embodiment, the predetermined pixel is determined from the third difference data. The third difference data does not include the second frequency component data and the third frequency component data. Hence, the predetermined pixel can be determined without being influenced by the temperature change in the background and noise. Due to this, the point from which gas is leaking (the region corresponding to the predetermined pixel) can be detected with improved accuracy, and the gas concentration length corresponding to the detected point can be estimated.

With reference to FIGS. 23 and 24, because the first dispersion data D5 is correlated with the third difference data D9, a mode in which the first dispersion data D5 is used in place of the third difference data D9 is also possible. This mode is constituted of steps S1, S2, and S3 shown in FIG. 20. In this mode, the third determination unit compares, with the predetermined threshold value that indicates gas leakage, the first dispersion data for each of the M number of (the plurality of) pixels shown in FIG. 6, and determines, among the M number of pixels, each of two or more pixels for which at least a part of the first dispersion data has exceeded the threshold value, as the predetermined pixel (the pixel of interest).

Description is provided of a modification of the fifth mode of the present embodiment. This modification ensures that influence of edge noise is avoided.

Figure 28:
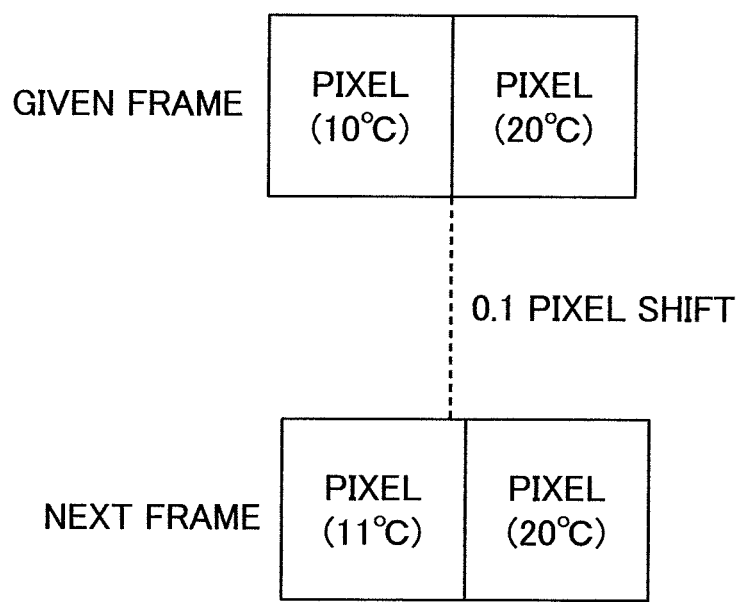
FIG. 28 is an explanatory diagram describing that due to shaking of an infrared camera, an edge shift occurs in adjacent frames.

Due to the shaking of the infrared camera 2 (FIG. 5A), an edge shift occurs when adjacent frames are compared. FIG. 28 is an explanatory diagram describing this. In an image, there is a great change in pixel data values at an edge part. That is, the pixel data value (suppose that the temperature indicated by this value is 10° C.) for a first one of two adjacent pixels forming an edge greatly differs from the pixel data value (suppose that the temperature indicated by this value is 20° C.) of the second one of the two adjacent pixels. Suppose that a 0.1 pixel shift in the direction of the first one of the pixels occurs in the next frame due to the shaking of the infrared camera 2. In such a case, the pixel data value of the first one of the pixel changes, regardless of whether or not gas is present. Due to this, the temperature indicated by the pixel data for the first one of the pixels becomes 11° C.

Figure 29:
FIG. 29 is an image diagram showing edges having been found.

In view of this, the modification of the fifth mode of the present embodiment has the following configuration. The image processing unit 8 in the modification functions as a search unit. The search unit performs a search for edges with respect to an infrared image, by using one of the K number of frames (the K number of infrared images) shown in FIG. 6. For example, when regarding the center pixel in a 3×3 pixel group as a center pixel and the eight pixels located in the periphery of the center pixel as peripheral pixels, the search unit performs processing of calculating, for each of the eight peripheral pixels, an absolute value of a difference between the pixel value of the center pixel and the pixel value of the peripheral pixel, and summing the absolute values so calculated. The search unit searches for edges by performing this processing for each of the plurality of pixels constituting an infrared image. FIG. 29 is an image diagram showing edges having been found. The white lines are the edges. The search for edges may be performed by using a publicly-known method. For example, a filter for searching for edges, such as a Laplacian filter may be used.

The concentration length computation unit 9 in the modification functions as the first determination unit. The first determination unit does not use third difference data (chronological pixel data) for pixels corresponding to the edges having been found by the search unit, in the determination of the with-gas background temperature and the without-gas background temperature. Note that in the case of the above-described mode in which the first dispersion data is used in place of the third difference data, the first determination unit does not use the first dispersion data for pixels corresponding to the edges having been found by the search unit, in the determination of the with-gas background temperature and the without-gas background temperature.

The influence of edge noise can be removed according to the modification of the fifth mode of the present embodiment, and thus, the accuracy of the estimate value of the gas concentration length can be enhanced.

Description is provided of the sixth mode of the present embodiment. In the first through fourth modes of the present embodiment, the with-gas background temperature and the without-gas background temperature are determined by using chronological pixel data as shown in FIGS. 13 and 18 that indicates background temperatures. Meanwhile, in the sixth mode of the present embodiment, predetermined processing is performed with respect to chronological pixel data as shown in FIGS. 13 and 18, and the with-gas background temperature and the without-gas background temperature are determined by using the chronological pixel data after such processing has been performed (the chronological pixel data after predetermined processing).

Figure 30:
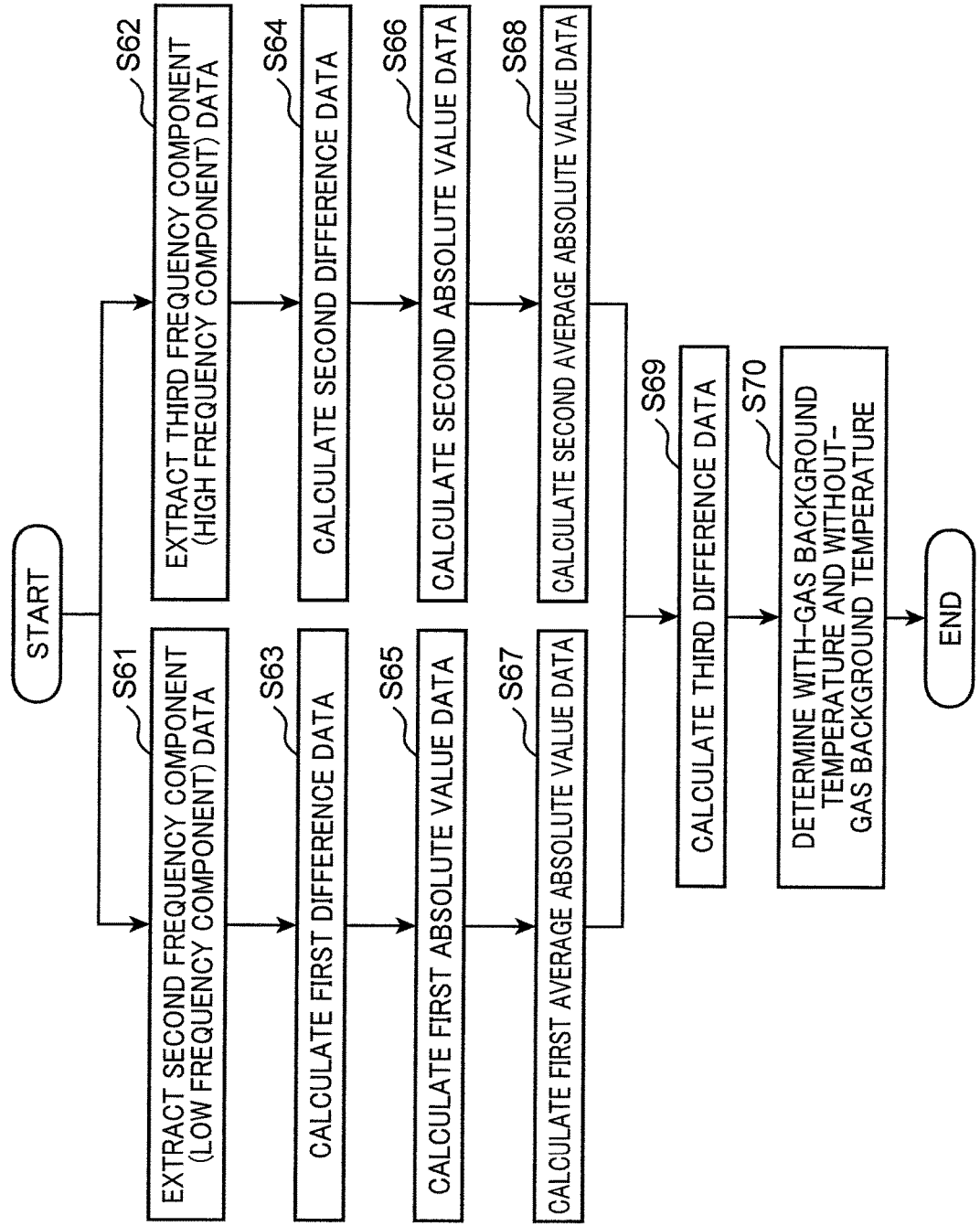
FIG. 30 is a flowchart of processing executed in a sixth mode of the present embodiment.

FIG. 30 is a flowchart of processing executed in the sixth mode of the present embodiment. With reference to FIGS. 5A and 30, the display control unit 10 causes the display unit 11 to display an infrared image of a background including the gas leakage monitoring target. An operator operates the input unit 12 and inputs the position of the pixel of interest (one example of the predetermined pixel) in the infrared image displayed on the display unit 11. Up to this point, the sixth mode is the same as the first mode of the present embodiment.

The image processing unit 8 functions as the first extraction unit. The first extraction unit extracts, as second frequency component data, data extracted from chronological pixel data by calculating a simple moving average (the first predetermined processing) in units of the first predetermined number of frames, which is less than the K number of frames shown in FIG. 6, with respect to the chronological pixel data, and extracts M pieces of second frequency component data respectively corresponding to the M pieces of chronological pixel data shown in FIG. 6 (step S61). This step is the same as step S1 shown in FIG. 20. The second frequency component data is frequency component data that has lower frequency than the first frequency component data, which indicates a temperature brought about by gas, and indicates the change in the background temperature.

The image processing unit 8 functions as the second extraction unit. The second extraction unit extracts, as third frequency component data, data extracted from the chronological pixel data by calculating a simple moving average (the second predetermined processing) in units of the third predetermined number of (for example, 3) frames, which is less than the first predetermined number (for example, 21), with respect to the chronological pixel data, and extracts M pieces of third frequency component data respectively corresponding to the M pieces of chronological pixel data shown in FIG. 6 (step S62). This step is the same as step S4 shown in FIG. 20. The third frequency component data indicates high frequency noise.

Figure 31:
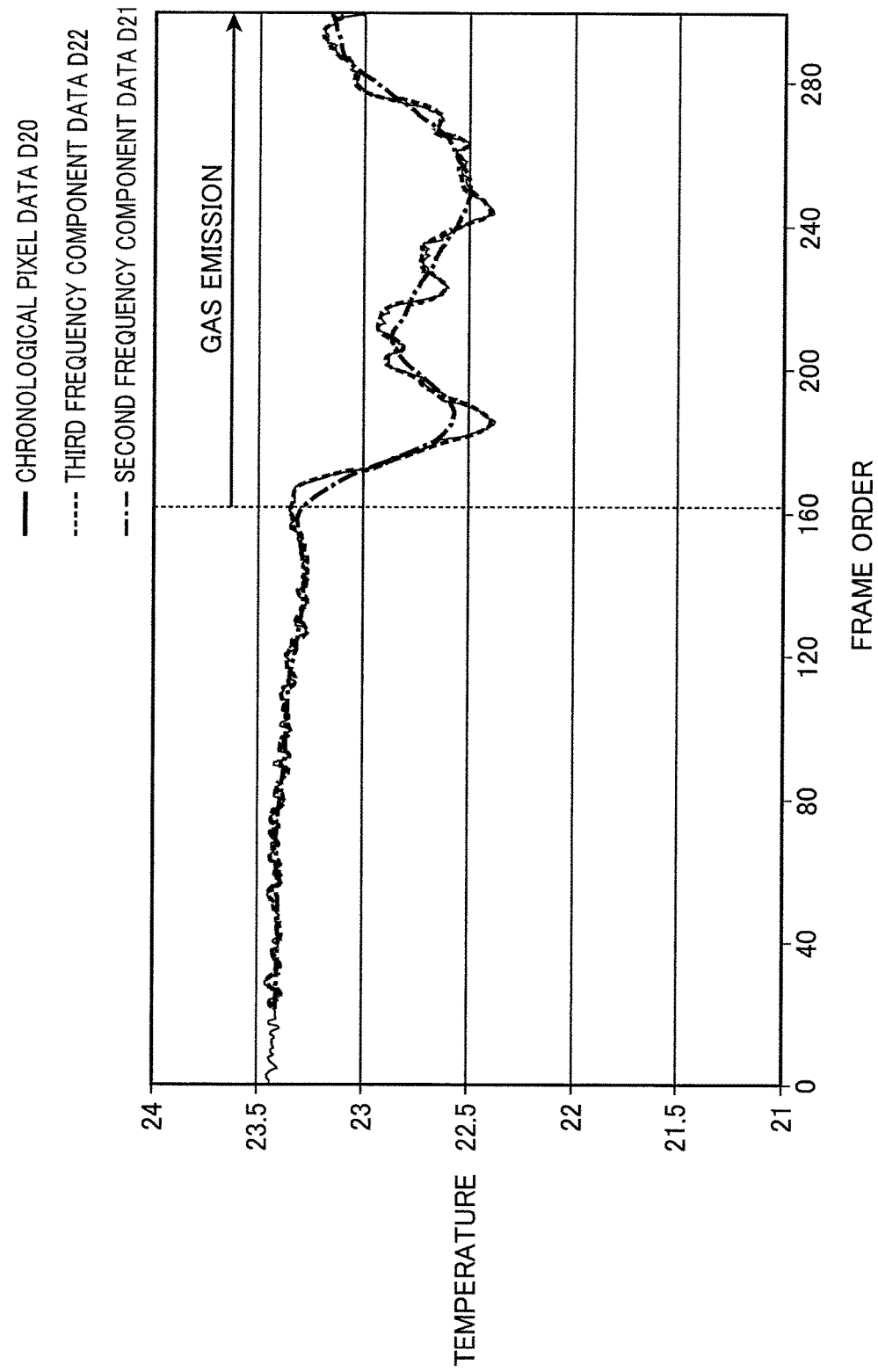
FIG. 31 is a graph showing chronological pixel data D20 for the pixel corresponding to spot SP1 (FIG. 11), second frequency component data D21 extracted from the chronological pixel data D20, and third frequency component data D22 extracted from the chronological pixel data D20.

FIG. 31 is a graph showing chronological pixel data D20 for the pixel corresponding to spot SP1 (FIG. 11), second frequency component data D21 extracted from the chronological pixel data D20, and third frequency component data D22 extracted from the chronological pixel data D20. The vertical and horizontal axes of the graph are the same as the vertical and horizontal axes of the graph shown in FIG. 4. The temperature indicated by the chronological pixel data D20 changes relatively quickly (the cycle of change is relatively short), and the temperature indicated by the second frequency component data D21 changes relatively moderately (the cycle of change is relatively long). The third frequency component data D22 and the chronological pixel data D20 appear to be almost overlapping with one another due to differing in terms of only high frequency components.

The image processing unit 8 functions as the first calculation unit. The first calculation unit calculates, as first difference data, data acquired by calculating a difference between chronological pixel data and the second frequency component data extracted from the chronological pixel data, and calculates M pieces of first difference data respectively corresponding to the M pieces of chronological pixel data (step S63). This step is the same as step S2 shown in FIG. 20.

The image processing unit 8 functions as the third calculation unit. The third calculation unit calculates, as second difference data, data acquired by calculating a difference between first chronological pixel data and the third frequency component data extracted from the first chronological pixel data, and calculates M pieces of second difference data respectively corresponding to the M pieces of chronological pixel data (step S64). This step is the same as step S5 shown in FIG. 20.

Figure 32:
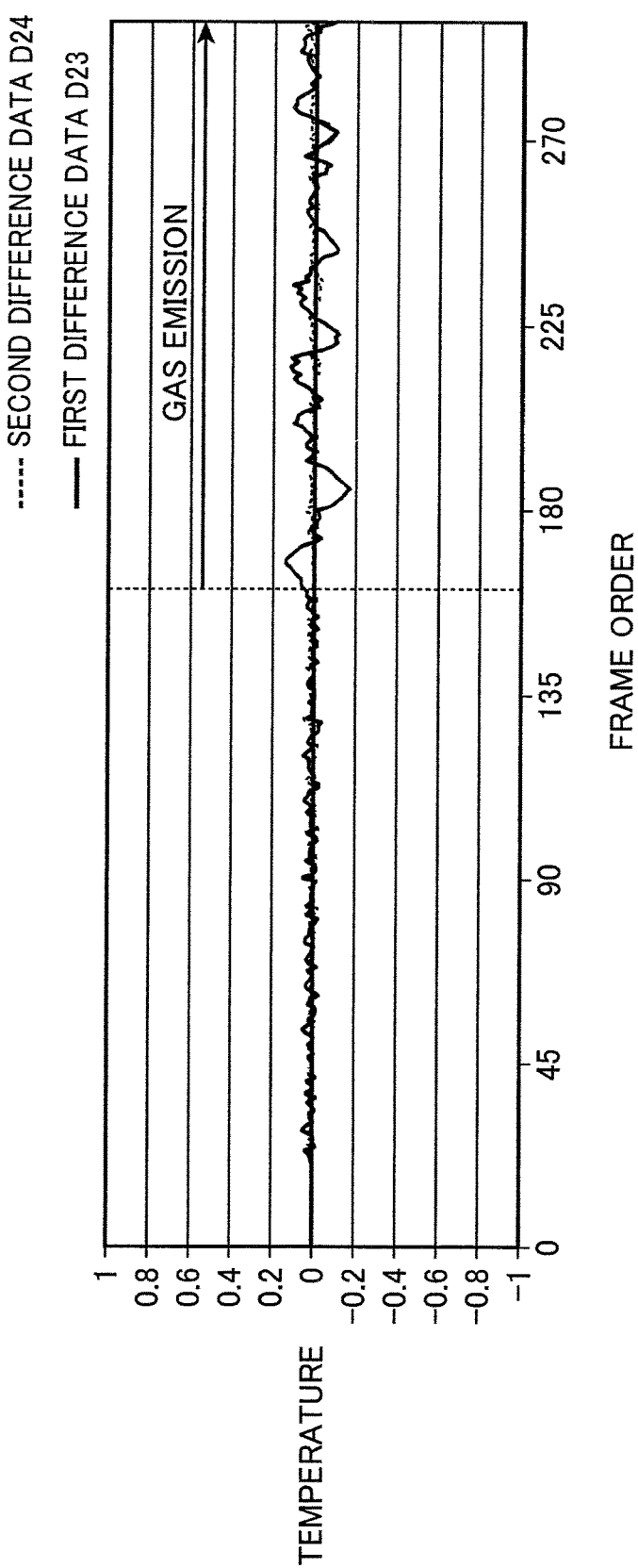
FIG. 32 is a graph showing first difference data D23 and second difference data D24.

FIG. 32 is a graph showing first difference data D23 and second difference data D24. The vertical and horizontal axes of the graph are the same as the vertical and horizontal axes of the graph shown in FIG. 4. The first difference data D23 is data acquired by calculating a difference between the chronological pixel data D20 and the second frequency component data D21, the chronological pixel data D20 and the second frequency component data D21 being shown in FIG. 31. The second difference data D24 is data acquired by calculating a difference between the chronological pixel data D20 and the third frequency component data D22, which are shown in FIG. 31.

The first difference data D23 includes the first frequency component data (the data indicating the temperature change brought about by gas having leaked) and the third frequency component data D22 (the data indicating high frequency noise). The second difference data D24 does not include the first frequency component data and includes the third frequency component data D22.

Because the first difference data D23 includes the first frequency component data, the irregularity in amplitude and waveform of the first difference data D23 becomes greater after the start of gas emission at spot SP1 (the 160th frame and on). Meanwhile, this does not apply to the second difference data D24, because the second difference data D24 does not include the first frequency component data.

The image processing unit 8 functions as the second calculation unit. The second calculation unit calculates, as first fluctuation data, data indicating the fluctuation of the first difference data and being calculated by performing predetermined computation in units of the second predetermined number of frames with respect to the first difference data, and calculates a plurality of pieces of (M pieces of) first fluctuation data respectively corresponding to the plurality of pieces of (the M pieces of) chronological pixel data shown in FIG. 6. There are two types of first fluctuation data, one being first average absolute value data and the other being the first dispersion data. Description is provided on the basis of a case in which the first average absolute value data is used as the first fluctuation data.

The image processing unit 8 functions as the fourth calculation unit. The second calculation unit calculates, as second fluctuation data, data indicating the fluctuation of the second difference data and being calculated by performing predetermined computation in units of the fourth predetermined number of frames with respect to the second difference data, and calculates a plurality of pieces of (M pieces of) second fluctuation data respectively corresponding to the plurality of pieces of (the M pieces of) chronological pixel data shown in FIG. 6. There are two types of second fluctuation data, one being second average absolute value data and the other being the second dispersion data. Description is provided on the basis of a case in which the second average absolute value data is used as the second fluctuation data.

The second calculation unit calculates first absolute value data indicating an absolute value of the first difference data (step S65). The fourth calculation unit calculates second absolute value data indicating an absolute value of the second difference data (step S66).

Figure 33:
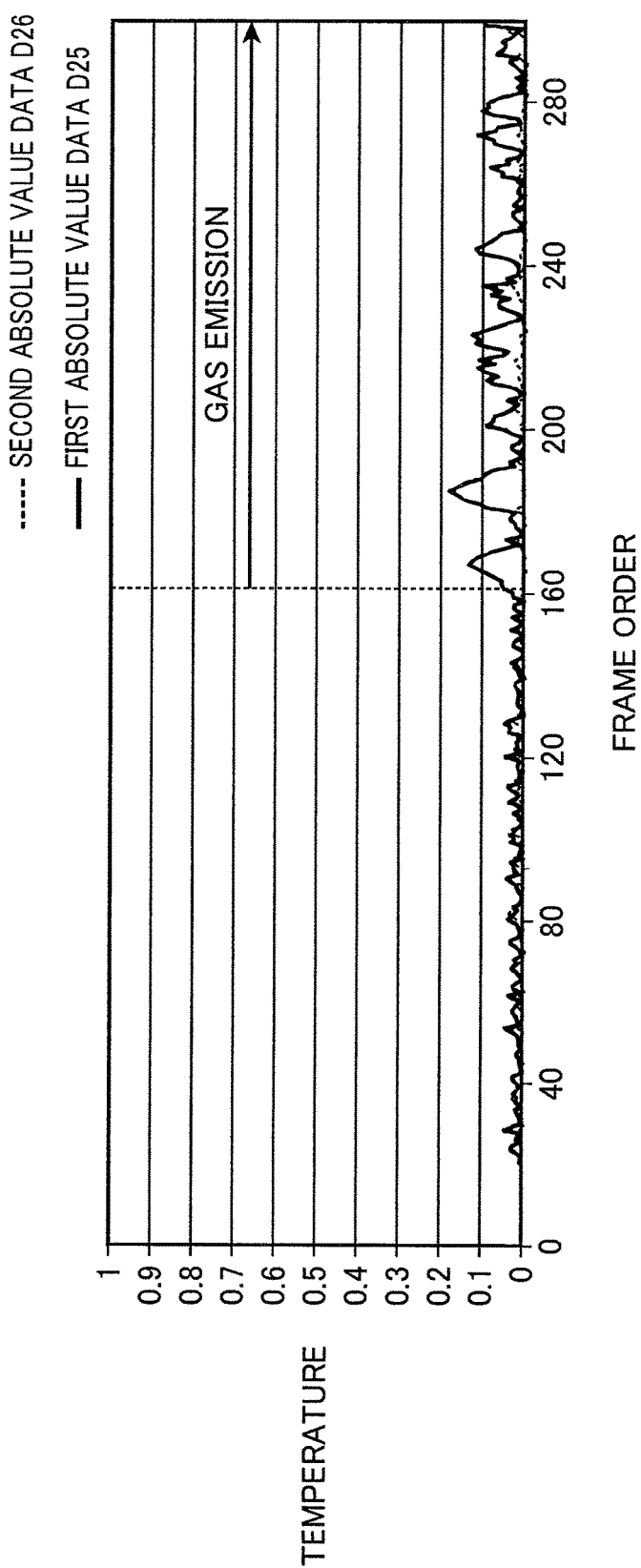
FIG. 33 is a graph showing first absolute value data D25 and second absolute value data D26.

FIG. 33 is a graph showing first absolute value data D25 and second absolute value data D26. The vertical and horizontal axes of the graph are the same as the vertical and horizontal axes of the graph shown in FIG. 4. The first absolute value data D25 is data indicating an absolute value of the first difference data D23 shown in FIG. 32. The second absolute value data D26 is data indicating an absolute value of the second difference data D24 shown in FIG. 32.

The image processing unit 8 functions as the second calculation unit. The second calculation unit calculates the first average absolute value data by calculating a simple moving average in units of the second predetermined number of frames with respect to the first absolute value data (step S67). The image processing unit 8 functions as the fourth calculation unit. The fourth calculation unit calculates the second average absolute value data by calculating a simple moving average in units of the fourth predetermined number of frames with respect to the second absolute value data (step S68). The second and fourth predetermined numbers are, for example, the same as the first predetermined number (21).

The image processing unit 8 functions as the fifth calculation unit. The fifth calculation unit calculates third difference data (step S69). The third difference data is a difference between the first average absolute value data (the first fluctuation data) having been calculated in step S67 and the second average absolute value data (the second fluctuation data) having been calculated in step S68, and becomes the chronological pixel data after the predetermined processing.

Figure 34A:
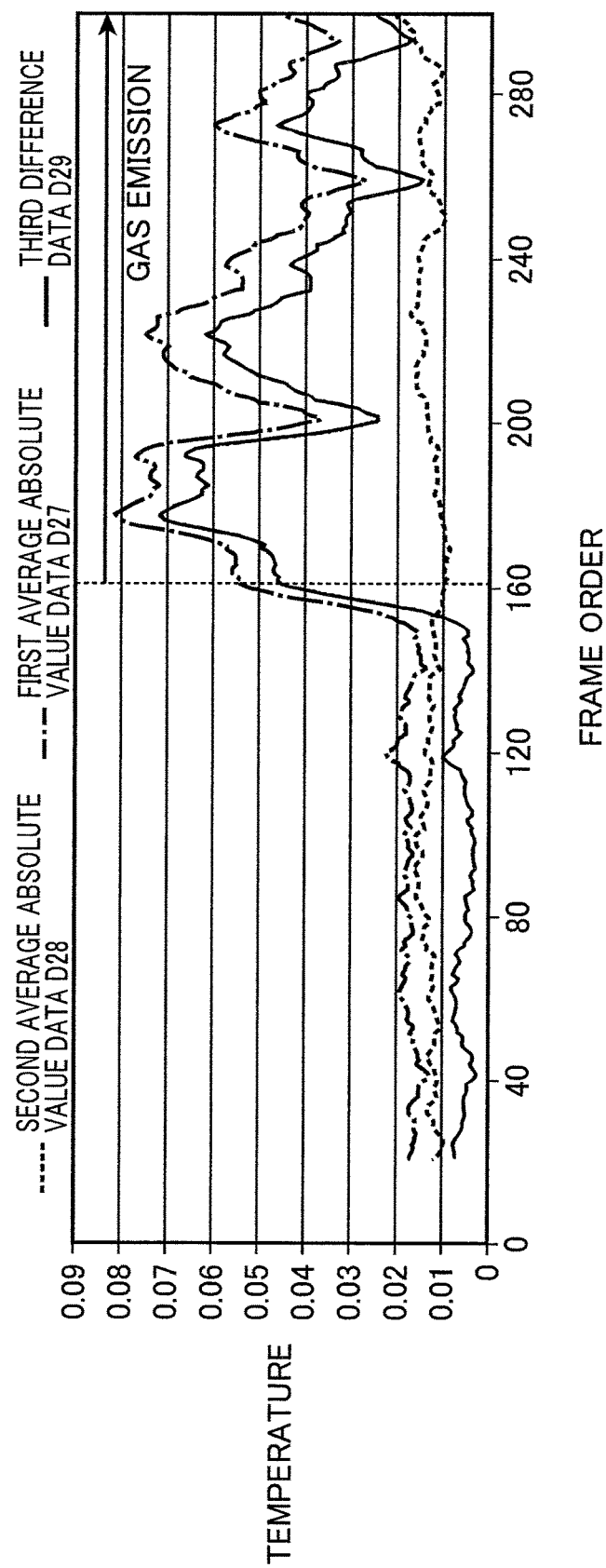
FIG. 34A is a graph showing first average absolute value data D27, second average absolute value data D28, and third difference data D29.

FIG. 34A is a graph showing first average absolute value data D27, second average absolute value data D28, and third difference data D29. The vertical and horizontal axes of the graph are the same as the vertical and horizontal axes of the graph shown in FIG. 4. The first average absolute value data D27 is data acquired by calculating a simple moving average of the first absolute value data D25 shown in FIG. 33. The second average absolute value data D28 is data acquired by calculating a simple moving average of the second absolute value data D26 shown in FIG. 33. The third difference data D29 is data indicating a difference between the first average absolute value data D27 and second average absolute value data D28.

Figure 34B:
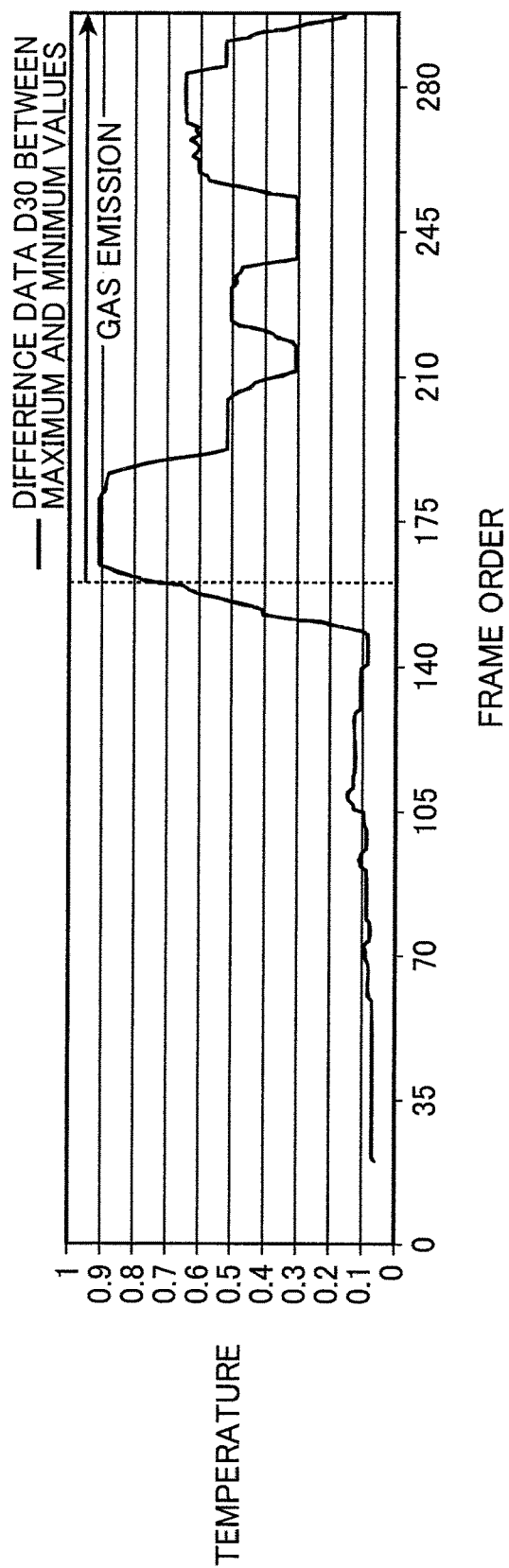
FIG. 34B is a graph showing difference data D30 between maximum and minimum values.

Difference data D30 shown in FIG. 34B indicates a difference between maximum and minimum background temperature values for each frame group, the maximum and minimum background temperature values for each frame group being determined by using the method described on the basis of FIG. 8 with respect to the chronological pixel data D20 shown in FIG. 31. It can be seen that the third difference data D29 is correlated with the difference data D30.

The concentration length computation unit 9 included in the sixth mode of the present embodiment functions as the first determination unit. The first determination unit calculates the with-gas background temperature and the without-gas background temperature by using the third difference data having been calculated in step S69 as the chronological pixel data (step S70). Step S70 differs from the step in the first mode for determining the with-gas background temperature and the without-gas background temperature in that in step S70, the chronological pixel data is not the original chronological pixel data and is the third difference data (the chronological pixel data after the predetermined processing), while all other points are the same. The processing for calculating the estimate value of the gas concentration length by using the with-gas background temperature and the without-gas background temperature is the same as the first mode.

Note that with reference to FIG. 34A, the first average absolute value data D27 is correlated with the third difference data D29. Hence, the first determination unit may determine the with-gas background temperature and the without-gas background temperature by using the first average absolute value data (the first fluctuation data) as the chronological pixel data. This mode is constituted of steps S61, S63, S65, S67, and S70 shown in FIG. 30. However, in this mode, the chronological pixel data would include high frequency noise (the second average absolute value data).

Further, the temperatures indicated on the vertical axis of the graph in FIG. 34A are one-tenths the temperatures indicated on the vertical axis of the graph in FIG. 34B. Hence, the first determination unit can determine the with-gas background temperature and the without-gas background temperature by using data yielded by multiplying the third difference data by ten as the chronological pixel data. Note that the coefficient need not be ten, and can be calculated from data (the moving image data D1 in FIG. 5A) yielded by actually taking an image of the monitoring target.

According to the sixth mode of the present embodiment, the third difference data is used as the chronological pixel data on the basis of which the with-gas background temperature and the without-gas background temperature are determined. The third difference data is data yielded by removing the second frequency component data and the third frequency component data from the chronological pixel data. Hence, the influence of noise and the change in the background temperature can be suppressed, and thus the accuracy of the estimate value of the gas concentration length can be enhanced, specifically when the change in the background temperature is great.

The sixth mode of the present embodiment can be summarized as follows. An extraction unit (the above-described first extraction unit) extracts, from chronological pixel data, frequency component data (the above-described second frequency component data) indicating the temperature change of the background of the monitoring target. A difference data calculation unit (the above-described first calculation unit) calculates difference data (the above-described first difference data) indicating the difference between the chronological pixel data and the frequency component data (the second frequency component data). An absolute value data calculation unit (the above-described second calculation unit) calculates absolute value data (the above-described first absolute value data) indicating an absolute value of the difference data (the first difference data). An average absolute value data calculation unit (the second calculation unit) calculates average absolute value data (the above-described first average absolute value data) indicating a moving average of the absolute value data (the above-described first absolute value data). The first determination unit determines the with-gas background temperature and the without-gas background temperature by using the average absolute value data (the first average absolute value data) as chronological pixel data and by using a method similar to the first mode. The calculation unit calculates gas concentration lengths by using a method similar to the first mode. The second determination unit determines a gas concentration length by using a method similar to the first mode.

The sixth mode of the present embodiment can be used in combination with the first mode of the present embodiment. In the first mode, a case in which there is a rapid and significant change in the background temperature is not taken into consideration. Hence, in such a case, the accuracy of the estimate value of the gas concentration length decreases. According to the sixth mode of the present embodiment, the accuracy of the estimate value of the gas concentration length can be enhanced even in a case when there is a rapid and significant change in the background temperature as described above. In view of this, by using the first mode, a gas concentration length is calculated for each frame group, the estimate value of the gas concentration length is determined from among the gas concentration lengths so calculated, and among these, gas concentration lengths greater than the estimate value of the gas concentration length calculated in the sixth mode are excluded from the candidates of estimate values.

Description is provided of a modification of the sixth mode of the present embodiment. In the modification, first dispersion data and second dispersion data are calculated in place of the first absolute value data, the second absolute value data, the first average absolute value data, and the second average absolute value data that has been described on the basis of FIG. 30.

Figure 35:
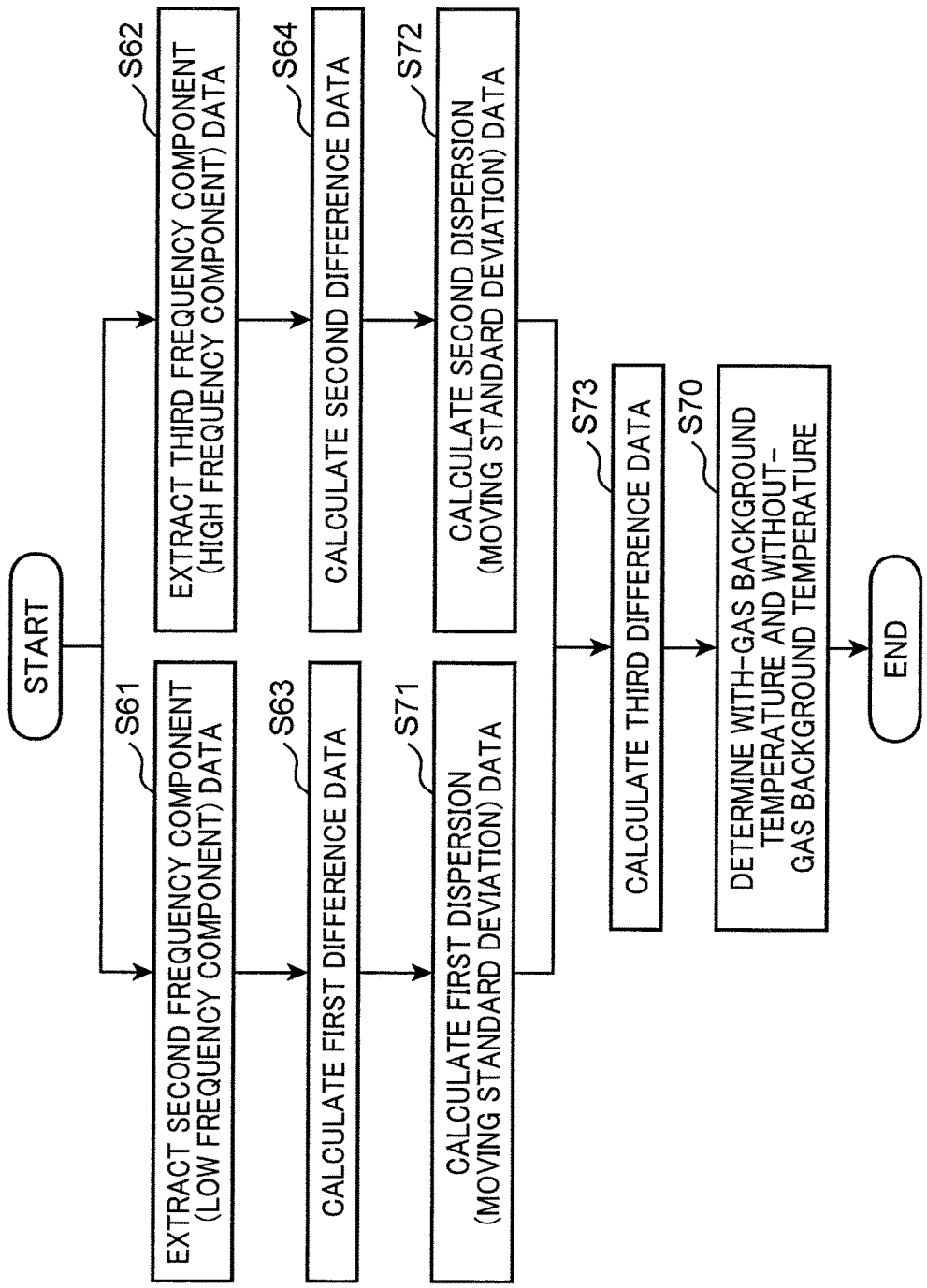
FIG. 35 is a flowchart of processing executed in a modification of the sixth mode of the present embodiment.
Figure 36A:
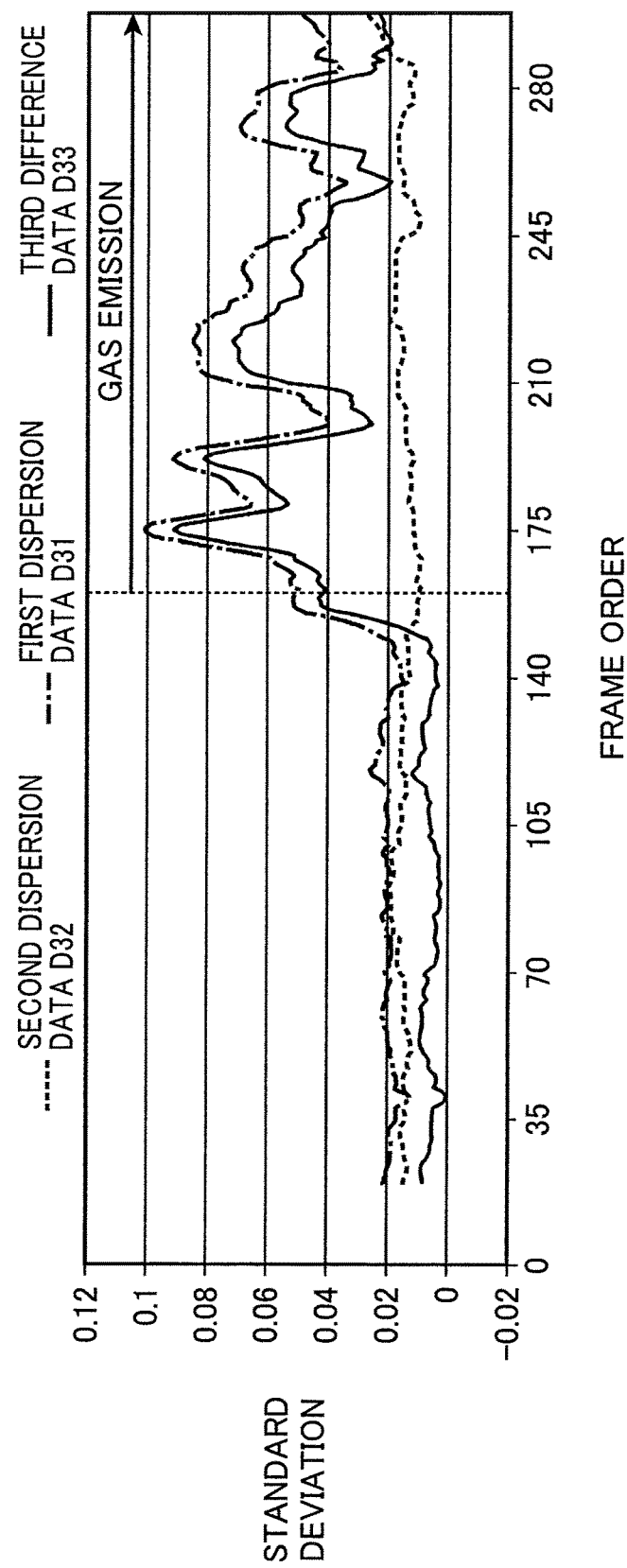
FIG. 36A is a graph showing first dispersion data D31, second dispersion data D32, and third difference data D33.
Figure 36B:
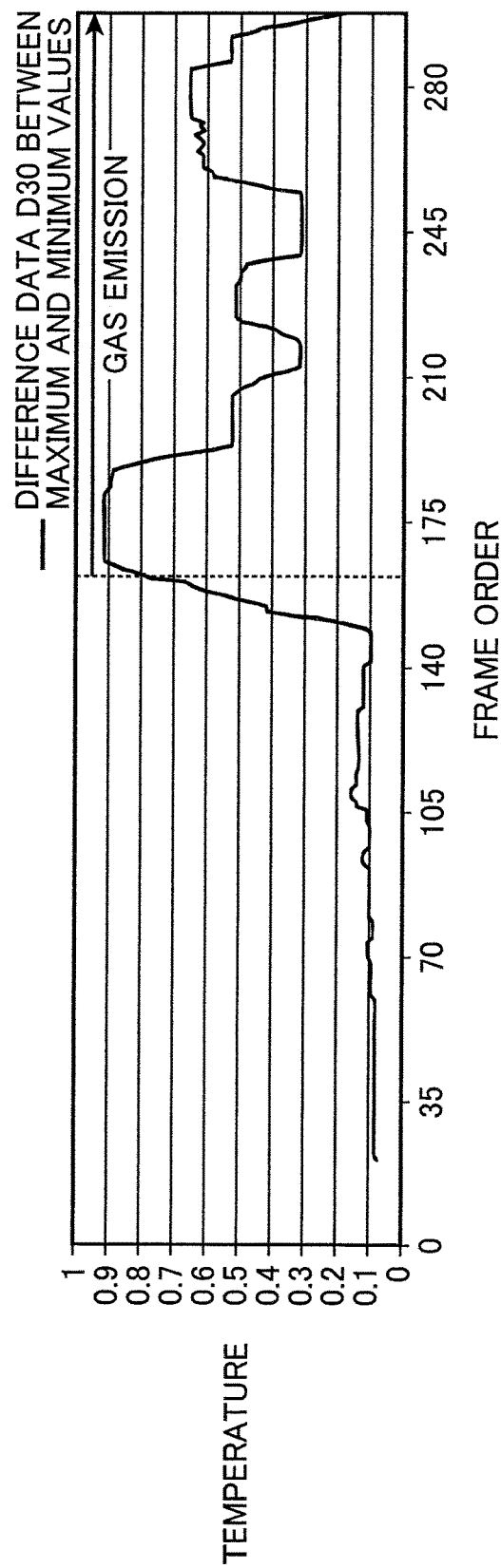
FIG. 36B is a graph showing the difference data D30 between maximum and minimum values.

FIG. 35 is a flowchart of processing executed in the modification of the sixth mode of the present embodiment. FIG. 36A is a graph showing first dispersion data D31, second dispersion data D32, and third difference data D33, and FIG. 36B is a graph showing difference data D30 between maximum and minimum values. The difference data D30 is the same as the difference data D30 in FIG. 34B.

The processing from step S61 to step S64 is the same as the processing from step S61 to step S64 shown in FIG. 30.

The image processing unit 8 functions as the second calculation unit. The second calculation unit calculates, as the first dispersion data (the first fluctuation data), data acquired by calculating a moving standard deviation in units of the second predetermined number of (for example, 21) frames, which is less than the K number of frames shown in FIG. 6, with respect to the first difference data, and calculates M pieces of first dispersion data respectively corresponding to the M pieces of chronological pixel data (step S71). Note that a moving variance may be used in place of a moving standard deviation.

The image processing unit 8 functions as the fourth calculation unit. The fourth calculation unit calculates, as the second dispersion data (the second fluctuation data), data acquired by calculating a moving standard deviation in units of the fourth predetermined number of (for example, 21) frames, which is less than the K number of frames, with respect to the second difference data, and calculates M pieces of second dispersion data respectively corresponding to the M pieces of chronological pixel data (step S72). Note that a moving variance may be used in place of a moving standard deviation.

The number of frames used for the calculation of a moving standard deviation is 21 for both the first dispersion data and the second dispersion data. However, the number is not limited to 21, as long as a standard deviation that is statistically significant can be calculated by using the number.

The image processing unit 8 functions as the fifth calculation unit. The fifth calculation unit calculates, as third difference data, data acquired by calculating a difference between the first dispersion data (the first fluctuation data) and the second dispersion data (the second fluctuation data) that are acquired from the same chronological pixel data, and calculates M pieces of third difference data respectively corresponding to the M pieces of chronological pixel data (step S73). With reference to FIGS. 36A and 36B, it can be seen that the third difference data D33 is correlated with the difference data D30.

The processing in step S70 and on is the same as the sixth mode of the present embodiment. Note that as shown in FIG. 36A, the first dispersion data D31 is correlated with the third difference data D33. Thus, the with-gas background temperature and the without-gas background temperature may be determined by using the first dispersion data as the chronological pixel data. This mode is constituted of steps S61, S63, S71, and S70 shown in FIG. 35. However, in this case, the chronological pixel data would include high frequency noise (the second dispersion data).

This modification has effects similar to the sixth mode of the present embodiment. That is, according to the modification, the third difference data is used as the chronological pixel data on the basis of which the with-gas background temperature and the without-gas background temperature are determined. The third difference data is data yielded by removing the second frequency component data and the third frequency component data from the chronological pixel data. Hence, the influence of noise and the change in the background temperature can be suppressed, and thus the accuracy of the estimate value of the gas concentration length can be enhanced.

The modification of the sixth mode of the present embodiment can be summarized as follows. The extraction unit (the above-described first extraction unit) extracts, from chronological pixel data, frequency component data (the above-described second frequency component data) indicating the temperature change of the background of the monitoring target. The difference data calculation unit (the above-described first calculation unit) calculates difference data (the above-described first difference data) indicating the difference between the chronological pixel data and the frequency component data (the second frequency component data). A dispersion data calculation unit (the above-described second calculation unit) calculates dispersion data (the above-described first dispersion data) indicating the dispersion of the difference data (the above-described first difference data). The first determination unit determines the with-gas background temperature and the without-gas background temperature by using the dispersion data (the first dispersion data) as chronological pixel data and by using a method similar to the first mode. The calculation unit calculates gas concentration lengths by using a method similar to the first mode. The second determination unit determines a gas concentration length by using a method similar to the first mode.

The modification of the sixth mode of the present embodiment can be combined with the fifth mode of the present embodiment shown in FIG. 20. That is, in a case in which the first determination unit calculates the with-gas background temperature and the without-gas background temperature by using the first dispersion data as the chronological pixel data, the first dispersion data having been calculated in step S3 in FIG. 20 is used. In a case in which the first determination unit calculates the with-gas background temperature and the without-gas background temperature by using the third difference data as the chronological pixel data, the third difference data having been calculated in step S7 in FIG. 20 is used.

Description is provided of a first method for calculating the gas concentration length. FIG. 37 is an explanatory diagram describing this method. The two-dimensional image sensor 6 included in the infrared camera 2 shown in FIG. 5A includes sensor pixels corresponding to the pixels (FIGS. 1 and 2). That is, the two-dimensional image sensor 6 is constituted by M sensor pixels from the 1st sensor pixel to the Mth sensor pixel being arrayed two-dimensionally. For example, the two-dimensional image sensor 6 includes a Jth sensor pixel corresponding to the Jth pixel. The Jth sensor pixel thus corresponds to the Jth region.

Igas is a formula indicating a signal (a with-gas background signal) that a given sensor pixel outputs when gas is present in the region corresponding to the sensor pixel. Inogas is a formula indicating a signal (a without-gas background signal) that the sensor pixel outputs when gas is not present in the region corresponding to the sensor pixel. When description is provided on the basis of the Jth sensor pixel, Igas is a formula indicating the signal that the Jth sensor pixel outputs when gas is present in the Jth region. Inogas is a formula indicating the signal that the Jth sensor pixel outputs when gas is not present in the Jth region.

The gas concentration length ct is included in the formula of $\tau gas(\lambda)$, and the formula of $\tau gas(\lambda)$ is included in the formula of Igas. As can be seen from the formula of Igas, the gas concentration length ct can be determined when the with-gas background signal, the gas temperature, the air temperature, the humidity, the distance between the infrared camera 2 and the imaging subject (the gas leakage monitoring target), and a background infrared dose Pback are known. The background infrared dose Pback corresponds to the background temperature. Description is provided in the following taking the gas concentration length ct in the Jth region as an example.

The with-gas background signal output from the Jth sensor pixel can be determined from the with-gas background temperature indicated by the pixel data of the Jth pixel. The gas temperature can be approximated as the air temperature, and thus is regarded as being equal to the air temperature. The air temperature is specified by using an air temperature sensor. The humidity is specified by using a humidity sensor. Because the influence of humidity on the gas concentration length is small, the humidity can be set to 50% rather than specifying the humidity by using a humidity sensor. As the distance, the distance between the infrared camera 2 and the imaging subject that has been set to the infrared camera 2 is used.

The background infrared dose Pback in the Jth region is specified by using the formula of Inogas. To provide detailed description, as can be seen from the formula of Inogas, the background infrared dose Pback can be determined when the without-gas background signal, the air temperature, the humidity, and the distance between the infrared camera 2 and the imaging subject (the gas leakage monitoring target) are known.

The without-gas background signal output from the Jth sensor pixel can be determined from the without-gas background temperature indicated by the pixel data of the Jth pixel. The air temperature, the humidity, and the distance can be specified as described above. A formula for calculating the background infrared dose Pback from these parameters (the without-gas background signal, the air temperature, the humidity, and the distance) does not exist. Thus, a table indicating the relationships between these parameters and the background infrared dose Pback is created in advance. The background infrared dose Pback is calculated by using this table and the parameters (and by further using interpolation, if necessary). Note that the background infrared dose Pback may be calculated without using the table and by using a convergence calculation.

A formula for calculating the gas concentration length ct from the parameters specified as described above (the with-gas background signal, the gas temperature, the air temperature, the humidity, the distance, and the background infrared dose Pback) does not exist. Thus, a table indicating the relationships between these parameters and the gas concentration length ct is created in advance. The gas concentration length ct is calculated by using this table and the parameters (and by further using interpolation, if necessary). Note that the gas concentration length ct may be calculated without using the table and by using a convergence calculation.

According to the first method described above, the gas concentration length measurement device 3 calculates the gas concentration length by regarding the air temperature of the site at which the monitoring target is located as gas temperature. Hence, gas temperature becomes unnecessary for the calculation of the gas concentration length.

Next, description is provided of a second method for calculating the gas concentration length. FIG. 38 is an explanatory diagram describing this method. According to the second method, gas temperature becomes unnecessary for the calculation of the gas concentration length.

Among a plurality of pixels constituting an infrared image, two pixels predicted as having equal gas concentration lengths by an operator of the gas concentration length measurement device 3 are referred to as a first pixel and a second pixel. A sensor pixel corresponding to the first pixel is referred to as a first sensor pixel, and a sensor pixel corresponding to the second pixel is referred to as a second sensor pixel. Igas1 is a formula indicating the signal (the with-gas background signal) that the first sensor pixel outputs when gas is present in the region corresponding to the first sensor pixel. Igas2 is a formula indicating the signal (the with-gas background signal) that the second sensor pixel outputs when gas is present in the region corresponding to the second sensor pixel.

Suppose that the region corresponding to the first sensor pixel (the first pixel) and the region corresponding to the second sensor pixel (the second pixel) only differ in terms of the background infrared dose Pback. The background infrared dose Pback corresponds to the background temperature. In this case, the formula expressed as Igas2–Igas1 is not dependent upon gas temperature. In the second method, the gas concentration length is calculated by using the formula expressed as Igas2–Igas1.

First, similarly to the first method, the background infrared dose Pback in the region corresponding to the first sensor pixel and the background infrared dose Pback in the region corresponding to the second sensor pixel are each calculated by using the formula of Inogas.

Next, the with-gas background signal output from the first sensor pixel and the with-gas background signal output from the second sensor pixel are determined. The former can be determined from the with-gas background temperature indicated by the pixel data of the first pixel, and the latter can be determined from the with-gas background temperature indicated by the pixel data of the second pixel. Then, Igas2–Igas1, that is, the difference between the with-gas background signal output from the second sensor pixel and the with-gas background signal output from the first sensor pixel is calculated.

A formula for calculating the gas concentration length ct from the parameters (Igas2–Igas1, the air temperature, the humidity, and the distance) does not exist. Thus, a table indicating the relationships between these parameters and the gas concentration length ct is created in advance. The gas concentration length ct is calculated by using this table and the parameters (and by further using interpolation, if necessary). Note that the gas concentration length ct may be calculated without using the table and by using a convergence calculation.

Figure 39:
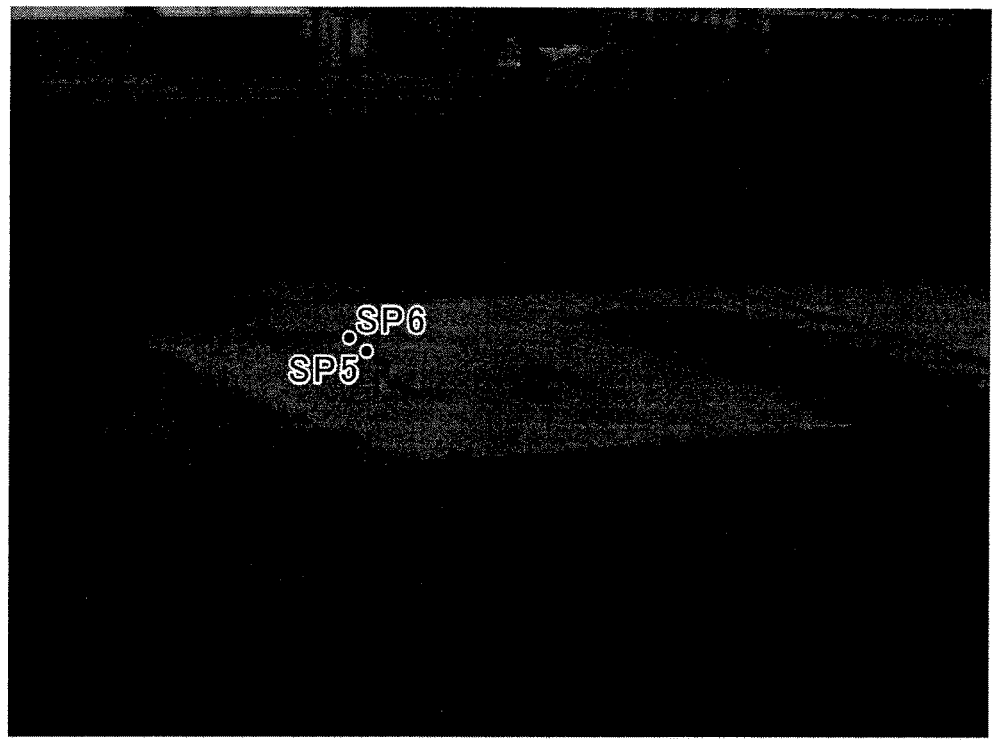
FIG. 39 is an image diagram showing an infrared image displayed on the display unit in a seventh mode of the present embodiment.

Description is provided of the seventh mode of the present embodiment. In this mode, the second method is used for calculating the gas concentration length. With reference to FIG. 5A, the display control unit 10 causes the display unit 11 to display an infrared image of a background including the gas leakage monitoring target. FIG. 39 is an image diagram showing an infrared image displayed on the display unit 11. Two pixels predicted as having equal concentration lengths by an operator are referred to as a first pixel and a second pixel. For example, suppose that the pixel corresponding to spot SP5 is the first pixel and the pixel corresponding to spot SP6 is the second pixel. The operator operates the input unit 12 and inputs the positions of the first and second pixels in the infrared image displayed on the display unit 11.

The gas concentration length computation unit 9 included in the seventh mode of the present embodiment functions as the first determination unit. The first determination unit, similarly to step S31 in FIG. 7, determines the with-gas background temperature and the without-gas background temperature for each of the first pixel and the second pixel. That is, the first determination unit determines the with-gas background temperature and the without-gas background temperature in the first pixel among the M number of pixels shown in FIG. 6 on the basis of the chronological pixel data for the first pixel by setting, as the with-gas background temperature, a background temperature indicated by the pixel data of the first pixel when gas is present in a first region corresponding to the first pixel, and as the without-gas background temperature, a background temperature indicated by the pixel data of the first pixel when gas is not present in the first region. Further, the first determination unit also determines the with-gas background temperature and the without-gas background temperature for the second pixel in a similar manner, on the basis of the chronological pixel data for the second pixel.

The gas concentration length is calculated similarly to step S32 in FIG. 7. In the seventh mode of the present embodiment, the gas concentration length is calculated by using the second method described above. That is, the concentration length computation unit 9 included in the seventh mode of the present embodiment functions as the calculation unit. The calculation unit, for each of the plurality of frame groups, calculates gas concentration lengths by using the with-gas background temperature and the without-gas background temperature, which have been determined as described above, for the first pixel, and also the with-gas background temperature and the without-gas background temperature, which have been determined as described above, for the second pixel. Processing following this is the same as FIG. 7.

In the seventh mode of the present embodiment, the first mode of the present embodiment shown in FIG. 7 is applied as the processing for calculating the gas concentration length. However, the second mode of the present embodiment shown in FIG. 14 or the third mode of the present embodiment shown in FIG. 17 may be applied.

The gas concentration length measurement device 3, shown in FIG. 5A, relating to the present embodiment, includes the display control unit 10 and the display unit 11. The present invention is not limited to this configuration, and the gas concentration length measurement device 3 may have a configuration in which neither the display control unit 10 nor the display unit 11 is included, or a configuration in which the display unit 11 is not included.

Summary of Embodiment

A gas concentration length measurement device relating to a first aspect of the present embodiment is a gas concentration length measurement device for measuring a gas concentration length by using an infrared image constituted of a plurality of pixels, the gas concentration length measurement device including: an image data input unit that receives input of image data representing a plurality of the infrared images yielded by the infrared image of a gas leakage monitoring target being taken at a plurality of time points; and a first determination unit that generates chronological pixel data in which pieces of pixel data for the pixels located at a same position in the plurality of infrared images input from the image data input unit are lined-up in chronological order, and on the basis of the chronological pixel data for a predetermined pixel among the plurality of pixels, determines: a with-gas background temperature indicating a background temperature when gas is present in a predetermined region corresponding to the predetermined pixel; and a without-gas background temperature indicating a background temperature when gas is not present in the predetermined region. This structure corresponds to the first through seventh modes of the present embodiment.

The inventors of the present invention have found that, due to the swaying of gas having leaked, the possibility is high that, in a predetermined region corresponding to a predetermined pixel, a state in which gas is present and a state in which gas is not present occur when seen chronologically. The chronological pixel data corresponding to the predetermined pixel is data of a change in a background temperature of the region corresponding to the predetermined pixel. The first determination unit determines the with-gas background temperature and the without-gas background temperature by using the chronological pixel data for the predetermined pixel. Hence, according to the gas concentration length measurement device relating to the first aspect of the present embodiment, the with-gas background temperature and the without-gas background temperature can be measured with one infrared camera, without requiring two types of filters and a mechanism for switching the filters.

In the above-described structure, the image data input unit receives input of the image data having a structure in which a plurality of frames are lined-up in chronological order, the first determination unit determines maximum and minimum background temperature values from among background temperatures indicated by pieces of pixel data, in the chronological pixel data, that are included in a frame group including a predetermined number of consecutive frames, and determines the maximum background temperature value as one of the without-gas background temperature and the with-gas background temperature and determines the minimum background temperature value as the other one of the without-gas background temperature and the with-gas background temperature, and the first determination unit prepares a plurality of the frame groups having different combinations of the frames, and determines the with-gas background temperature and the without-gas background temperature for each of the plurality of frame groups. This structure corresponds to the first, second, and fourth through seventh modes of the present embodiment.

This structure is one mode for determining the with-gas background temperature and the without-gas background temperature by using the chronological pixel data.

In the above-described structure, the image data input unit receives input of the image data having a structure in which a plurality of frames are lined-up in chronological order, and the first determination unit forms the chronological pixel data by using pieces of pixel data for the predetermined pixel from all frames, determines maximum and minimum background temperature values from among background temperatures indicated by pieces of pixel data in the chronological pixel data, and determines the maximum background temperature value as one of the without-gas background temperature and the with-gas background temperature and determines the minimum background temperature value as the other one of the without-gas background temperature and the with-gas background temperature. This structure corresponds to the third mode of the present embodiment.

According to this structure, the unit for which the with-gas background temperature and the without-gas background temperature are determined is the entirety of frames (the plurality of frames) and not each frame group. Due to this, the with-gas background temperature and the without-gas background temperature can be determined even if the cycle of the switching from the state in which gas is present to the state in which gas is not present and the switching from the state in which gas is not present to the state in which gas is present is long.

In the above-described structure, the gas concentration length measurement device further includes: an extraction unit that extracts, from the chronological pixel data, frequency component data indicating a temperature change of a background of the monitoring target; a difference data calculation unit that calculates difference data indicating a difference between the chronological pixel data and the frequency component data; an absolute value data calculation unit that calculates absolute value data indicating an absolute value of the difference data; and an average absolute value calculation unit that calculates average absolute value data indicating a moving average of the absolute value data, wherein the first determination unit determines the with-gas background temperature and the without-gas background temperature on the basis of the average absolute value data. This structure corresponds to the sixth mode of the present embodiment.

According to this structure, the average absolute value data is used as the chronological pixel data on the basis of which the with-gas background temperature and the without-gas background temperature are determined. The average absolute value data is data yielded by removing the frequency component data indicating the temperature change of the background of the monitoring target from the chronological pixel data. Hence, the influence of the change in background temperature can be suppressed, and thus the accuracy of measurement of the with-gas background temperature and the without-gas background temperature can be enhanced.

In the above-described structure, the gas concentration length measurement device further includes an extraction unit that extracts, from the chronological pixel data, frequency component data indicating a temperature change of a background of the monitoring target; a difference data calculation unit that calculates difference data indicating a difference between the chronological pixel data and the frequency component data; and a dispersion data calculation unit that calculates dispersion data indicating a dispersion of the difference data, wherein the first determination unit determines the with-gas background temperature and the without-gas background temperature on the basis of the dispersion data. This structure corresponds to the modification of the sixth mode of the present embodiment.

According to this structure, the dispersion data is used as the chronological pixel data on the basis of which the with-gas background temperature and the without-gas background temperature are determined. The dispersion data is data yielded by removing the frequency component data indicating the temperature change of the background of the monitoring target from the chronological pixel data. Hence, the influence of the change in background temperature can be suppressed, and thus the accuracy of measurement of the with-gas background temperature and the without-gas background temperature can be enhanced.

In the above-described structure, the gas concentration length measurement device further includes a product calculation unit that, for each of the plurality of frame groups, calculates the gas concentration length by using the with-gas background temperature and the without-gas background temperature that have been determined by the first determination unit; and a second determination unit that determines the gas concentration length from among the gas concentration lengths for the respective ones of the plurality of frame groups, the gas concentration lengths having been calculated by the product calculation unit. This structure corresponds to the first, second, and fourth through seventh modes of the present embodiment.

In the above-described structure, the first determination unit determines maximum and minimum background temperature values from among background temperatures indicated by pieces of pixel data, in the average absolute value data for the predetermined pixel, that are included in a frame group including a predetermined number of consecutive frames, and determines the maximum background temperature value as one of the without-gas background temperature and the with-gas background temperature and determines the minimum background temperature value as the other one of the without-gas background temperature and the with-gas background temperature, the first determination unit prepares a plurality of the frame groups having different combinations of the frames, and determines the with-gas background temperature and the without-gas background temperature for each of the plurality of frame groups, and the gas concentration length measurement device further includes a product calculation unit that, for each of the plurality of frame groups, calculates the gas concentration length by using the with-gas background temperature and the without-gas background temperature that have been determined by the first determination unit; and a second determination unit that determines the gas concentration length from among the gas concentration lengths for the respective ones of the plurality of frame groups, the gas concentration lengths having been calculated by the product calculation unit. This structure corresponds to the sixth mode of the present embodiment.

In the above-described structure, the first determination unit determines maximum and minimum background temperature values from among background temperatures indicated by pieces of pixel data, in the dispersion data for the predetermined pixel, that are included in a frame group including a predetermined number of consecutive frames, and determines the maximum background temperature value as one of the without-gas background temperature and the with-gas background temperature and determines the minimum background temperature value as the other one of the without-gas background temperature and the with-gas background temperature, the first determination unit prepares a plurality of the frame groups having different combinations of the frames, and determines the with-gas background temperature and the without-gas background temperature for each of the plurality of frame groups, and the gas concentration length measurement device further includes a product calculation unit that, for each of the plurality of frame groups, calculates the gas concentration length by using the with-gas background temperature and the without-gas background temperature that have been determined by the first determination unit; and a second determination unit that determines the gas concentration length from among the gas concentration lengths for the respective ones of the plurality of frame groups, the gas concentration lengths having been calculated by the product calculation unit. This structure corresponds to the modification of the sixth mode of the present embodiment.

As described above, the with-gas background temperature and the without-gas background temperature can be determined by using the phenomenon of the swaying of leaking gas. The swaying of gas is caused by wind, etc. Hence, the temperature difference between the with-gas background temperature and the without-gas background temperature fluctuates along the time axis, and the gas concentration length also fluctuates along the time axis as a result. In these three structures, the gas concentration lengths for the respective ones of the plurality of frame groups are set as candidate values, and a gas concentration length is determined from among the candidate values.

In the above-described structure, the first determination unit determines the with-gas background temperature and the without-gas background temperature for each of a pixel of interest and two or more peripheral pixels in a periphery of the pixel of interest, the pixel of interest and the two or more peripheral pixels included among the plurality of pixels constituting the infrared image, and the gas concentration length measurement device further includes a product calculation unit that, for each of the pixel of interest and the two or more peripheral pixels, calculates the gas concentration length on the basis of the with-gas background temperature and the without-gas background temperature, having been determined by the first determination unit, for each of the pixel of interest and the two or more peripheral pixels; and a second determination unit that determines the gas concentration length from among the gas concentration lengths for the respective ones of the pixel of interest and the two or more peripheral pixels, the gas concentration lengths having been calculated by the product calculation unit. This structure corresponds to the fourth mode of the present embodiment.

The manner in which leaking gas sways varies pixel-by-pixel. Hence, the level of change in gas concentration reflected on pixels varies pixel-by-pixel. Due to this, it is not necessarily the case that gas concentration length in the region corresponding to the pixel of interest is the maximum gas concentration length. According to this structure, the gas concentration lengths in regions corresponding to pixels located in the periphery of the pixel of interest are also taken into consideration.

In the above-described structure, the gas concentration length measurement device further includes a detection unit that detects gas by using the infrared image; and a third determination unit that, when gas is detected by the detection unit, determines a pixel corresponding to a region in which gas is hanging, among the plurality of pixels, as the predetermined pixel. This structure corresponds to the fifth mode of the present embodiment.

According to this structure, the predetermined pixel is determined not by an operator but by the gas concentration length measurement device.

In the above-described structure, the gas concentration length measurement device further includes a search unit that uses an infrared image among the plurality of infrared images and searches for an edge in the infrared image, and the first determination unit does not use the chronological pixel data for the pixel corresponding to the edge found by the search unit for the determination of the with-gas background temperature and the without-gas background temperature. This structure corresponds to the modification of the fifth mode of the present embodiment.

According to this structure, the influence of edge noise can be removed, and thus, the accuracy of the gas concentration length can be enhanced.

In the above-described structure, the first determination unit determines maximum and minimum background temperature values for each of the predetermined pixel and two or more of the pixels that have been set in advance and are located in a periphery of the predetermined pixel, on the basis of the chronological pixel data for each of the predetermined pixel and the two or more pixels, and the gas concentration length measurement device further includes a correction unit that corrects the maximum and minimum background temperature values for the predetermined pixel on the basis of the maximum and minimum background temperature values for each of the two or more pixels. This structure corresponds to the second mode of the present embodiment.

In this structure, a correction value is calculated by using two or more pixels located in the periphery of the predetermined pixel, and the with-gas background temperature and the without-gas background temperature for the predetermined pixel are determined by regarding the correction value as the amount of change in the background temperature and taking this into consideration. Hence, according to this structure, even when the background temperature changes rapidly and significantly during gas leakage, the influence of the change can be suppressed.

In the above-described structure, the gas concentration length measurement device calculates the gas concentration length by regarding an air temperature of a site at which the monitoring target is located as a temperature of the gas.

According to this structure, gas temperature becomes unnecessary for the calculation of the gas concentration length.

In the above-described structure, the gas concentration length measurement device calculates the gas concentration length by using the with-gas background temperature and the without-gas background temperature for a first pixel and a second pixel, among the plurality of pixels constituting the infrared image, the gas concentration lengths for the first pixel and the second pixel being predicted as being equal. This structure corresponds to the seventh mode of the present embodiment.

According to this structure, gas temperature becomes unnecessary for the calculation of the gas concentration length.

A gas concentration length measurement method relating to a second aspect of the present embodiment is a gas concentration length measurement method for measuring a gas concentration length by using an infrared image constituted of a plurality of pixels, the gas concentration length measurement method including: a first step of acquiring image data representing a plurality of the infrared images yielded by the infrared image of a gas leakage monitoring target being taken at a plurality of time points; and a second step of generating chronological pixel data in which pieces of pixel data for the pixels located at a same position in the plurality of infrared images acquired in the first step are lined-up in chronological order, and on the basis of the chronological pixel data for a predetermined pixel among the plurality of pixels, determining: a with-gas background temperature indicating a background temperature when gas is present in a predetermined region corresponding to the predetermined pixel; and a without-gas background temperature indicating a background temperature when gas is not present in the predetermined region.

The gas concentration length measurement method relating to the second aspect of the present embodiment has actions and effects similar to the gas concentration length measurement device relating to the first aspect of the present embodiment.

A gas concentration length measurement program relating to a third aspect of the present embodiment is a gas concentration length measurement program for measuring a gas concentration length by using an infrared image constituted of a plurality of pixels, the gas concentration length measurement program causing a computer of a gas concentration length measurement device to execute: a first step of acquiring image data representing a plurality of the infrared images yielded by the infrared image of a gas leakage monitoring target being taken at a plurality of time points; and a second step of generating chronological pixel data in which pieces of pixel data for the pixels located at a same position in the plurality of infrared images acquired in the first step are lined-up in chronological order, and on the basis of the chronological pixel data for a predetermined pixel among the plurality of pixels, determining: a with-gas background temperature indicating a background temperature when gas is present in a predetermined region corresponding to the predetermined pixel; and a without-gas background temperature indicating a background temperature when gas is not present in the predetermined region.

The gas concentration length measurement program relating to the third aspect of the present embodiment has actions and effects similar to the gas concentration length measurement device relating to the first aspect of the present embodiment.

This application is based on JP 2015-244192 filed on Dec. 15, 2015, the contents of which are included in the present application.

In order to express the present invention, the present invention has been described appropriately and sufficiently above through an embodiment while referring to the drawings. It should however be acknowledged that a person skilled in the art could easily modify and/or improve the above-described embodiment. Hence, a modified or improved form to be carried out by a person skilled in the art shall be construed as being included in the scope of rights of the claims recited in the Scope of Claims, unless the modified or improved form is that of a level departing from the scope of rights of the claims.

INDUSTRIAL APPLICABILITY

According to the present invention, a gas concentration length measurement device, a gas concentration length measurement method, a gas concentration length measurement program, and a computer-readable recording medium having a gas concentration length measurement program recorded thereon can be provided.

The invention claimed is:

1. A gas concentration length measurement device for measuring a gas concentration length by using an infrared image constituted of a plurality of pixels, the gas concentration length measurement device comprising:
   a communication interface that receives input of image data representing a plurality of infrared images yielded by the plurality of infrared images of a gas leakage monitoring target being taken at a plurality of time points, the plurality of the infrared images each being taken in a specific wavelength region within the infrared band; and
   a hardware processor that generates chronological pixel data in which pieces of pixel data for pixels located at a same position in the plurality of infrared images input from the communication interface are lined-up in chronological order, and on the basis of the chronological pixel data for a predetermined pixel among the plurality of pixels, determines: a with-gas background temperature indicating a background temperature when gas is present in a predetermined region corresponding to the predetermined pixel; and
   a without-gas background temperature indicating a background temperature when gas is not present in the predetermined region.

2. The gas concentration length measurement device according to claim 1, wherein
   the communication interface receives input of the image data having a structure in which a plurality of frames are lined-up in chronological order,
   the hardware processor determines maximum and minimum background temperature values from among background temperatures indicated by pieces of pixel data, in the chronological pixel data, that are included in a frame group including a predetermined number of consecutive frames, and determines the maximum background temperature value as one of the without-gas background temperature and the with-gas background temperature and determines the minimum background temperature value as the other one of the without-gas background temperature and the with-gas background temperature, and
   the hardware processor prepares a plurality of the frame groups having different combinations of the frames, and determines the with-gas background temperature and the without-gas background temperature for each of the plurality of frame groups.

3. The gas concentration length measurement device according to claim 2, wherein
   the hardware processor that, for each of the plurality of frame groups, calculates the gas concentration length by using the with-gas background temperature and the without-gas background temperature that have been determined by the hardware processor; and
   the hardware processor that determines the gas concentration length from among the gas concentration lengths for the respective ones of the plurality of frame groups, the gas concentration lengths having been calculated by the hardware processor.

4. The gas concentration length measurement device according to claim 1, wherein
   the communication interface receives input of the image data having a structure in which a plurality of frames are lined-up in chronological order, and
   the hardware processor forms the chronological pixel data by using pieces of pixel data for the predetermined pixel from all frames, determines maximum and minimum background temperature values from among background temperatures indicated by pieces of pixel data in the chronological pixel data, and determines the maximum background temperature value as one of the without-gas background temperature and the with-gas background temperature and determines the minimum background temperature value as the other one of the without-gas background temperature and the with-gas background temperature.

5. The gas concentration length measurement device according to claim 1, wherein
   the hardware processor that extracts, from the chronological pixel data, frequency component data indicating a temperature change of a background of the monitoring target;
   the hardware processor that calculates difference data indicating a difference between the chronological pixel data and the frequency component data;
   the hardware processor that calculates absolute value data indicating an absolute value of the difference data; and
   the hardware processor that calculates average absolute value data indicating a moving average of the absolute value data, wherein
   the hardware processor determines the with-gas background temperature and the without-gas background temperature on the basis of the average absolute value data.

6. The gas concentration length measurement device according to claim 5, wherein
   the hardware processor determines maximum and minimum background temperature values from among background temperatures indicated by pieces of pixel data, in the average absolute value data for the predetermined pixel, that are included in a frame group including a predetermined number of consecutive frames, and determines the maximum background temperature value as one of the without-gas background temperature and the with-gas background temperature and determines the minimum background temperature value as the other one of the without-gas background temperature and the with-gas background temperature,
   the hardware processor prepares a plurality of the frame groups having different combinations of the frames, and determines the with-gas background temperature and the without-gas background temperature for each of the plurality of frame groups,
   the hardware processor that, for each of the plurality of frame groups, calculates the gas concentration length by using the with-gas background temperature and the without-gas background temperature that have been determined by the hardware processor; and the hardware processor that determines the gas concentration length from among the gas concentration lengths for the respective ones of the plurality of frame groups, the gas concentration lengths having been calculated by the hardware processor.

7. The gas concentration length measurement device according to claim 1, wherein
the hardware processor that extracts, from the chronological pixel data, frequency component data indicating a temperature change of a background of the monitoring target;
the hardware processor that calculates difference data indicating a difference between the chronological pixel data and the frequency component data; and
the hardware processor that calculates dispersion data indicating a dispersion of the difference data, wherein
the hardware processor determines the with-gas background temperature and the without-gas background temperature on the basis of the dispersion data.

8. The gas concentration length measurement device according to claim 7, wherein
the hardware processor determines maximum and minimum background temperature values from among background temperatures indicated by pieces of pixel data, in the dispersion data for the predetermined pixel, that are included in a frame group including a predetermined number of consecutive frames, and determines the maximum background temperature value as one of the without-gas background temperature and the with-gas background temperature and determines the minimum background temperature value as the other one of the without-gas background temperature and the with-gas background temperature,
the hardware processor prepares a plurality of the frame groups having different combinations of the frames, and determines the with-gas background temperature and the without-gas background temperature for each of the plurality of frame groups,
the hardware processor that, for each of the plurality of frame groups, calculates the gas concentration length by using the with-gas background temperature and the without-gas background temperature that have been determined by the hardware processor; and
the hardware processor that determines the gas concentration length from among the gas concentration lengths for the respective ones of the plurality of frame groups, the gas concentration lengths having been calculated by the hardware processor.

9. The gas concentration length measurement device according to claim 1, wherein
the hardware processor determines the with-gas background temperature and the without-gas background temperature for each of a pixel of interest and two or more peripheral pixels in a periphery of the pixel of interest, the pixel of interest and the two or more peripheral pixels included among the plurality of pixels constituting the infrared image,
the hardware processor that, for each of the pixel of interest and the two or more peripheral pixels, calculates the gas concentration length on the basis of the with-gas background temperature and the without-gas background temperature, having been determined by the hardware processor, for each of the pixel of interest and the two or more peripheral pixels; and
the hardware processor that determines the gas concentration length from among the gas concentration lengths for the respective ones of the pixel of interest and the two or more peripheral pixels, the gas concentration lengths having been calculated by the hardware processor.

10. The gas concentration length measurement device according to claim 1, wherein
the hardware processor that detects gas by using the infrared image; and
the hardware processor that, when gas is detected by the hardware processor, determines a pixel corresponding to a region in which gas is hanging, among the plurality of pixels, as the predetermined pixel.

11. The gas concentration length measurement device according to claim 1, wherein
the hardware processor that uses an infrared image among the plurality of infrared images and searches for an edge in the infrared image, wherein
the hardware processor does not use the chronological pixel data for the pixel corresponding to the edge found by the hardware processor for the determination of the with-gas background temperature and the without-gas background temperature.

12. The gas concentration length measurement device according to claim 1, wherein
the hardware processor determines maximum and minimum background temperature values for each of the predetermined pixel and two or more of the pixels that have been set in advance and are located in a periphery of the predetermined pixel, on the basis of the chronological pixel data for each of the predetermined pixel and the two or more pixels, and
the hardware processor that corrects the maximum and minimum background temperature values for the predetermined pixel on the basis of the maximum and minimum background temperature values for each of the two or more pixels.

13. The gas concentration length measurement device according to claim 1, wherein the gas concentration length measurement device calculates the gas concentration length by regarding an air temperature of a site at which the monitoring target is located as a temperature of the gas.

14. The gas concentration length measurement device according to claim 1, wherein the gas concentration length measurement device calculates the gas concentration length by using the with-gas background temperature and the without-gas background temperature for a first pixel and a second pixel, among the plurality of pixels constituting the infrared image, the gas concentration lengths for the first pixel and the second pixel being predicted as being equal.

15. A gas concentration length measurement method for measuring a gas concentration length by using an infrared image constituted of a plurality of pixels, the gas concentration length measurement method comprising:
acquiring image data representing a plurality of infrared images yielded by the plurality of infrared images of a gas leakage monitoring target being taken at a plurality of time points, the plurality of the infrared images each being taken in a specific wavelength region within the infrared band; and
generating chronological pixel data in which pieces of pixel data for pixels located at a same position in the acquired plurality of infrared images are lined-up in chronological order, and on the basis of the chronological pixel data for a predetermined pixel among the plurality of pixels, determining: a with-gas background temperature indicating a background temperature when gas is present in a predetermined region corresponding to the predetermined pixel; and a without-gas background temperature indicating a background temperature when gas is not present in the predetermined region.

16. A non-transitory recording medium storing a computer readable gas concentration length measurement program for measuring a gas concentration length by using an infrared image constituted of a plurality of pixels, the gas concentration length measurement program causing the computer of a gas concentration length measurement device to execute:
   acquiring image data representing a plurality of infrared images yielded by the plurality of infrared images of a gas leakage monitoring target being taken at a plurality of time points, the plurality of the infrared images each being taken in a specific wavelength region within the infrared band; and
   generating chronological pixel data in which pieces of pixel data for the pixels located at a same position in the acquired plurality of infrared images are lined-up in chronological order, and on the basis of the chronological pixel data for a predetermined pixel among the plurality of pixels, determining: a with-gas background temperature indicating a background temperature when gas is present in a predetermined region corresponding to the predetermined pixel; and a without-gas background temperature indicating a background temperature when gas is not present in the predetermined region.

17. The gas concentration length measurement device according to claim 1, wherein the hardware processor determines maximum and minimum background temperature values from among background temperatures indicated by the chronological pixel data, and determines the maximum background temperature value as one of the without-gas background temperature and the with-gas background temperature and determines the minimum background temperature value as the other one of the without-gas background temperature and the with-gas background temperature.

18. The gas concentration length measurement device according to claim 17, wherein the hardware processor calculates the gas concentration length by regarding an air temperature of a site at which the monitoring target is located as a temperature of the gas.

19. A gas concentration length measurement device for measuring a gas concentration length by using an infrared image constituted of a plurality of pixels, the gas concentration length measurement device comprising:
   a communication interface that receives input of image data representing a plurality of infrared images yielded by the plurality of infrared images of a gas leakage monitoring target being taken at a plurality of time points, the plurality of the infrared images each being taken in a specific wavelength region within the infrared band; and
   a hardware processor that generates chronological pixel data in which pieces of pixel data for pixels located at a same position in the plurality of infrared images input from the communication interface are lined-up in chronological order, and on the basis of the chronological pixel data for a predetermined pixel among the plurality of pixels, determines: a with-gas background signal indicating a signal when gas is present in a predetermined region corresponding to the predetermined pixel; and a without-gas background signal indicating a signal when gas is not present in the predetermined region.

20. A gas concentration length measurement device for measuring a gas concentration length by using an infrared image constituted of a plurality of pixels, the gas concentration length measurement device comprising:
   a communication interface that receives input of image data representing a plurality of infrared images yielded by the plurality of infrared images of a gas leakage monitoring target being taken at a plurality of time points, the plurality of the infrared images each being taken in a specific wavelength region within the infrared band; and
   a hardware processor that generates chronological pixel data in which pieces of pixel data for pixels located at a same position in the plurality of infrared images input from the communication interface are lined-up in chronological order, and that calculates the gas concentration length on the basis of a with-gas background temperature based on the chronological pixel data for a predetermined pixel indicating a temperature when gas is present in a predetermined region corresponding to the predetermined pixel, and a without-gas background temperature based on the chronological pixel data for the predetermined pixel indicating a temperature when gas is not present in the predetermined region.

21. A gas concentration length measurement device for measuring a gas concentration length by using an infrared image constituted of a plurality of pixels, the gas concentration length measurement device comprising:
   a communication interface that receives input of image data representing a plurality of infrared images yielded by the plurality of infrared images of a gas leakage monitoring target being taken at a plurality of time points, the plurality of the infrared images each being taken in a specific wavelength region within the infrared band; and
   a hardware processor that generates chronological pixel data in which pieces of pixel data for pixels located at a same position in the plurality of infrared images input from the communication interface are lined-up in chronological order, and that calculates the gas concentration length on the basis of a with-gas background signal based on the chronological pixel data for a predetermined pixel indicating a signal when gas is present in a predetermined region corresponding to the predetermined pixel, and a without-gas background signal based on the chronological pixel data for the predetermined pixel indicating a signal when gas is not present in the predetermined region.

* * * * *